United States Patent [19]

diZerega

[11] Patent Number: 5,173,404
[45] Date of Patent: Dec. 22, 1992

[54] IMMUNOASSAY FOR FOLLICULAR REGULATORY PROTEIN

[75] Inventor: Gere S. diZerega, Pasadena, Calif.

[73] Assignee: University of Southern California, Los Angeles, Calif.

[21] Appl. No.: 422,358

[22] Filed: Oct. 16, 1989

Related U.S. Application Data

[60] Division of Ser. No. 28,816, Mar. 26, 1987, Pat. No. 4,912,201, which is a continuation-in-part of Ser. No. 861,118, May 7, 1986, abandoned, which is a division of Ser. No. 661,002, Oct. 11, 1984, abandoned, which is a continuation-in-part of Ser. No. 475,416, Mar. 15, 1983, abandoned, and Ser. No. 912,445, Sep. 25, 1986, Pat. No. 4,764,502.

[30] Foreign Application Priority Data

Sep. 25, 1985 [CA] Canada .................................. 491514

[51] Int. Cl.$^5$ .................... G01N 33/53; G01N 33/543
[52] U.S. Cl. ..................................... 435/7.1; 435/806; 436/518; 436/811; 436/815; 436/817
[58] Field of Search ................... 435/7.1, 806; 436/65, 436/86, 811, 814, 815, 817, 906, 518

[56] References Cited

PUBLICATIONS

DiZerega et al., "Identification of Protein(s) Secreted by the Preovulatory Ovary Which Suppresses the Follicle Response to Gonadotropins", J. Clin. Endocrin. Metab. vol. 54, No. 6, pp. 1091–1096.

DiZerega et al., "Human Granulosa Cell Secretion of Protein(s) Which Suppress the Follicle Response to Gonkdotropins", J. Clin. Endocrin. Metabl, vol. 56, No. 1, pp. 147–155.

Di Zerega et al., "Identification of Proteins in Pooled Human Follicular Fluid Which Suppresses Follicular Response to Gonadotropins", J. Clin. Endocrin, Metab., vol. 56, No. 1, pp. 35–41.

Battin et al., "Effect of Human Menopausal Gonadotropin and Follicle Regulatory Protein(s) on 3$\beta$-Hydroxysteroid Dehydrogenase in Human Granulosa Cells", J. Clin. Endocrin. Metab., vol. 60, No. 6, pp. 1116–1119.

Primary Examiner—Esther L. Kepplinger
Assistant Examiner—Susan C. Wolski
Attorney, Agent, or Firm—Nilsson, Robbins, Dalgarn, Berliner, Carson & Wurst

[57] ABSTRACT

A protein having a molecular weight of from about 10,000 to 18,000 daltons, isoelectric points of from about pH 4.0 to 6.5 and having the reversible biological effect of inhibiting aromatase activity in a biological system, and antibodies to the protein, modulate follicular development and spermatogenesis and provide for diagnostic tests of gonadel functions.

10 Claims, 28 Drawing Sheets

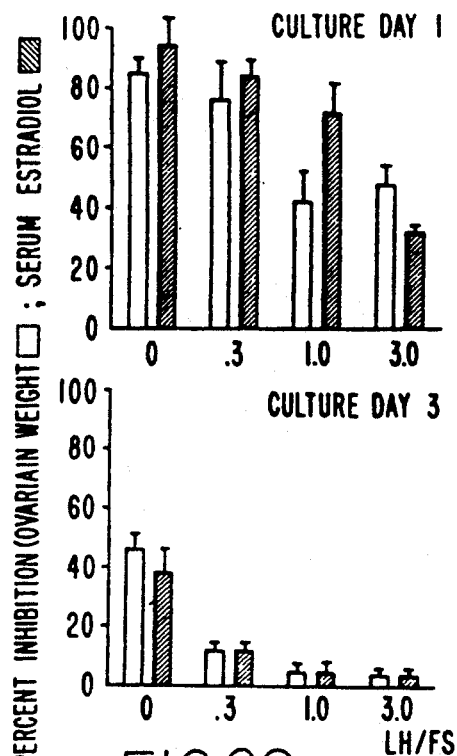
FIG. 20a
FIG. 20c
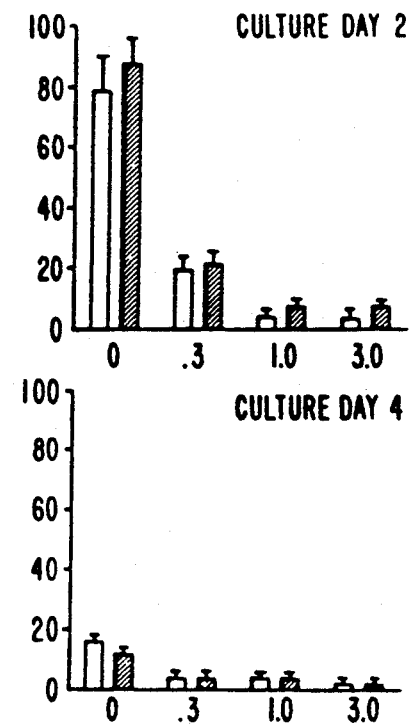
FIG. 20b
FIG. 20d
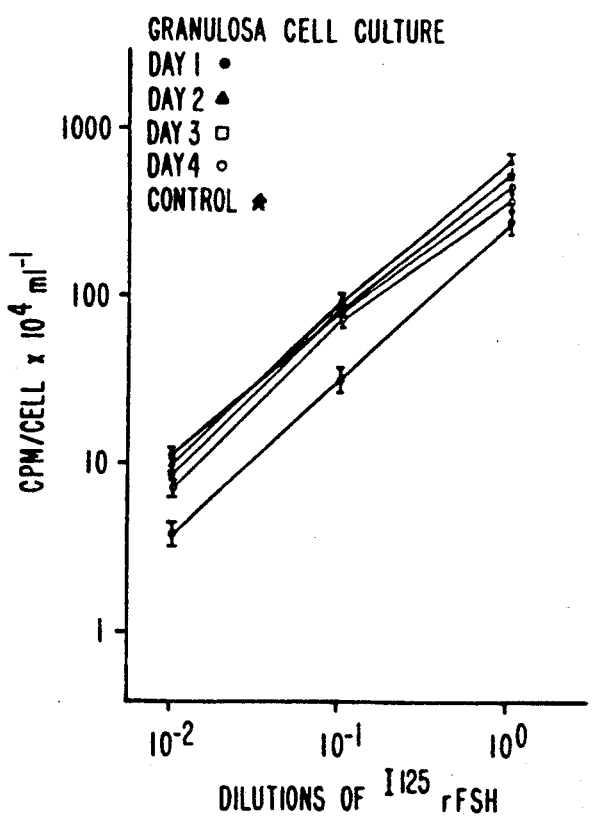
FIG. 21.

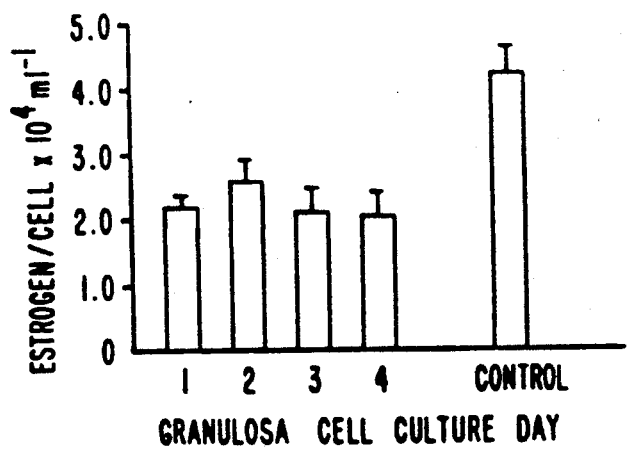
FIG. 22.
FIG. 23.
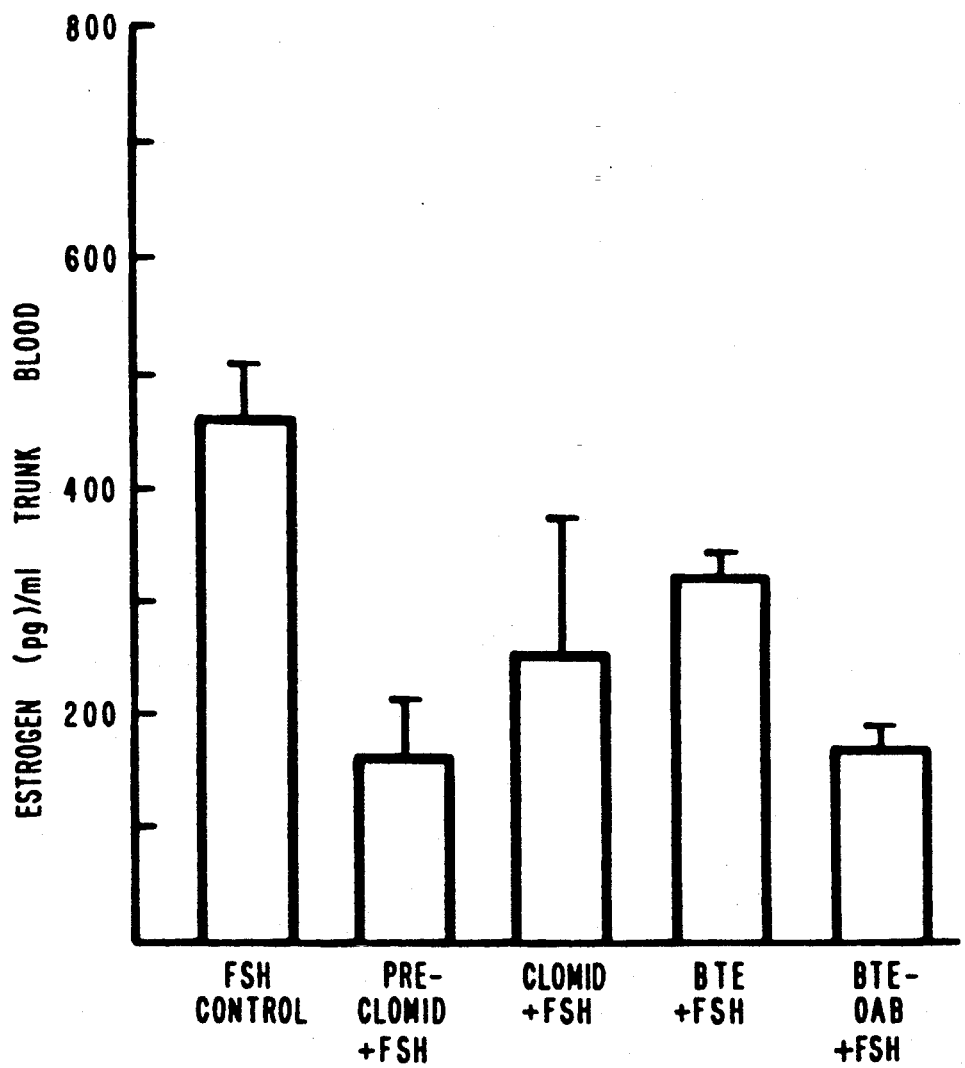

602B
621A

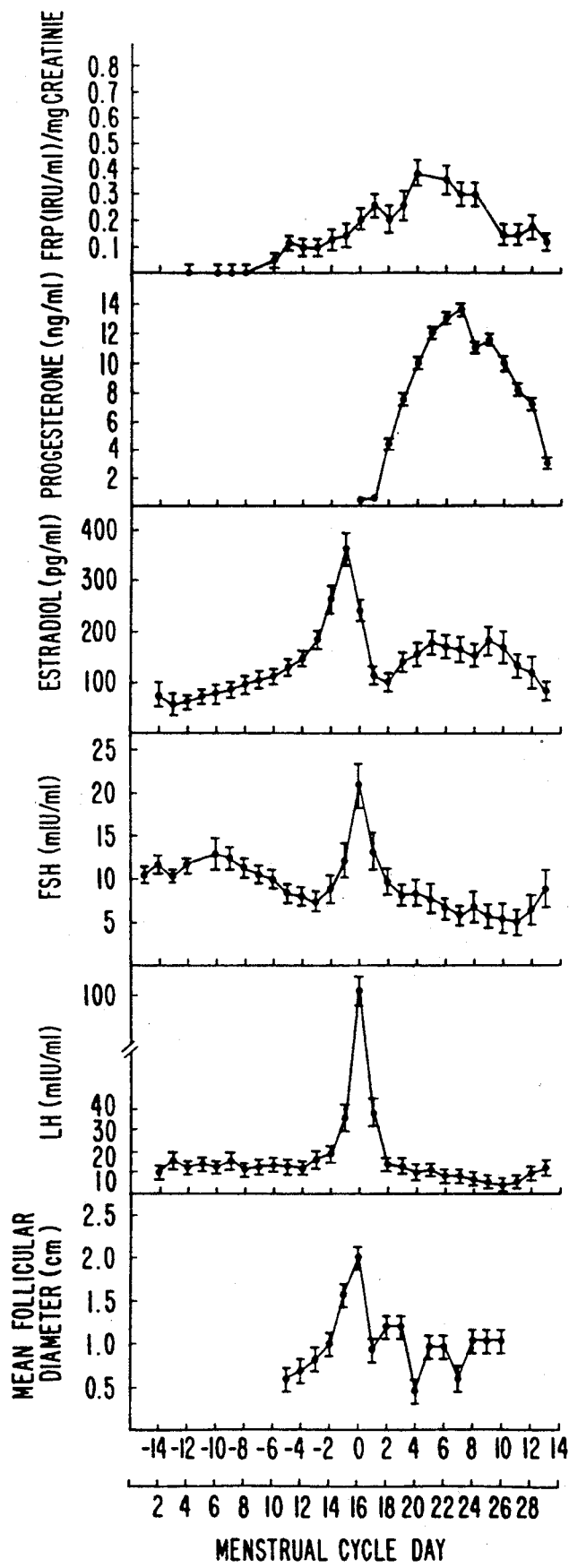

IMMUNOASSAY FOR FOLLICULAR REGULATORY PROTEIN

The United States Government has rights in this invention under Clinical Investigator Award HD-00401 and NIH Grant HD-05932.

This is a divisional of copending application Ser. No. 07/028,816 filed on Mar. 26, 1987, now U.S. Pat. No. 4,912,201, which is a continuation-in-part of application Ser. No. 06/861,118 filed May 7, 1986, now abandoned, which in turn is a divisional of Ser. No. 06/661,002 filed Oct. 11, 1984, now abandoned, which in turn is a continuation-in-part of Ser. No. 06/475,416 filed Mar. 15, 1983, now abandoned; and a continuation-in-part of Ser. No. 06/912,445 filed Sep. 25, 1986, now U.S. Pat. No. 4,764,502.

FIELD OF THE INVENTION

This invention relates generally to the field of biochemistry, and more particularly to the chemistry and physiology of gonadal function.

BACKGROUND AND SUMMARY OF THE INVENTION

The term gonad refers to the mammalian reproduction system, and includes both the testis and the ovary. The function of these glands is dependent upon the interrelationship of a number of hormones and proteins, many of which are found, in varying amounts, in both sexes.

The ovary is the essential female reproductive organ in which eggs are produced. In vertebrates there are commonly two ovaries, suspended from the dorsal surface of the broad ligaments, one on each side of the uterus. Adult human ovaries are composed of a fibrous vascular stroma in which are imbedded the Graafian follicles, which contain the eggs. The eggs are discharged by the bursting of the Graafian follicles on the surface of the ovary and are then immediately received into the mouth of the oviduct. Thereafter, the eggs flow through the fallopian tube to the uterus, covered by a mucous membrane known as the endometrium, where the fertilized ovum develops.

The egg cells or ova are periodically matured in the ovaries at intervals of approximately four weeks. At the end of each four week period, one egg reaches maturity and passes into one of the fallopian tubes. The egg descends gradually and remains viable for a short while, and during this time fertilization may take place.

Within the ovary, there is a layer of cells called the germinal epithelium. Here, the potential egg begins its existence and continues to develop until a primary follicle, i.e., a group of cells isolated from the main layer, is formed around the potential egg. During a lifetime, each human ovary forms between 200,000 and 400,000 follicles. Of all these potential eggs only a few develop into mature eggs, most of them degenerating. The primary follicle that does not degenerate increases in size, and the egg cell itself enlarges up to thirty times its original size.

Other changes occur in the areas adjacent to the follicle. As the follicle matures, it moves toward the surface of the ovary and when the maturation process is complete, the follicle protrudes from the surface. At this time, ovulation occurs, i.e., the follicle bursts and the egg is expelled from the surface of the ovary.

The developing follicle produces sex hormones by metabolizing pre-hormones using a series of enzymes: $3\beta$-ol dehydrogenase, $17\alpha$-hydroxylase, hydroxysteroid dehydrogenase, and aromatase. Aromatase is a central enzyme in the production of sex hormones referred to as estrogens (estradiol, estrone and estriol).

Estrogenic hormones play a particularly important role in both the menstrual cycle and the reproductive cycle. Although $17\beta$-estradiol is the principal estrogenic hormone, a number of other estrogenic substances have been isolated, including estriol and estrone. These hormones induce the growth of the vaginal epithilium and secretion of mucous by the glands of the cervix and initiate the growth of the endometrium.

The corpus luteum, which fills a ruptured Graafian follicle in the mammalian ovary, produces at least three hormones, progesterone, $17\beta$-estradiol and relaxin. Progesterone acts to complete the proliferation of the endometrium, which was initiated by the estrogenic hormones, and to prepare it for the implantation of the ovum.

This reproductive cycle is well regulated as long as the production and secretion of both the sex hormones from the ovaries and the gonadotropic hormones of the pituitary gland are within normal limits. The anterior lobe of the pituitary, by manufacturing and secreting the gonadotropic hormones, controls the production of the sexual hormones in the ovaries and stimulates the development of the reproductive organs and the maintenance of their structure. The ovaries, under control of the gonadotropic hormones, produce the female sexual hormones. In turn, the rate of production of gonadotropins by the pituitary is influenced by the production of sex hormones. The effects are mutual and the two glands maintain an exact balance in hormone production.

More specifically, the follicle-stimulating hormone (FSH) from the pituitary stimulates the Graafian follicles, which thus produce estrogens. Estrogens not only inhibit FSH production through negative feedback on the pituitary, but also stimulate the pituitary to increase its production of luteinizing hormone (LH) through positive feedback. This hormone (LH) in turn brings about ovulation of the Graafian follicle. After the ova are discharged, the LH stimulates the empty follicle, now the corpus luteum, to produce progesterone. This hormone brings about the changes in the reproductive organs required for the development of the embryo. The progesterone then partly inhibits the pituitary from producing more LH. Thus, there is no further ovulation. The subsequent fall in progesterone then releases the pituitary inhibition allowing for the production of FSH to being the process anew.

When pregnancy occurs, the placenta of the embryo itself produces human chorionic gonadotropin (hCG), which stimulates the continuing production of progesterone from the corpus luteum, thus preventing menstruation and stimulating the continuing development of the uterus. This progesterone also inhibits further ovulation in spite of the presence of the hCG from the placenta.

The gonadotropic hormones have been determined to be proteins, with variable amounts of carbohydrates, and their structures are known. The molecular weight of human LH is about 26,000, and that of human FSH is about 30,000. The cellular response to gonadotropic hormones is translated through cellular receptors. These receptors are located within the cell membrane and are specific for each gonadotropin, thus, LH only activates LH receptors and FSH only activates FSH receptors.

Non-abortifacient means for the avoidance of pregnancy include oral contraceptive medications which contain estrogen and/or progesterone-like steroidal sex hormones. These medications, by raising the level of sex hormones in the blood stream, generate a cervical mucous which is hostile to spermatazoa. With increased levels of such hormones the endometrium tends to resist implantation of the fertilized ova. Further, the excess hormones provided by oral contraceptives directly inhibit the release of LH and FSH by the pituitary. As such, the ovarian cycle is disrupted and ovulation does not occur. The complications of such steroidal contraceptive medications, e.g., nausea, vomiting, weight gain, hypertension and tumor stimulation, adverse effects on calcium and phosphate metabolism, are well known and need not be discussed at length. However, these side effects result not only from the abnormally high levels of steroidal hormones in the blood stream, but from disruption of the hormonic homeostatis of the organism, i.e., the cycle of hormone adjustment between the ovary and the pituitary gland.

Accordingly, it has been a desideratum to provide a contraceptive medication which permits the regulation of the ovarian process without an accompanying disruption of the hormonic homeostatis of the organism.

While sex hormones are commonly referred to as male (androgenic) and female (estrogenic) hormones, these substances, including the proteinaceous substances associated therewith, are each important in the regulation of both the male and the female reproductive systems. For example, the luteinizing hormone (LH) and follicle stimulating hormone (FSH) play important roles in the regulation of the testis. These gonadotropins are synthesized and released in the male pituitary under the regulation of a hypothalamic peptide (luteinizing hormone releasing hormone) which is synthesized in the hypothalamus. LH binds to the surface receptors on the Leydig cells and promotes increased testosterone synthesis. It should be noted that testosterone synthesis is also regulated by the prevailing estradiol concentration, with high estradiol levels decreasing testosterone synthesis.

Spermatogenesis is a complex event where primitive germ cells (the spermatogonia) proceed through multiple cell divisions, in an orderly progression from spermatogonia to spermatocyte to spermatid, in order to form mature spermatozoa. In this progression, the intergenderal communality of the regulating hormones and proteins in the gonads is demonstrated by the fact that estrogen is a necessary component in the conversion of spermatogonia to spermatocytes. Further, the enzyme aromatase is a central enzyme in the conversion of androgens to estrogens. It should be noted that aromatase is a paracrine (intragonadal) enzyme that has been shown to be critical to the regulation of fertility in both the male and female gender of mammalian species.

It has also been a desideratum to provide a facile method for the regulation of fertility in both the male and female gender of mammalian species. It should be understood that the regulation of fertility, as employed herein, refers to a method and/or a composition of matter associated therewith, which enables either an increase or a decrease in mammalian fertility, that is, fertility control as opposed to mere contraception.

The present invention accomplishes the foregoing objectives by providing a protein moiety which enables the intragonadal modulation of the level of aromatase in a mammalian host and thus can regulate the maturation of ovarian follicles and the production of viable ova and regulate spermatogenesis and the production of mature spermatozoa without disturbing the normal level of sex hormones in the body, and permit the evaluation and diagnosis of gonadal function and dysfunction.

According to the invention a purified, nonsteroidal proteinaceous material or moiety having a measurable molecular weight of up to about 20,000, an isoelectric point of from about pH 3.5 to about pH 7.0 is provided, and is characterized by having the biological effect of inhibiting aromatase activity as defined by the extent of the conversion of androgens to estrogens. The protein inhibits intragonadal aromatase activity, modulates the intragonadal activity of 3$\beta$-ol dehydrogenase, inhibits the development of granulosa cell LH receptors and prevents the maturation of mature ova and the production of mature spermatozoa. The term protein moiety, as used herein, refers to a protein, proteins or functional operative groups thereon which produce the described results. The production and activity of the protein moiety is interspecies, and is effective in both monotocous and polytocous mammals. Further, methods are provided for the isolation, purification and production of the protein, and for the use thereof in the regulation of fertility control.

In another aspect of the invention, antibodies are provided which inhibit the natural production of the protein with a corresponding increase in aromatase activity resulting in the promotion of follicular development, ovum maturation and spermatogenesis. Thus, mammalian fertility may be controlled substantially independently of exogenous sex hormones and without modulating extragonadal hormone levels. In yet another aspect of the invention, methods are provided for the use of antibodies to the protein for the quantification of the level of the protein in body fluids, thus permitting the evaluation and diagnosis of gonadal function and dysfunction.

For convenience, the intragonadal and follicular regulating protein is referred to herein as FRP.

BRIEF DESCRIPTION OF THE DRAWINGS

FIGS. 20a-d: Effect of human guanulosa cell culture media (2 ml/rat) on the inhibition of ovarian weight augmentation and serum estradiol responses to LH/FSH stimulation in the immature, hypophysectomized, DES-treated rat. Each value represents the mean±SE of nine rats. Granulosa cells were aspirated from three patients (no. 5-7) who underwent clomiphene (150 mg/day, menstrual cycle days 3-7) and hCG (4000 IU, 36 hours before aspiration) treatment.

FIG. 21: Binding of FSH to rat granulosa cells collected from the HIFR-hMG bioassay of non-LH/FSH-stimulated human granulosa cell culture medium (see FIG. 20). Specific binding of rat FSH (rFSH) to granulosa cells was determined by incubating three concentrations of labeled rFSH in the presence and absence of excess unlabeled rFSH.

FIG. 22: Aromatase activity of rat granulosa cells derived from the HIFR-hMG bioasssay of human granulosa cell culture medium (see FIG. 20, non-LH/FSH-stimulated cultures). Control determinations were performed on rat granulosa cells collected from HIFR-hMG-treated rats which did not receive culture medium injections. Inhibition of relative estrogen production by rat granulosa cells in the presence of $10^{-7}$M androstenedione was seen throughout all four days of human granulosa cell culture medium treatment.

FIG. 23: Inhibition of serum estradiol levels in the peripheral trunk blood of immature, hypophysectomized, diethyl stilbesterol and FSH treated rats (FSH control) by: ovarian vein serum from FSH treated baboons before (pre clomid+FSH) and after (clomid+FSH) clomiphene citrate therapy; bovine testis extract, (BTE+FSH); and bovine testis extract which binds to matrix Gel Orange A and which elutes with 0.5M KCl+TRIS (BTE-OAB+FSH).

FIGS. 35a-f: levels of FRP in the urine of twelve regularly menstruating women over time, the simultaneously-obtained serum levels of LH, FSH, estradiol and progesterone, and the ultrasonon-graphic determination of the largest follicle diameter.

DETAILED DESCRIPTION OF THE PREFERRED EMBODIMENT

Figure 1:
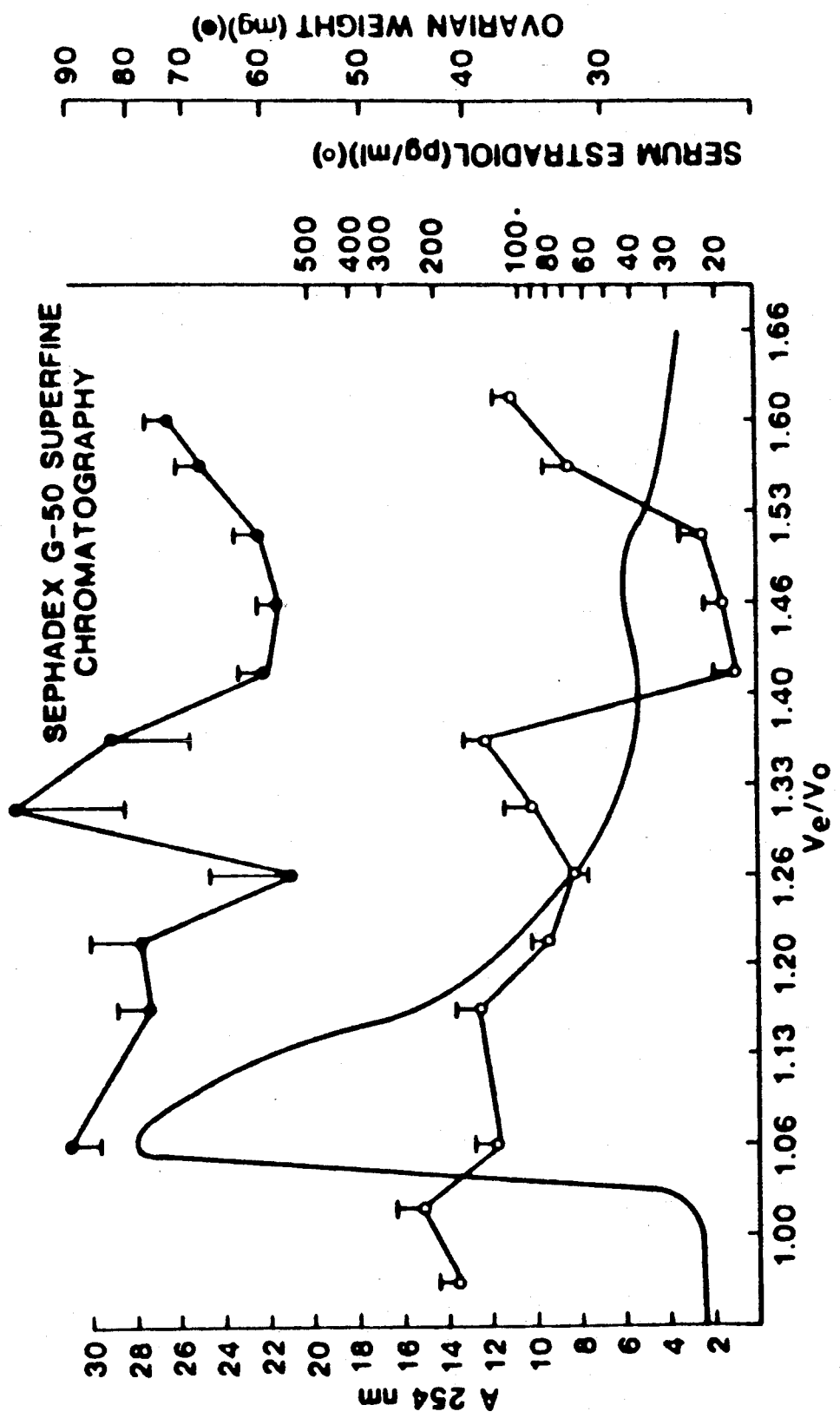
FIG. 1 shows the elution profile of a preovulatory patient's ovarian venous effluent after partial purification using Sephadex G-50 superfine chromatography with absorbance measured at 254 nm. The responses, by bioassay of hypophysectomized, twenty-three day old, DES-treated rat ovaries receiving hMG therapy to aliquots of the Sephadex G-50 fractions in terms of ovarian weight and serum 17$\beta$-estradiol concentrations are overlayed. Fractions eluting with a $V_e/V_0$ of 1.42–1.55 actively inhibited both parameters.

The embodiment hereinafter set forth relates to the isolation and purification of the intragonadal protein moiety and its use in the inhibition of the activity of the aromatase enzyme, modulation of 3β-ol dehydrogenase activity, regulation of mature ova and sperm formation and the production of the protein moiety by cell cultures.

The protein moiety is isolated from the ovary or the testis by methods such as salt fractionation and dialysis, and chromatography. Granulosa or Sertoli cells may be cultured to produce substantial amounts of the protein moiety, which is then similarly purified.

Generally, gonadal fluid may be obtained by compression of appropriate mammalian gonads, and purified by chromatographic separation to yield FRP, although initial salt fractionation and subsequent electrophoretic separation vastly improve the separation procedure.

More specifically, FRP may be extracted from biological fluids including ovaries, testis, rete testis fluid, lymph, blood, and ovarian follicular fluid from mammalian species. To illustrate, a preferred process for the separation and purification of FRP as set forth in the Examples is summarized as follows:

1. Biological fluid is mixed with saturated ammonium sulfate to achieve a 30–55% concentration.
2. The precipitate from step 1 is resuspended in TRIS buffered saline (20 mM, pH 7.5) and dialyzed against 3 changes of distilled water (36 hours, 4° C.) to remove the remaining ammonium sulfate.
3. The retentate from step 2 is passed through a hydroxylapatite column which is subsequently washed with 2 column volumes of TRIS buffered saline (20 mM, pH 7.5). The column is then eluted in a stepwise fashion with 0.1 mM phosphate buffer followed by 0.5M phosphate buffer.
4. The eluent from the 0.5M phosphate buffered saline is passed through a Sephacryl G-200 column and eluted with TRIS buffer (20 mM, pH 7.5).
5. The eluent from step 4 which elutes in the >40,000 molecular weight range is charged onto a Matrix gel Orange A column which was previously equilibrated with TRIS buffer (20 mM, pH 7.5). The Matrix gel Orange A column is washed with 3 column volumes of TRIS buffer and then eluted with TRIS buffer (20 mM, pH 7.5) to which has been added 0.5M KCl.
6. The TRIS+0.5M KCl eluant from step 5 after dialysis is charged onto a hydrogen ion exchange column previously equilibrated with imidazole buffer (0.25M, pH 7.4). The column is eluted with buffer over the pH range 7.4 to 3.6.
7. The eluent fractions corresponding to about pH 7.4 to pH 3.6 from step 6 are eluted through a TSK 3000 column with TRIS buffer (pH 7.5, 20 mM) by high performance liquid chromatography. The fraction corresponding to 35 to 37 minutes in FIG. 8 (analytical column) and 77.8 to 78.0 minutes in FIG. 9 (preparative column) contain FRP.
8. The TRIS+0.5M KCl eluent from step 5 is layered on an agarose gel or Sephadex G-75 column which have been previously charged with ampholines (pH 3–8). A current is passed through the support matrix of sufficient length and wattage to allow equilibration of proteins at their isoelectric points. The fractions recovered from these electrophoretic separations corresponding to isoelectric points of from pH 3.5 to pH 7.0 contain FRP.
9. The TRIS+0.5M KCl eluent from step 5 can be charged onto a hydrophobic reverse phase column. The column can be eluted with increasing concentrations of organic reagents (acetonitrile, trifluoroacetic acid). FRP can be separated from the other components of step 5 eluent in this fashion using differential solubility to organic solvents.

The biological effect of the moiety was assessed in laboratory animals by determining variations in ovarian weight and analyzing body fluids for steroid hormones and enzyme activities. Aromatase inhibition was determined by incubating granulosa cells in the presence of a substrate and FRP and measuring the amount of estrogen formed. The $3\beta$-ol dehydrogenase was found to be modulated by incubating granulosa cells in the presence of a substrate and GRP and measuring the amount of progesterone formed. The addition of labelled LH and FSH to in vitro granulosa cell cultures showed a decrease in LH receptors in the cells, and no change in FSH receptors grown in the presence of FRP.

Regularly ovulatory primates were exposed to FRP and in all instances the ovarian cycle was modified, along with follicular growth, as evidenced by estrogen and progesterone levels, without the concomitant alteration of LH and FSH levels. In subsequent cycles, the primates had timely menstrual onset and showed no toxic treatment effects. Male animals were injected with FRP and exhibited reduction of spermatogenesis.

Pharmaceutically effective amounts may be administered to individuals orally, by injection, membrane absorption or other means which will be apparent to those skilled in the art. A particularly advantageous method of administration comprises the introduction of an effective amount of the moiety to the absorbent mucous membranes.

Since FRP inhibits aromatase and normal follicle maturation, it plays a central role in the ovulatory process. Accordingly blockage of the GRP activity allows for the maturation of multiple follicles to ovulatory status. The protein may be coincubated with hybrid cells in vitro to produce antibodies to proteins from different species. The antibody produced by the hybrid cultures and collected by chromatography may be injected into females thus blocking the action of the follicular protein and allowing for development and eventual ovulation of one or more follicles.

Agricultural uses of a similarly prepared antibody allow for the maturation of multiple follicles in livestock which could be collected, fertilized in vitro and reinserted into a properly prepared surrogate. FRP antibodies may also be employed to quantify the level of existing FRP in body fluids for a wide variety of diagnoses.

EXAMPLES

The following examples will describe in detail the identification, separation, activity and effects of the purified intragonadal regulatory protein, according to the following outline:

I. Identification of the Sources and Physical Characteristics of FRP.
  A. Ovarian Venous Blood (Example One).
  B. Human Follicular Fluid (Example Two).
  C. Porcine and Bovine Follicular Fluid (Example Three).
  D. Granulosa Cells and Cell Culture (Example Four).
  E. Testis Fluid (Example Five).
  F. Sertoli Cells and Cell Culture (Example Six).

II. Biological Activity
  A. Aromatase Inhibition (Example Seven).
    1. Non-Competitive Inhibition (Example Eight).
  B. Modulation of $3\beta$-ol-dehydrogenase Activity (Example Nine).
  C. Inhibition of LH-hCG Receptor Formation (Example Ten).
  D. Inhibition of FSH Augmented Adenylate Cyclase Activity (Example Eleven).
  E. Reduction of Follicular Atresia (Example Twelve).

III. Whole Animal Studies
  A. Inhibition of Primate Ovarian Cycles (Example Thirteen).
  B. Inhibition of Spermatogenesis (Example Fourteen).

IV. Preparation of FRP Antibodies (Example Fifteen) and use in diagnostic procedures (Example Sixteen).

I. IDENTIFICATION OF THE SOURCES AND PHYSICAL CHARACTERISTICS OF FRP

Example One

Identification of Follicular Inhibitory Protein(s) in Ovarian Venous Blood

Ovarian venous blood (5 ml) was collected from six women (aged 26, 28, 31, 36, 37 and 41 years) undergoing laparotomy for indications not related to ovarian dysfunction on days 12-14 after the onset of the last menstrual period. Patients 1-3 maintained regular menstrual cycles, while patients 4-6 were anovulatory, as evidenced by oligomenorrhea and a lack of large antral follicles in the ovarian cortex. A 25-gauge needle was inserted into the venous drainage within the infundibulo-pelvic ligament, and free-flowing blood was aspirated. In addition, the locus of the preovulatory follicle was determined by direct visual inspection. Peripheral serum (10 ml) was collected concurrently from an antecubital vein. Serum was separated by centrifugation (800×g for fifteen minutes) of the clotted specimen and stored frozen ($-35°$ C.) until fractionation. Concentrations of 17$\beta$-estradiol in ovarian (1340, 886, and 470 pg/ml) and peripheral (248, 261, and 201 pg/ml) venous samples collected from patients 1, 2 and 3, respectively, were consistent with the preovulatory 17$\beta$-estradiol levels reported for normal women. In addition, comparable samples from anovulatory patients 4-6 contained low levels of 17$\beta$-estradiol in both ovarian (200 pg/ml) and peripheral (50 pg/ml) sera. Slowly thawed serum was fractionated by the dropwise addition of an equal volume of saturated ammonium sulfate under persistent agitation at 4° C. After twelve hours, the precipitate was resuspended (2:1, vol/vol) with 10% ammonium sulfate. After twelve hours of additional agitation and centriguation (3000×g for 30 minutes, the supernatant was dialyzed with 10,000 molecular weight exclusion membranes against Dulbecco's phosphate-buffered saline (PBS; 0.025M; pH 6.8) for 16 hours. The retentate was passed through a Concanavalin A-linked Sepharose 4B (Con A) column (5 ml; Pharmacia, Piscataway, N.J.) which was washed with 5 vol 0.5M NaCl, pH 7.4, then further eluted with 0.5M $\alpha$-methyl-D-mannoside in PBS at a flow rate of 20 ml/h at 4° C.

Additional fractionations were performed where indicated on a Sephadex G-25 (superfine) column (1.6×50 cm; Vo=60 ml; 5 ml/h; 4° C.) with PBS. All Sephadex molecular weight sieving was performed using a reverse flow technique. Both Sephadex G-50 and G-25 were prepared according to the instructions of the manufacturer and equilibrated in the elution buffer. To increase resolution, the smallest of the Sephadex beads were removed by direct pipetting of the surface before degassing and column packing (10 mm H$_2$O). Elution profiles were determined using an ISCO absorbance meter at 254 nm.

The activity was assessed in twenty-three-day-old Sprague-Dawley rats (45-55 g) 2 days after hypophysectomy which were kept at 25° C. with intervals of fourteen hours of light and ten hours of darkness. Animals were caged in groups of three and given rat chow and water ad libitum. Silastic implants containing DES (diethylstilbestrol) were prepared as follows. Ten grams of Silastic (TM) polymer were mixed with 3 g DES for thirty minutes at 16° C.; thereafter, four drops of stannous octoate catalyst were added, with an additional ten minutes of mixing. The material was passed through a Luer-lock syringe (id, 1 mm) into a steaming (95° C.) 0.9% NaCl water bath and annealed for two hours. DES-containing Silastic implants (1×5 mm) were inserted sc in the hypophysectomy incision forty-eight hours before assay. The assay design consisted of three rats at each dose of reference preparation and unknown. Forty-eight hours after hypophysectomy, animals were given either varying concentrations of gonadotropins (LH:FSH, 1:1) dissolved in 0.15M NaCl with 1% bovine serum albumin and/or equal volumes of test fractions in two divided daily doses. Twenty-four hours after the initial injection, animals were sacrificed by decapitation, and ovaries were removed, trimmed and weighed on a Roller-Smith balance. Rat trunk serum 17$\beta$-estradiol determinations were performed by methods described in Goeblesmann et al., in Leprow et al (Eds.) *Vasectomy: Immunological and Pathologic Effects in Animals and Man*, Academic Press, New York, p. 165. Control determination of chromatography fractions containing inhibitory activity was performed by heating (56° C.; for thirty minutes) or trypsin digestion (20 mg/100 ml) of representative samples for 4 hours.

FIG. 1 compares absorbency, at 254 nm, of the Sephadex G-50 fractions from a preovulatory ovarian venous sample of patient 1 to the bioassay results of the sample, as determined by rat ovarian weight and serum 17$\beta$-estradiol concentrations. An initial peak rose to 28 absorbency units, followed by a gradual downward slope, with the emergence of a smaller second peak ($V_e/V_o = 1.42-1.55$). When these eluents were tested in the bioassays, the combined rat ovarian weights ranged from 57-100 mg, and rat serum 17$\beta$-estradiol levels ranged from 70-230 pg/ml throughout the initial fractions. Thereafter, fractions with a Ve/Vo of 1.42-1.55 corresponded to an inhibition of hMG-induced ovarian stimulation in the bioassay, as evidenced by a decrease in ovarian weight (59+0.5 mg) and a significant ($P<0.01$, by paired t test) decrease in serum 17$\beta$-estradiol to levels less than 25 pg/ml. As a consequence, these fractions were pooled and processed for dose response activity. Peripheral and ovarian venous blood collected from the ovary contralateral to the site of ovulation in patient 1 demonstrated similar G-50 elution profiles (data not shown). However, when representative fractions were tested by bioassay, no reduction in ovarian weight or serum 17$\beta$-estradiol was found. Further, ovarian venous blood preparations from the anovulatory patients also failed to suppress the response of the ovaries to hMG stimulation. However, ovarian venous sera from the ovulatory ovary of patients 2 and 3 had a similar Sephadex G-50 elution profile. Fractions with a $V_e/V_o$ of 1.48-1.60 suppressed the response of rat ovarian weight (57.4±2.1 vs. 81.2±4.5 mg; $P<0.05$) and serum 17$\beta$-estradiol concentrations (25 vs. 68-120 pg/ml; $P<0.01$) to hMG stimulation. When active fractions from the G-50 eluents of patients 1-3 were heated or trypsin digested, they lost their ability to suppress ovarian weight or 17$\beta$-estradiol secretion in response to hMG stimulation.

Figure 2A:
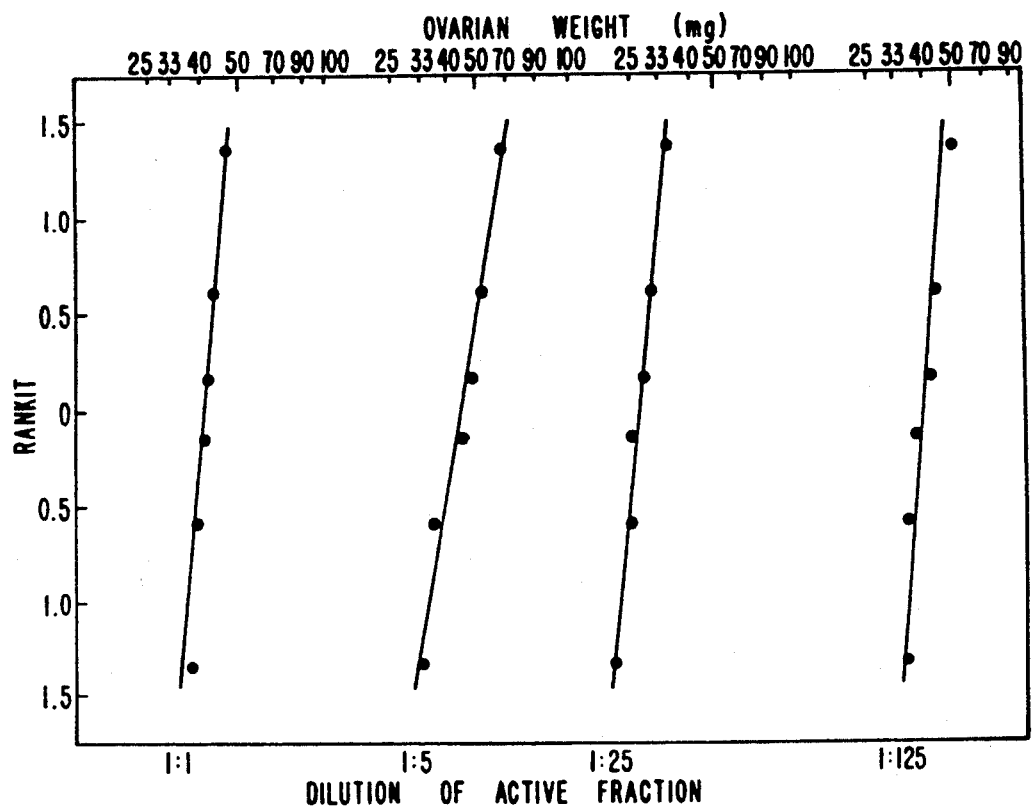
FIG. 2a shows Rankit analysis to determine the central tendency for ovarian weight inhibition at each dose tested.
Figure 2B:
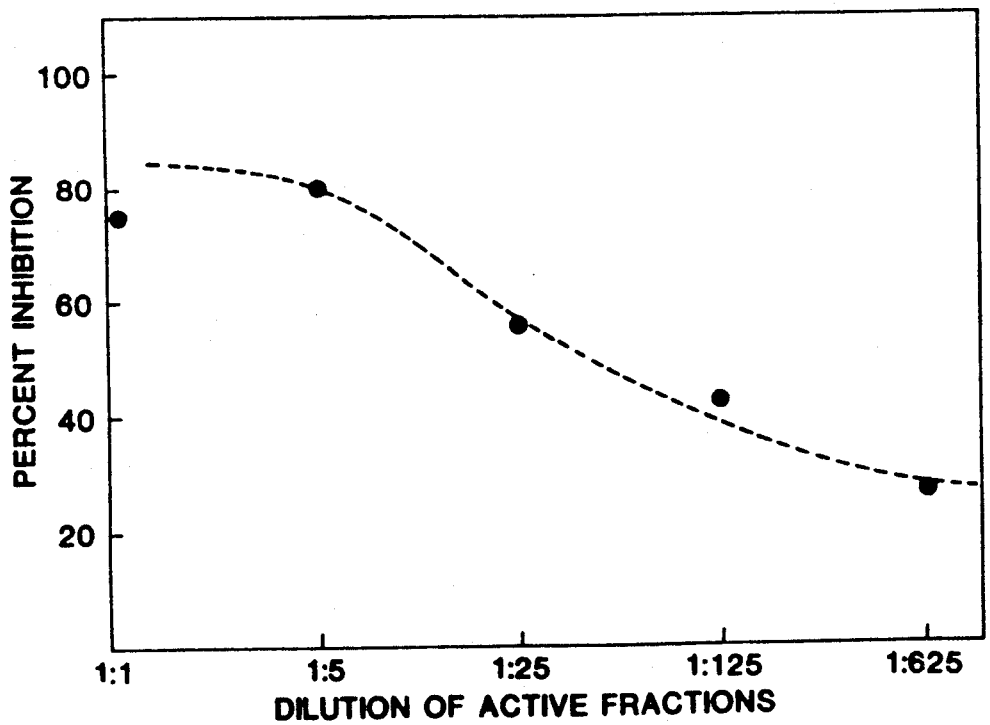
FIG. 2b shows the dose-response of active Sephadex G-50 fractions ($V_e/V_0 = 1.42$–1.55) in bioassay of hypophysectomized, twenty-three day-old, DES-treated rat ovaries receiving hMG treatment.

FIG. 2 depicts the dose-response curve of ovarian weight suppression in the DES-treated rat ovaries by active Sephadex G-50 fractions ($V_e/V_o = 1.42-1.55$) derived from patient 1. Analysis of the rat ovarian weight and serum 17$\beta$-estradiol concentrations revealed (insert: central tendency ovarian weights), a linear dose-response pattern. When these same fractions were treated with heat or trypsin, no suppression of ovarian weight was present.

The isoelectric point of active fractions eluted from the Sephadex G-50 column was estimated by ampholyte displacement chromatography. Pooled aliquots (1 ml) of active fractions were layered on a Polybuffer Exchanger 94 (25 ml; equilibrated to pH 7.4 with 0.025M Imidazole HCl) column (0.6×30 cm). Fractions were eluted with Pharmalyte(TM) Polybuffer(TM) 74-HCl adjusted to pH 4.0 with HCl 1N at 10 ml/h at 4° C. Fractions that eluted at a pH greater than 7.4 were collected and rechromatographed in the same Pharmalyte column reequilibrated to pH 9.4 with ethanolamine 0.025M and eluted with Polybuffer 96 adjusted to pH 6.0 with 1N KOH.

Figure 3:
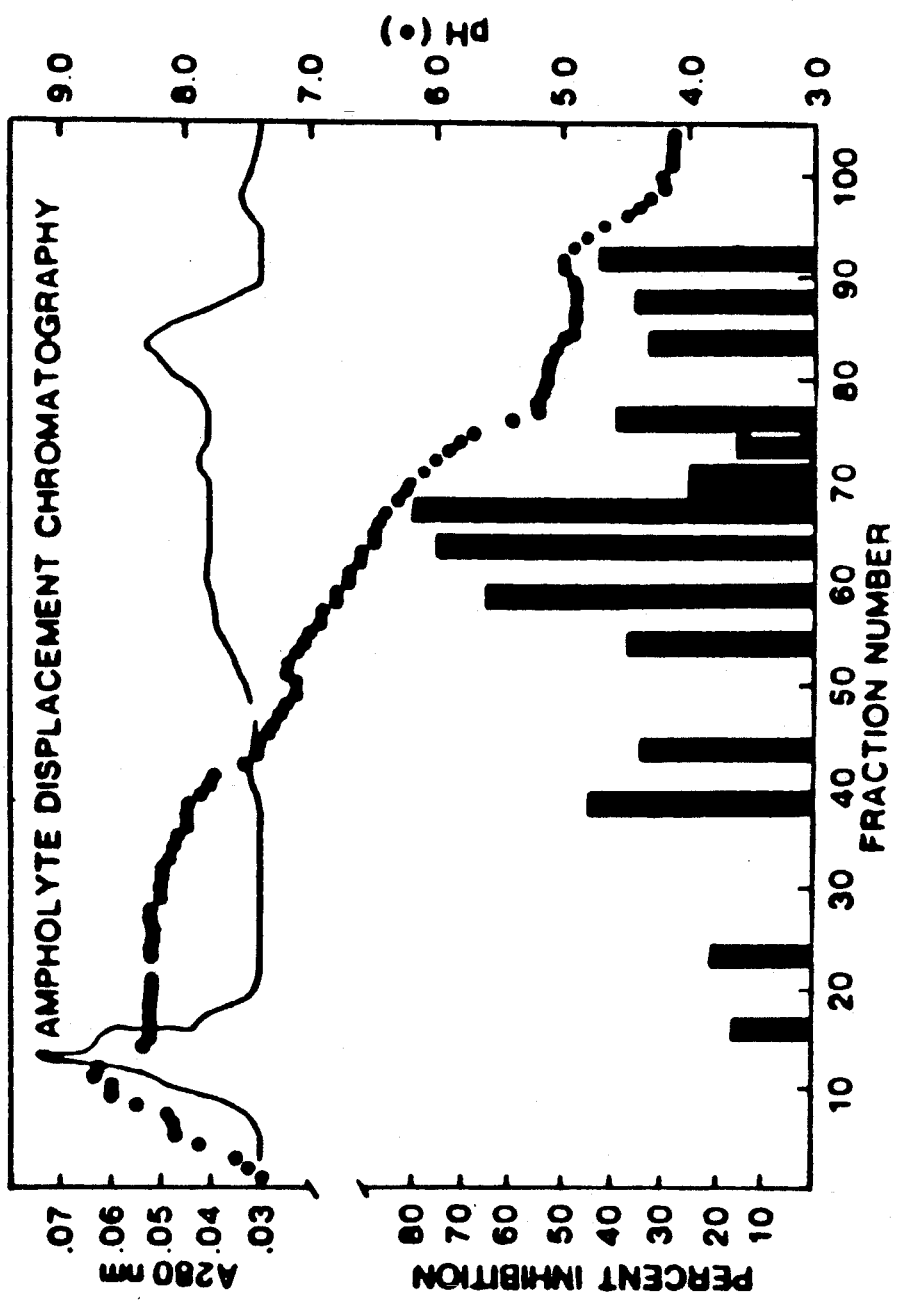
FIG. 3 shows a compilation of the active Sephadex G-25 fractions ($V_e/V_o = 1.20$–1.25) pooled and developed by ampholyte displacement chromatography. Fractions corresponding to a pH of 6.1–6.5 manifest inhibitory activity in excess of 50% tested in the bioassay with hypophysectomized, twenty-three-day-old, DES-treated rat ovaries receiving hMG therapy (ovarian weight). Ampholyte displacement chromatography of the fractions with follicle-inhibiting activity obtained on Sephadex G-25 gel filtration ($V_e/V_o = 1.20-1.25$).

FIG. 3 complies the active Sephadex G-25 fractions ($V_e/V_o$=1.20-1.25) pooled and developed by ampholyte displacement chromatograms from patient 1 for elution ranges pH 9-4. The bioassay results from ovarian weight and serum 17$\beta$-estradiol concentrations from representative fractions suggested that the isoelectric point of the active Sephadex G-50 eluents from patient 1 were between pH 6.2-6.5.

Fractions corresponding to a pH of 6.1-6.5 manifest inhibitory activity in excess of 50% tested in the bioassay with hypophysectomized, twenty-three-day-old, DES-treated rat ovaries receiving hMG therapy (ovarian weight). Ampholyte displacement chromatography of the fractions with follicle-inhibiting activity was obtained on Sephadex G-25 gel filtration fractions with $V_t/V_o$=1.20-1.25.

Figure 4:
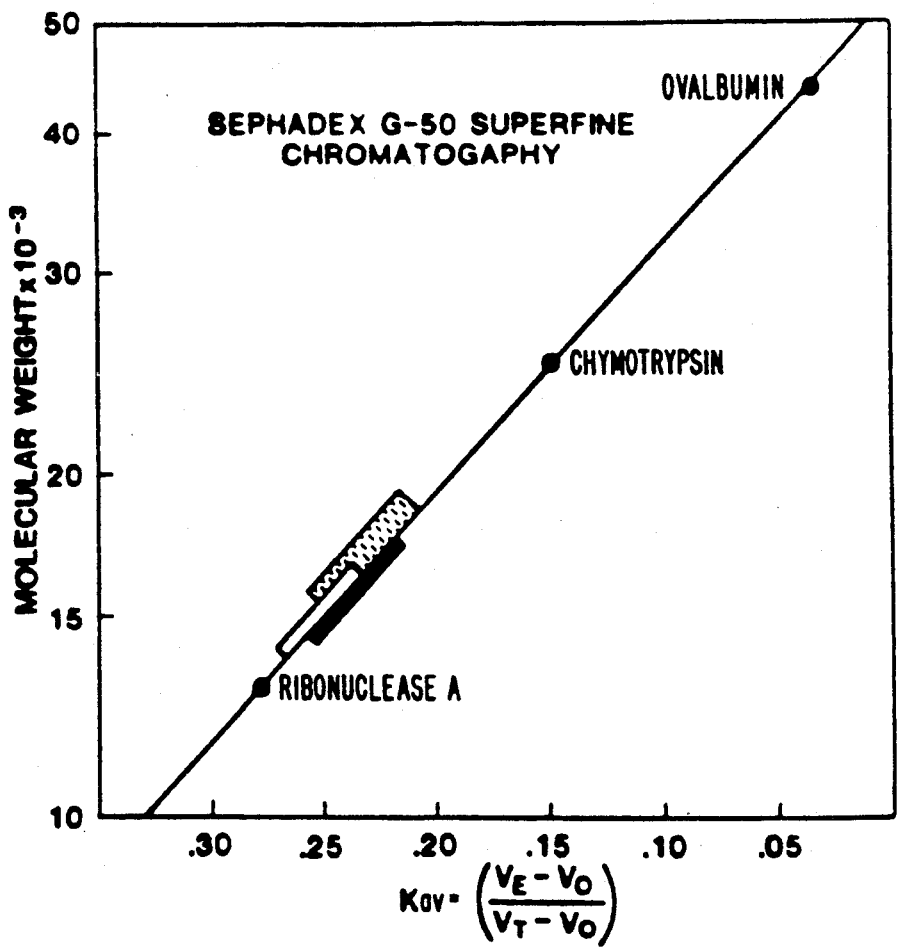
FIG. 4: $K_{av}$ of the active portion of preovulatory ovarian venous effluents from patients 1-3 eluted through a Sephadex G-50 superfine column calibrated with molecular weight standards. The molecular weights estimated in this manner were 14,000-16,500 for patient 1, (□) 14,000-17,000 for 2 (■) and 16,000-18,000 for patient 3 (▨).

FIG. 4 depicts the $K_{av}$ values for the molecular weight standards and active Sephadex G-50 fractions from patients 1-3. Estimations of molecular weight ranged from 14,000-16,500 for patient 1, from 14,000-17,000 for patient 2, and from 16,000-18,000 for patient 3.

Thus, it is seen that at least one protein which suppresses the follicle response to gonadotropins is secreted by the preovulatory ovary. Specifically, a heat- and trypsin-labile substance is secreted directly into the venous drainage from the ovary containing the dominant follicle which suppresses the follicular response to gonadotropins. That this protein is not secreted in large amounts by anovulatory ovaries was evidenced by the failure of the bioassay to detect inhibitory activity in the venous drainage of the contralateral ovary of patients 1-3 as well as the ovarian venous effluents from three anovulatory women. This potential intra- and/or interovarian regulator of folliculogenesis mediates dominance of the preovulatory follicle by an active process, such that after the selection of the dominant follicle, the gonadotropin responsivity of other follicles on the same and contralateral ovaries is suppressed.

Example Two

Identification of Follicular Regulatory Protein(s) in Pooled Human Follicular Fluid To evaluate the role of nonsteroidal, follicular fluid proteins in folliculogenesis, the 10-55% saturated ammonium sulfate fraction of pooled human follicular fluid was dialyzed against 0.025M Tris/HCl (pH 7.5) using 10,000 molecular weight exclusion membranes, then passed through agarose immobilized textile dye. Activity was determined by test fraction inhibition of human menopausal gonadotropin (2 U human LH/FSH day) induced ovarian weight gain, and serum estradiol increase in hypophysectomized, diethylstilbesterol-treated, twenty-five-day-old female rats.

Specifically, human follicular fluid was aspirated from regularly menstruating women (aged twenty-five to thirty-five years) undergoing ovarian hyperstimulation during participation in an in vitro fertilization protocol by treatment with clomiphene citrate (150 mg/day for five days, beginning three-eight days after onset of spontaneously occurring menses) and hCG (5000 IU forty-eight hours before aspiration). Sera were collected daily and estrogen concentrations were determined. When serum estrogen concentrations exceeded 800 pg/ml, patients underwent laparoscopy for aspiration of follicles in excess of 20 mm in diameter. The follicular aspirate was immediately centrifuged (800×g), the granulosa cells were removed and the aspirate was then frozen (−57° C.). Follicular aspirates from twenty such patients were pooled and provided the hFF used throughout this study.

Pooled hFF was slowly thawed and fractionated by dropwise addition of an equal volume of saturated ammonium sulfate (SAS) during persistent agitation at 4° C. After a twelve hour incubation at 4° C., the precipitate was pelleted, the supernatant was discarded, and the pellet was resuspended (2:1, vol/vol) with 10% SAS. An additional twelve hours of agitation was followed by centrifugation at 3,000 ×g for thirty minutes. The resulting supernatant was dialyzed using 10,000 molecular weight exclusion dialysis membranes against three changes of 0.025M Tris/HCl, pH 7.5, (buffer A) for sixteen hours. Insoluble material was removed from the retentate by centrifugation (3,000×g for 30 minutes).

A series of agarose (triazine ring) immobilized textile dyes (Dye-Matrix Screening Kit, Amicon, Lexicton, Mass.) were prepared according to the manufacturer's instructions. Columns (9×32 mm, 2 ml bed volume) containing Matrix Gel Blue A (triozinyl dye Cibacron Blue 3GA), Red A (Procion Red HE3B), Blue B (Cibacron Brilliant Blue FBR-P), Orange A, or Green A were equilibrated with 20 mM Tris/HCl (pH 7.5), then charged with 0.5 ml aliquots of the dialyzed retentate. Unbound material was eluted with 10 ml buffer A. The bound protein was eluted with 1.5M KCl in buffer A. Eluent fractions were dialyzed overnight against buffer A, and protein concentration determined.

Eluents containing active material (Orange A-bound fractions) were further separated (10 ml/h, 4° C.) on a Sephadex G-50 (superfine) column (1.6×50 cm, $V_O$=60 ml, 5 ml/h, 4° C.) with buffer A. Elution profiles were determined using an ISCO absorbance meter at 254 nm. For estimation of molecular weight by gel filtration, the same Sephadex G-50 column used for purification (2.6×70 cm, $V_t$=280, $V_O$=90 ml) was equilibrated and developed with molecular weight standards ribonuclease-A, chymotrypsin, and ovalbumin in buffer A at 10 ml/h, 4° C. Fractions were then assessed for activity in the bioassay. $K_{av}$ for each standard and active fraction was calculated using $V_t$=280, $V_O$=90 ($K_{av}=V_e-V_O/V_t-V_O$).

Additional aliquots from the 10-55% SAS fraction of the hFF (10 ml) were passed through a Concanavalin A-linked Sepharose 4B (Con A) column which was washed with 5 vol of 0.2M NaCl, 0.05M Tris/HCl (pH 7.4), then further eluted with 0.2M α-methyl-D-mannoside in buffer A at a flow rate of 20 ml/h. Both Con A-bound and -unbound fractions were assessed for activity in the bioassay. Chromatography fractions containing inhibitory activity were heated (56° C., 1 h) or trypsin digested (10 mg/100 ml) for three hours, and then retested for bioactivity.

Both Orange A-bound and 10–55% SAS hFF were further purified by isoelectric focusing using a Sephadex G-15 support matrix. The apparatus consisted of a 4×30 cm water-jacketed glass column containing a 2.5×20 cm G-15 Sephadex bed supported by a 2.5×8 cm Teflon elution plug under a 25-m Millipore filter. The column was previously equilibrated with two-bed volumes of a solution containing carrier ampholytes (4% of pH 3–10 and 4% of pH 2–4) in 12.5% glycerol. Cytochrome C was used as an internal marker protein (pI=10.5). The fractions were then washed into the column with 20 ml ampholyte-glycerol solution. A second Millipore filter was placed on the top of the Sephadex bed. A 10-ml polyacrylamide solution of 14% acrylamide, 0.3% Bis, and 50 µl N,N,N',n'-tetramethylethylenediamine (polymerized by the addition of 0.1 ml of 10% ammonium persulfate) was then poured over the filter. Upon completion of polymerization (twenty minutes), the column was inverted, the Teflon plug was removed, and a second acrylamide plug was layered over the bottom filter. After polymerization of the bottom plug, the column was returned to its upright position and lowered into anode buffer containing 1% sulfuric acid. The remaining upper portion of the column was filled with 1% ethanolamine. The column was cooled by recirculating water at 1°–4° C. throughout the procedure. Isoelectric focusing was initiated at 800 constant V (16 mA) and allowed to proceed to equilibrium as monitored by an eventual decline in the milliamperage to 2.5 mA (8–12 h). Thereafter, pooled column fractions (3 ml) were dialyzed against buffer A to remove ampholytes before bioassay.

Since an apparent isoelectric point was reproducibly determined in material isolated from the human ovarian vein blood by ampholyte displacement chromatograph in Example One, this procedure was employed with the 10–55% SAS-dialyzed hFF. Pooled aliquots (10 ml) were layered onto a Polybuffer Exchanger 94 adjusted to pH 7.4 with 0.025M Imidazole buffer, 10 ml/h, 4° C. The column was eluted with Polybuffer 74 adjusted to pH 4.0 with 1N HCl. Fractions that eluted at a pH greater than 7.4 were collected and rechromatographed in the same Pharmalyte column reequilibrated to pH 9.4 with ethanolamine 0.025M, and eluted with Polybuffer 96 TM adjusted to pH 6.0 with 1N KOH.

The rats used in the bioassay were hypophysectomized and implanted as described in Example One, and serum estradiol-17β concentration was determined as described previously.

Control determinations (no injected test fractions) for unstimulated ovarian weight were 34.7±3.2 (SEM) mg/rat and for LH-FSH-stimulated were 192.0±30.5 mg/rat. Control levels of trunk serum estradiol were 12.5±0.7 pg/ml for unstimulated rats, and 118.5±21 pg/ml for LH-FSH-stimulated. Where indicated, 100% inhibition equals ovarian weight and/or serum estradiol concentration of mean unstimulated control values. Zero percent inhibition equals ovarian weight or serum estradiol concentration of LH-FSH-stimulated control rats. These results are similar to those which have been obtained with the previous application of this bioassay procedure in Example One. Tests of statistical significance were performed by Student's t test and Duncan's multiple range analysis.

Protein separation was performed using a Waters HPLC/GPC Model 244 Liquid Chromatograph equipped with a 0.75×50 cm TSK 3000 SW gel exclusion column. A 100Ml aliquot of the dialyzed, Orange A-dye-matrix eluent was separated on each high performance liquid chromatographic (HPLC) run. The proteins were eluted from the TSK column using an isocratic gradient of 0.02M PBS (pH 7.0) at a flow of 0.5 ml/min. The protein peaks were detected by absorbance at 280 nm with a Waters variable wavelength detector (Model M-450) and molecular weight estimates of the specific follicular fluid proteins were performed using highly purified molecular weight chromatography standards of ribonuclease-A, chymotrypsin, ovalbumin, and bovine serum albumin (BSA).

Figure 5:
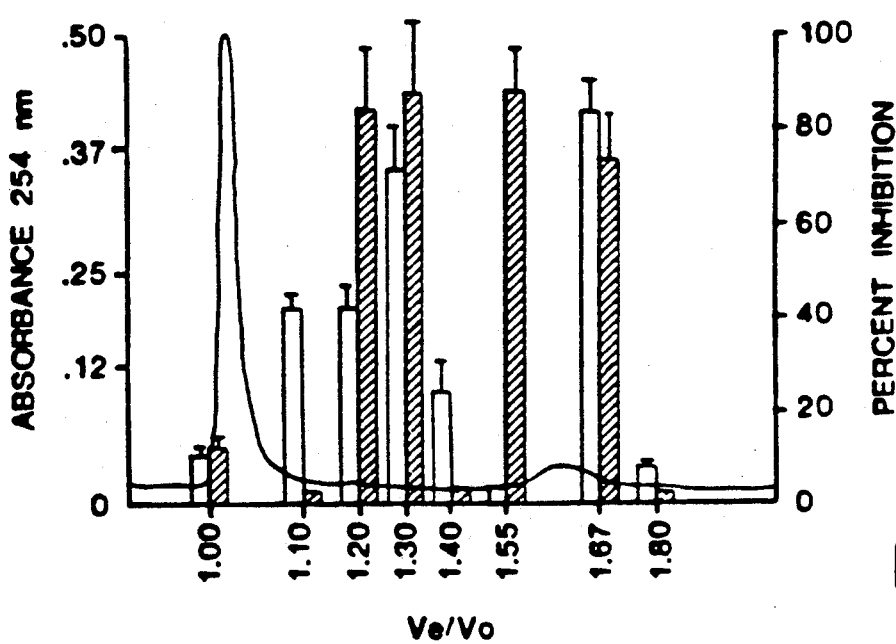
FIG. 5: shows an elution profile of the 10-55% SAS cut of human follicular fluid, dialyzed and developed through Orange A Dye-Matrix (1.5M KCl), passed through Sephadex G-50. Fractions (2 ml) were tested in the LH-FSH-stimulated hypophysectomized, immature, DES-treated rat for inhibition of ovarian weight, and serum estradiol concentration (mean±SEM). Fractions with molecular weight corresponding to 12,000-18,000 contained inhibitory activity.

FIG. 5 depicts the chromatographic elution profile of hFF developed through Sephadex G-50 at 254 nm after SAS 10–55% cut, dialysis (<10,000 molecular weight), and elution of Orange A-bound material with 1.5M KCl. Fractions (2 ml) were tested in the LH-FSH-stimulated hypophysectomized, immature, DES-treated rat for inhibition of ovarian weight, and serum estradiol concentration (mean±SEM). An initial peak in absorbance can be seen at $V_e$-$V_0$ ratio of 1.0–1.1, which after descending, reaches a gradual ascending second plateau ($V_e$-$V_0$ of 1.58–1.68). Biological activity was determined as inhibition of ovarian weight and trunk serum estradiol levels. The same column was then equilibrated with molecular weight standards and developed with buffer A, allowing for molecular weight estimation ($K_{av}$=log $V_e$-$V_0$/$V_t$-$V0$) for fractions containing inhibitory activity. Molecular weight of eluents containing inhibitory activity was estimated to be 13,000–18,000.

Figure 6:
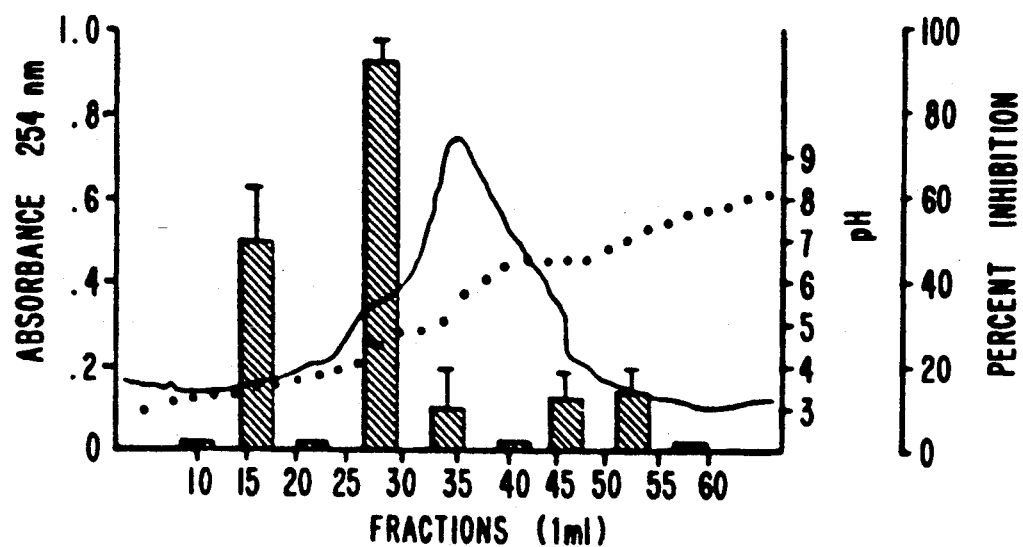
FIG. 6. Isoelectric focusing chromatogram of pooled human follicular fluid after SAS precipitation (10-55%), dialysis and Orange A Dye-Matrix chromatography (0.5M KCl eluent). Fractions corresponding to an isoelectric point of pH 3.5-4.5 contained inhibitory activity of rat ovarian weight and trunk estradiol (not shown) in the bioassay after gonadotropin challenge.
Figure 7:
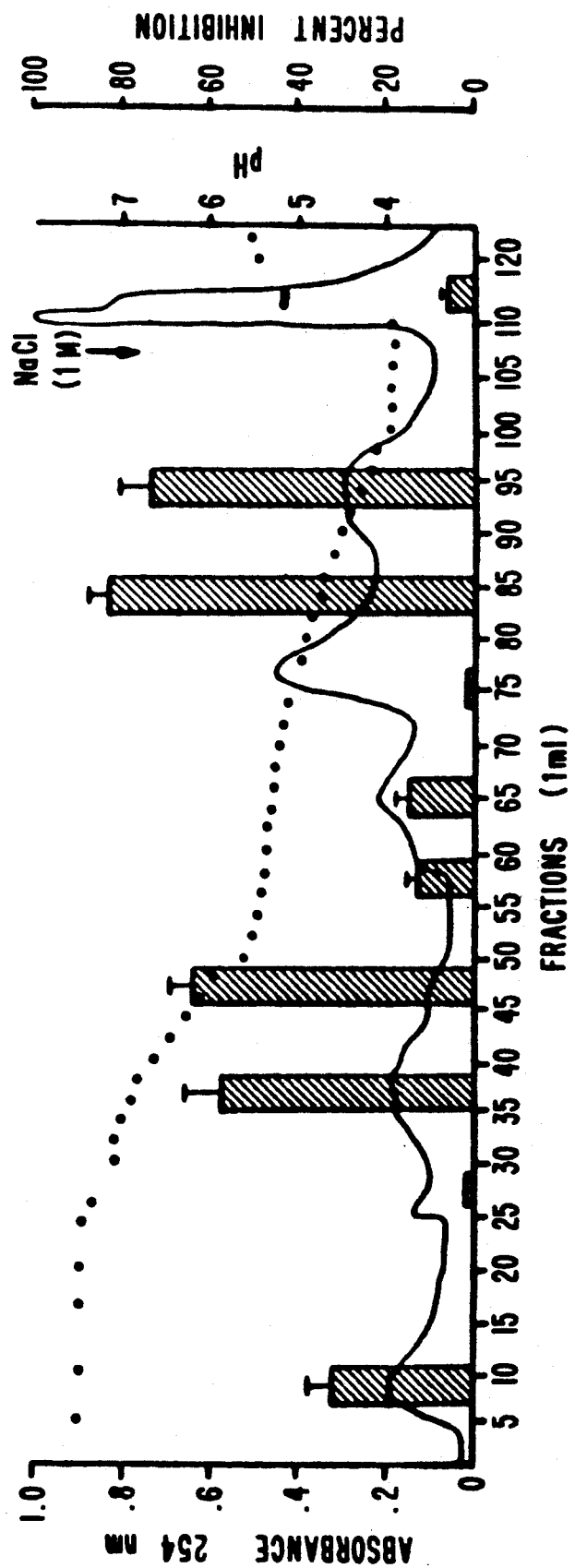
FIG. 7: Ampholyte displacement chromatogram of pooled human follicular fluid (hFF) after SAS precipitation (10-55%), dialysis (10,000 molecular weight) and Orange A Dye-Matrix chromatography (1.5M KCl eluent). Fractions corresponding to an isoelectric point of pH 3.5-4.5 and pH 6.5-7.0 contained inhibition of rat ovarian weight (mean±SEM) in the bioassay after gonadotropin challenge.

Eluents from the isoelectric focusing of hFF after SAS (10–55%), dialysis and Orange A dye matrix chromatography (1.5M KCl eluate) (FIG. 6) were evaluated for activity in the bioassay. Only fractions in the pH range of 3.5–4.5 contained clear inhibition of ovarian weight and trunk 17β-estradiol levels (not shown). When isoelectric point determination was performed using ampholyte displacement chromatography (FIG. 7), inhibition of rat ovarian weight was found in the pH range 3.5–4.5. In addition, a second area of inhibition in the bioassay was noted at (pH 6.0–6.5.).

Figure 8:
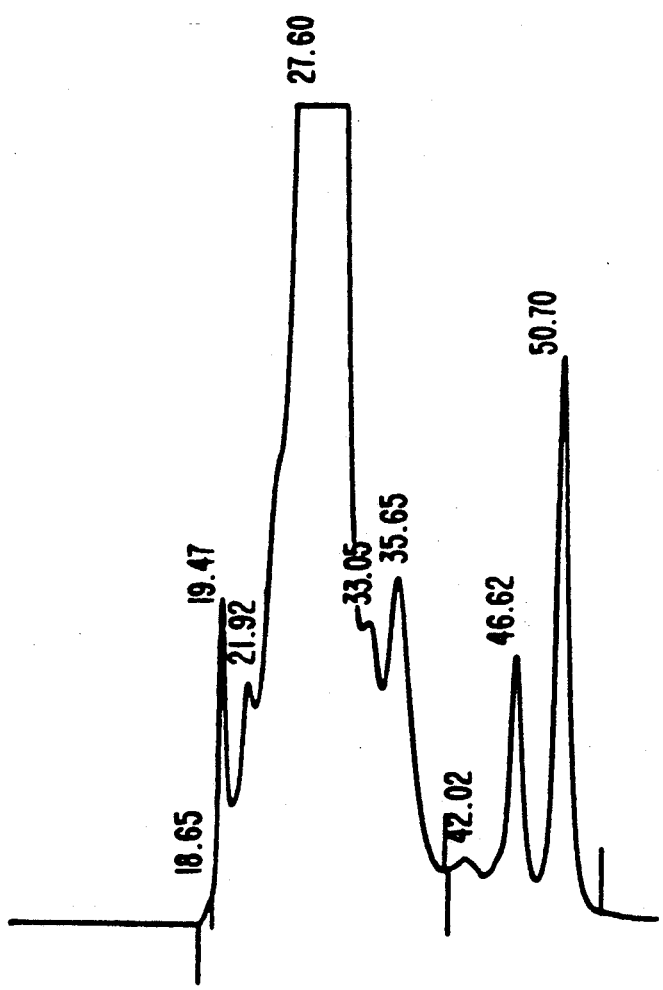
FIG. 8: Representative high performance size exclusion liquid chromatogram (TSK 3000 analytical column) of the Orange A-bound fraction of the 10-55% SAS hFF. Fractional retention times corresponded to the following approximate molecular weight ranges: 21.0-23.0 minute, >100,000; 23.0-25.0 minutes, 100,000; 25.0-28.5 minutes, 70,000-100,000; 28.5-32.2 minutes, 40,000-70,000; 32.2-34.0 minutes, 30,000-40,000; 34.0-40.0 minutes, 18,000-30,000; 40.0-45.0 minutes, 5.500-18,000; 45.0-49.0 minutes, 2,500-5,000; 49.0-53.0 minutes, <2,500.
Figure 9:
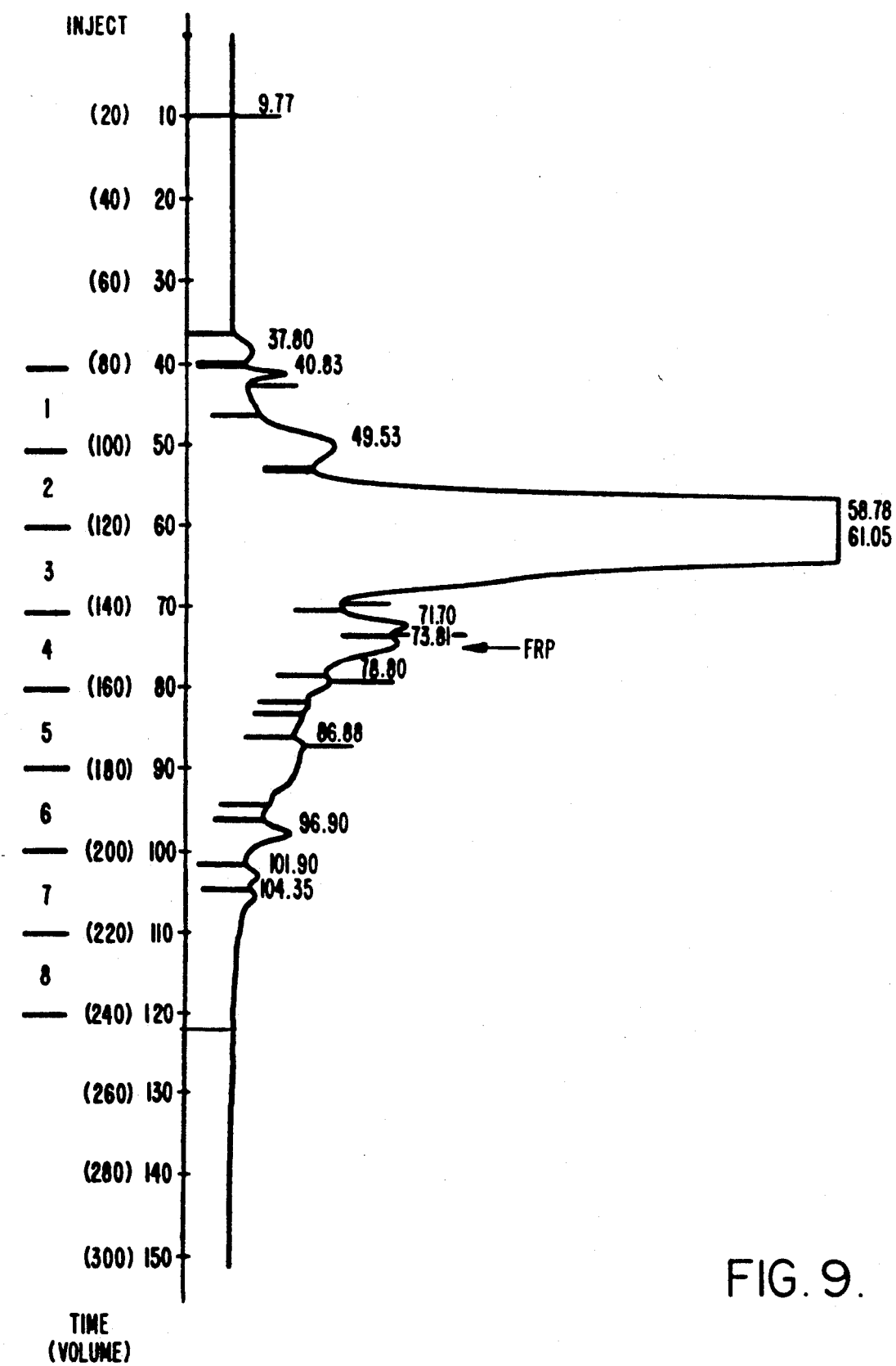
FIG. 9: Representative high performance liquid chromatogram (TSK 3000 preparative molecular weight exclusion column) of the 10-55% SAS fraction of human follicular fluid (hFF).

FIG. 8 depicts the HPCL elution profile of the Orange A-bound extracted hFF material eluted through a TSK 3000 analytical molecular weight exclusion column. FIG. 9 indicates the elution profile of the same material eluted through a TSK 3000 preparative molecular weight exclusion column. Each of these elution profiles displays unique chromatographic patterns of FRP.

In FIG. 8, the HPLC eluent was divided into ten fractions based on peak absorbances [0: 18.5–21.0 minutes (void volume); 1: 21.0–23.0 minutes; 2: 23.0–25.0 minutes; 3: 25.0–28.5 minutes; 4: 28.5–32.2 minutes; 5: 32.2–34.0 minutes; 6: 34.0–40.0 minutes; 7: 40.0–45.0 minutes; 8: 45.0–49.0 minutes; 9: 49.0–53.0 minutes]. Aromatase inhibiting activity elutes at 40–45 minutes. These fractions corresponded to the following molecular weight ranges: 1, 100,000; 2, 100,000; 3, 70,000–100,000; 7: 5,500–18,000; 8: 2,500–5,500; 9, 2,500. The retention times of peak absorbances after HPLC elution, when correlated to molecular weight standards, were highly reproducible (13 runs).

Figure 10:
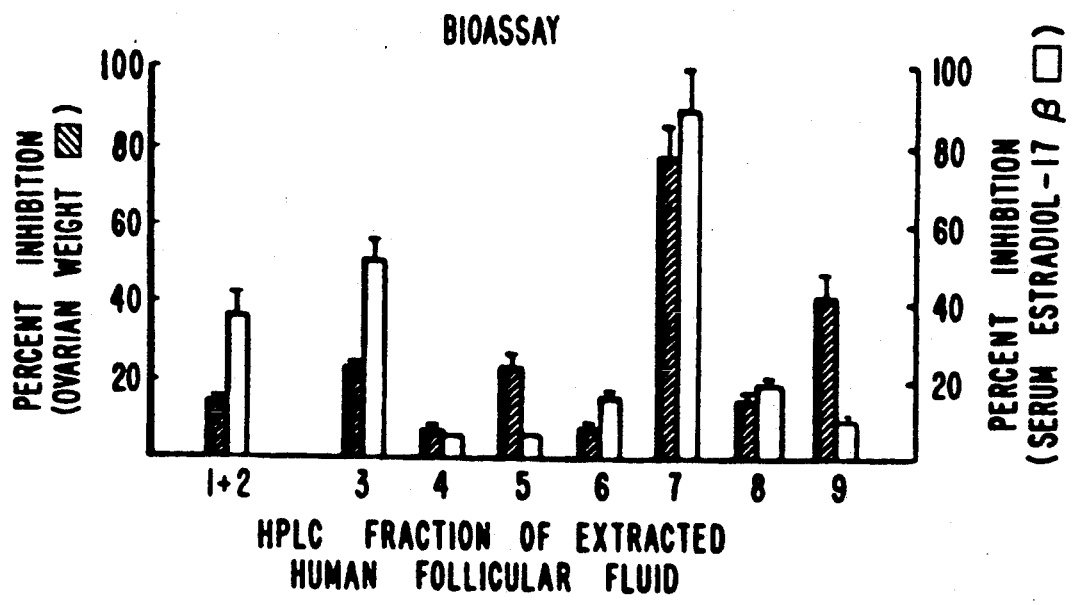
FIG. 10: Bioassay results of HPLC fraction of Orange A bound hFF. Inhibition of LH-FSH-induced ovarian weight augmentation in immature, hypophysectomized, DES-treated rats (mean±SEM) was evident in those treated with the 5,500-18,000 molecular weight fractions (no. 7, n=3 rats at each level).

When HPLC fractions were tested in the bioassay (see FIG. 10), inhibition of ovarian weight gain and serum estradiol elevation were evident in rats injected with the 5,500–18,000 molecular weight fraction

Figure 11:
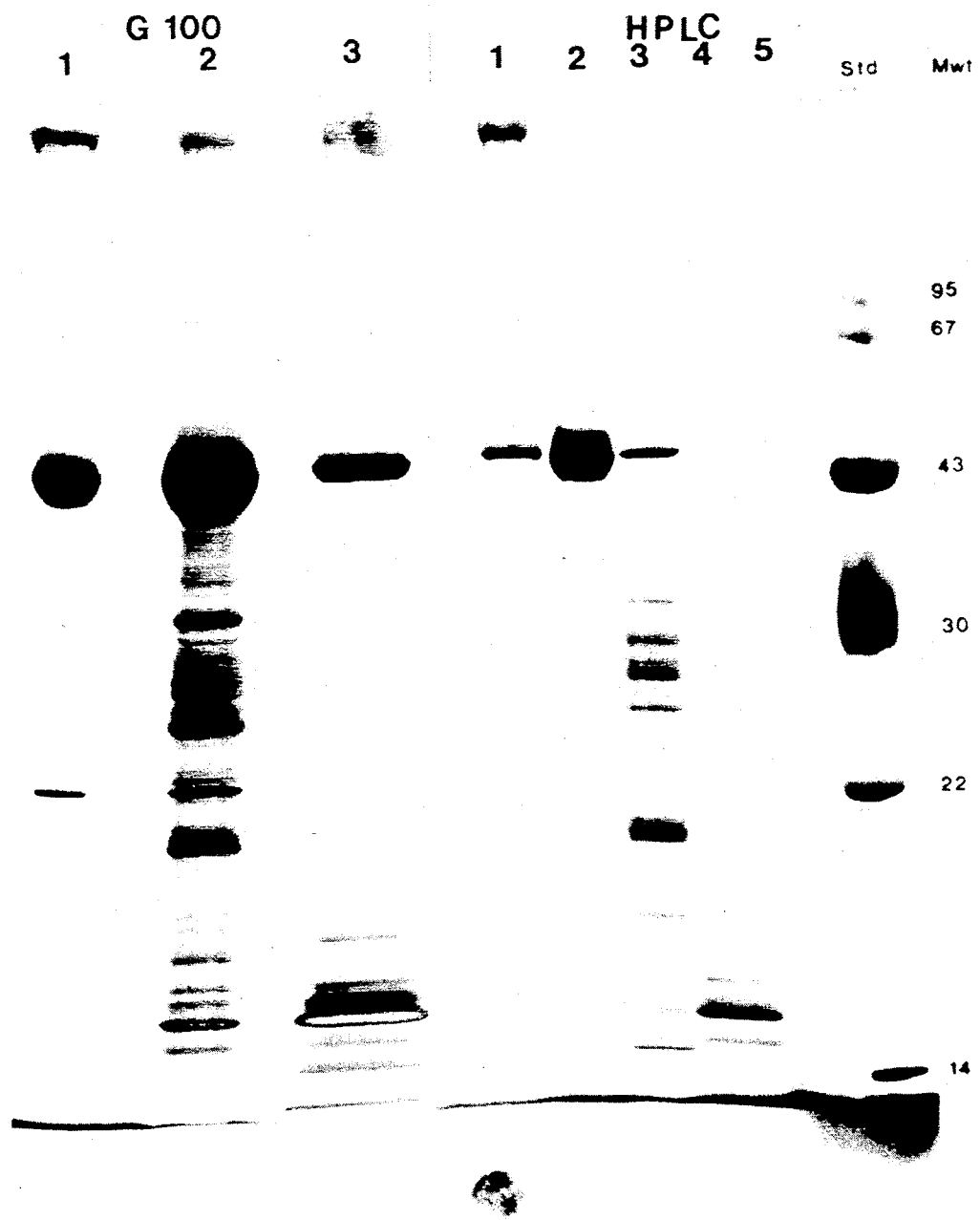
FIG. 11: A polyacrylamide gel, with sodium dodecyl sulfate, of the fractions shown in FIG. 8 after HPLC.

[78±8% (SEM) and 89±10%, respectively (P<0.01)] as compared to the other fractions. FIG. 11 shows a polyacrylamide gel, with sodium dodecyl sulfate, of the fractions shown in FIG. 8 after HPLC. Columns 1-5 in FIG. 11 correspond, respectively, to the columns 3-7 in FIG. 8. The FRP is shown at the bottom of column 5, with a molecular weight of 15,000 to 16,000 when compared to the molecular weight standards to the right of column 5. The standards include ribonuclease A at 14,000, and chymotripsinogen A at 22,000.

In Example One, there is described a protein, in the venous drainage of the human ovary which contains the preovulatory follicle, which suppresses the follicular response to gonadotropins. That this protein was not secreted in large amounts by anovulatory ovaries was evidenced by failure of the bioassay to detect inhibitory activity in the venous drainage of the contralateral ovary in ovulatory patients as well as both ovarian vein effluents from anovulatory women. In the present example, a comparable isolation procedure has shown a similar biological activity in human follicular fluid (hFF). The rat bioassay employed to identify material in hFF which inhibits LH-FSH-mediated follicular stimulation was the same as that reported for human ovarian vein blood extracts. Follicular inhibitory activity in hFF had a molecular weight, determined by HPLC size exclusion chromatography (10,000-18,000) that is similar to that of follicular inhibitory activity recovered from human ovarian vein serum (14,000-17,000). The indicated isoelectric point for inhibitory activity in human ovarian vein extract, as determined by chromatofocusing (pH 5.8-6.4), is similar to the hFF extract reported here.

The follicular inhibitory substance reported here was derived from follicular aspirates of women during spontaneous ovarian cycles whose follicles were hyperstimulated by clomiphene and hCG therapy. Consequently, no conclusion can be drawn regarding this material in normally developing follicles. However, since a similar activity has been identified in the ovarian vein serum draining the spontaneous preovulatory ovary (Example One) these data indicate this inhibitory protein to be a product of the dominant follicle itself.

Example Three

Gonadal Regulatory Protein Fractions in Porcine Follicular Fluid

Example Two details the isolation of a protein fraction (FRP) from human follicular fluid, which suppresses follicular response to gonadotropins. The present example employs an identical isolation, bioassay and HPLC procedures with respect to porcine follicular fluid (pFF). Isoelectric focusing demonstrated inhibitory activity at about pH 4.2-4.5 and pH 6.27 and peak activity was found in the molecular weight range 12,000-18,000 daltors.

Granulosa cells were isolated from rat ovaries and FSH binding was determined by the procedure of Erickson, as described in Example Four. Aromatase activity of the rat granulosa cells was determined in a procedure similar to that described therein.

Figure 14:
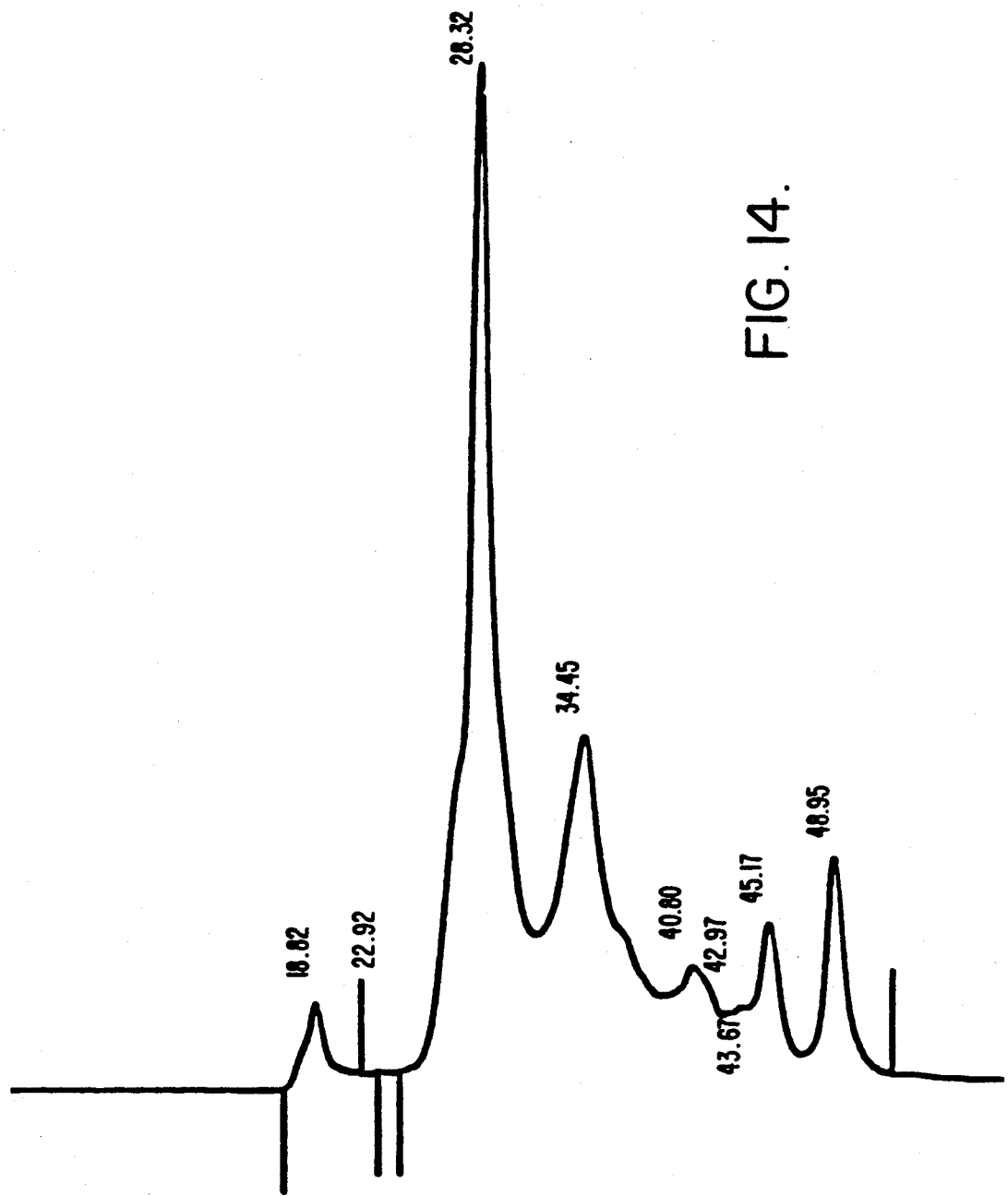
FIG. 14: High performance liquid chromatogram (gel permeation) of the Orange A-bound fraction of 10-55% saturated ammonium sulfate of porcine follicular fluid recovered from Sephadex G100 elution (Ve/Vo 1.3-1.7) Retention times corresponded to the following approximate molecular weight ranges: 8 min: 100,000-74,000; 8-31 min: 74,000-36,000; 31-36 min: 36,000-18,000; 36-39 min: 18,000-12,000; 39-43 min: 12,000-5,800.

FIG. 14 depicts the chromatographic elution profile of pFF at 280 nm developed through Sephadex G-100 following the 10-55% SAS cut, dialysis, and elution of Orange A-bound material with 1.5M KCl. An initial peak can be seen at a $V_e/V_o$ of 1.1 to 1.17, thereafter trailing, followed by a gradual ascending second plateau at $V_e/V_o$ 1.7 to 1.9. When biological activity was assessed in the HIFR-hMG bioassay, 95% inhibition of both ovarian weight and trunk serum estradiol-17-B levels were found at $V_e/V_o$ of 1.5. The same column was then equilibrated with molecular weight standards and developed with 0.025M PBS, pH 7.4, allowing for estimation of the $K_{av}$ ($V_o-V_e/V_e-V_o$) of fractions containing inhibitory activity.

Figure 12:
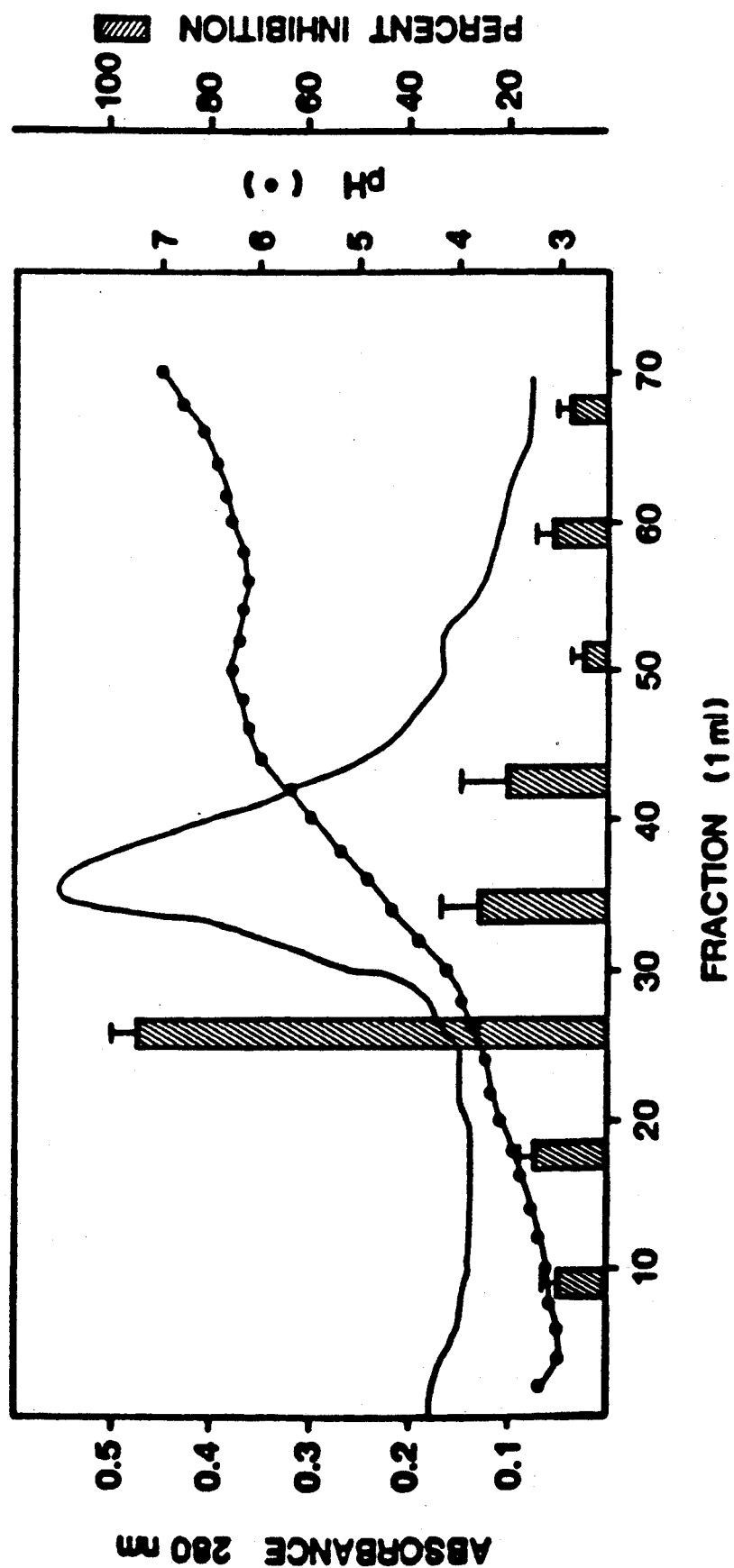
FIG. 12: Isoelectric focusing chromatogram of dialyzed (10,000 mw), 10-55% saturated ammonium sulfate fraction of pooled porcine follicular fluid (5 ml) after elution (0.5M KCl) from an Orange A dye matrix column. Maximum ovarian weight inhibition (hatched bars) in immature, hypophysectomized, DES-treated rats by eluent fractions were found in the 3.7-4.5 pH range ($\overline{X}$+SEM of rats/fraction).
Figure 13A:
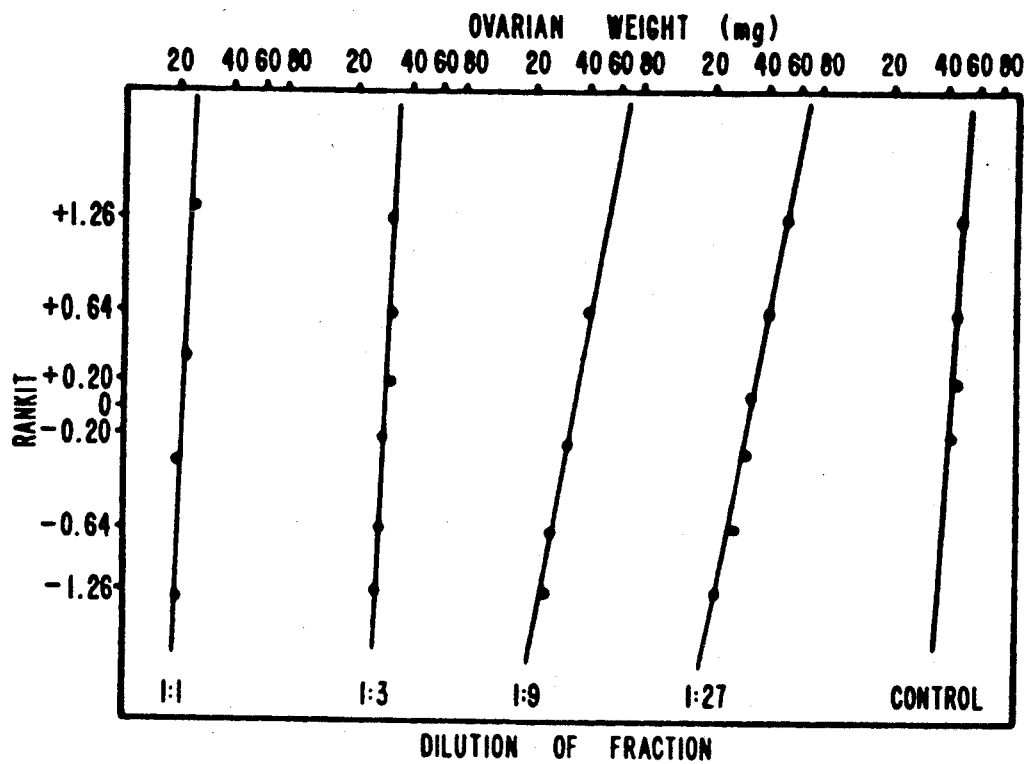
FIG. 13a shows Rankit analysis of ovarian weights from dilutions tested, the O intercept of which was plotted on the dose response curve.
Figure 13B:
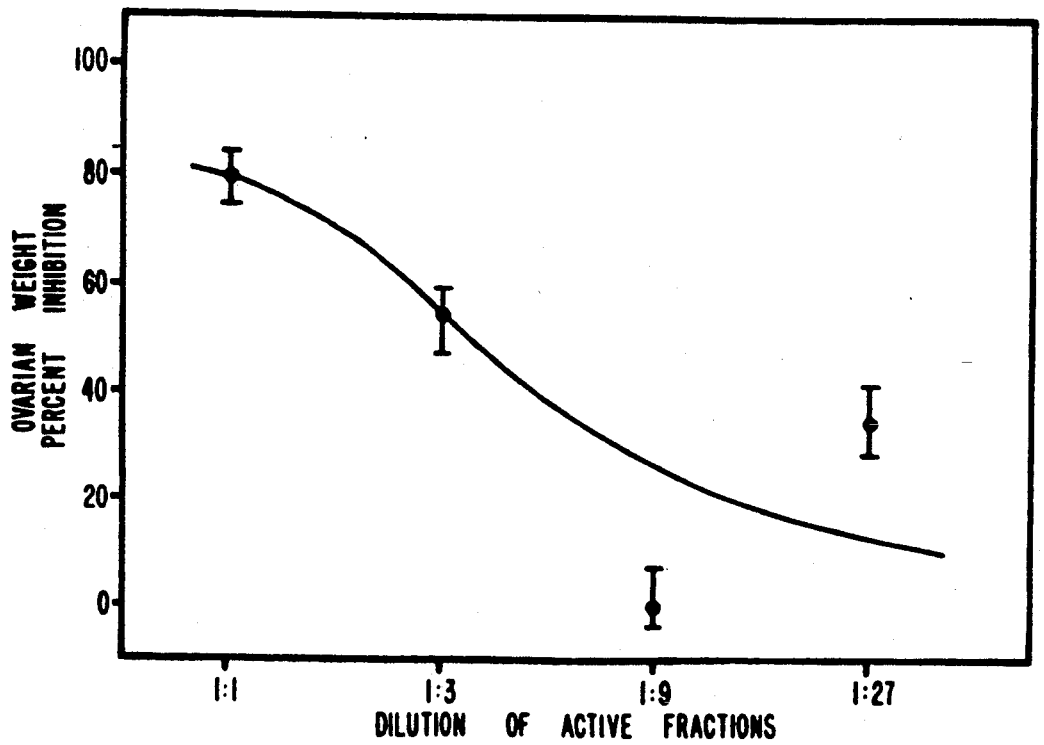
FIG. 13b shows the Dose response relationship: porcine follicular fluid fractions which contained inhibitory activity in the rat ovarian weight augmentation bioassay recovered from isoelectric focusing (ph 4.0-4.5) after Orange A Dye Matrix elution (0.5M KCl) and dialysis (10,000 mw) of 10-55% saturated ammonium sulfate.

When eluents from the isoelectric focusing (IEF) of the Orange A bound pFF extraction (FIG. 12) were evaluated for bioactivity by rat bioassay, only fractions within the range of pH 3.7 to 4.0 contained obvious inhibition of both rat ovarian weight response and trunk serum estradiol-17B levels (83.6±9.4% and 47.2% respectively). Serial dilutions of the extracted PFF fractions eluted from the Orange A dye-matrix with 1.5M KCl recovered from the isoelectric focusing column were tested for activity in the hypophysectomized immature DES-treated female (HIFR-rat) bioassay. A dose response relationship was apparent (FIG. 13) with fractions in the pH 3.5-4.0 range, while other pH ranges from the IEF column were without inhibitory activity.

Figure 15:
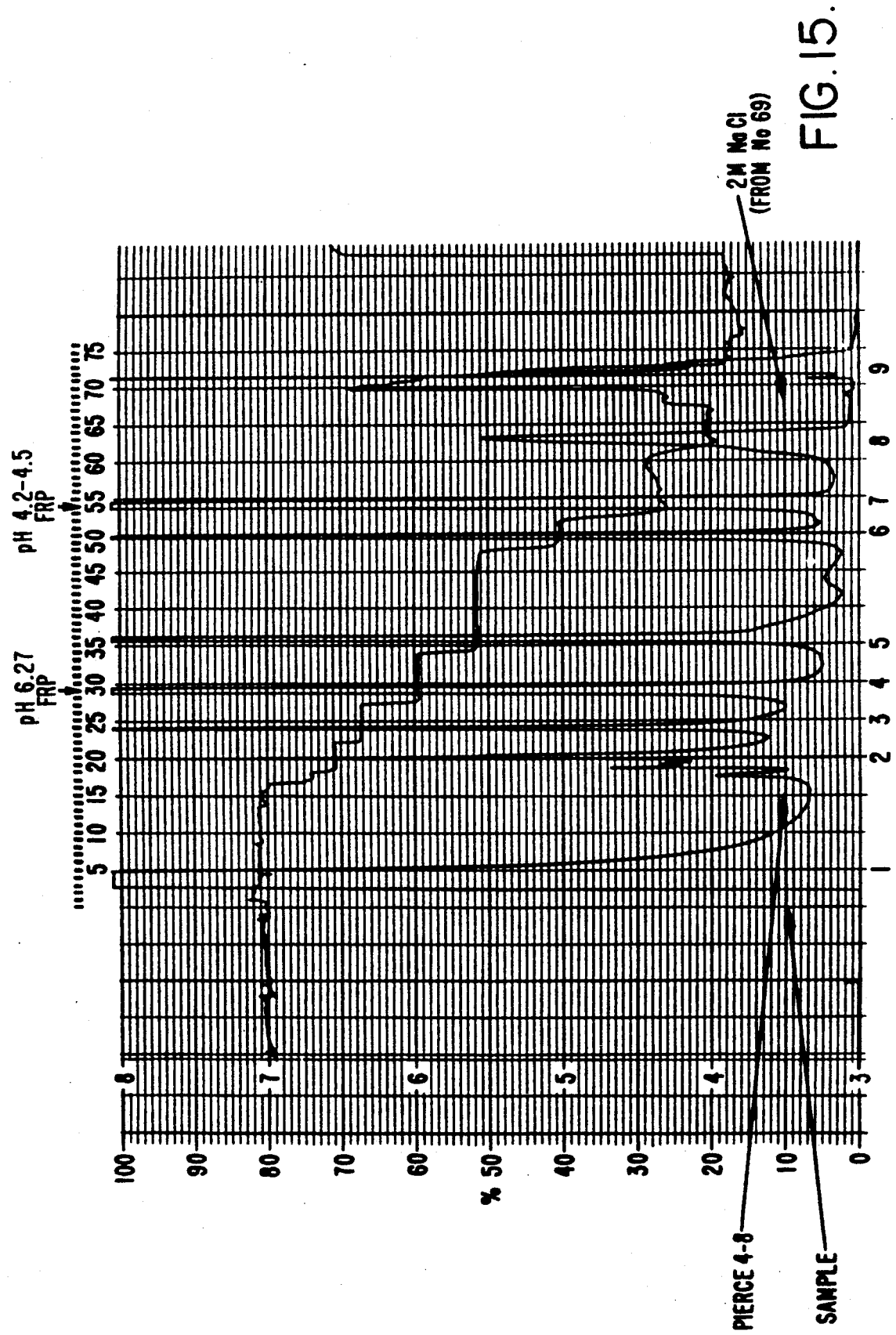
FIG. 15: Chromatofocusing by hydrogen ion exchange chromatography of the Orange A-bound fraction of the 10-55% saturated ammonium sulfate fraction of porcine follicular fluid.

When aliquots of this Orange A matrix column were separated by hydrogen ion chromatography (chromatofocusing), fractions corresponding to pH 4.0-4.5 (FIG. 15, fraction 7) and pH 6.0-6.5 (FIG. 15, fraction 4) inhibited microsomal aromatase activity. When fractions 4 and 7 are further purified by HPLC molecular weight separation, aromatase inhibitory activity (FRP) is present in the fractions corresponding to 15,000-16,000 daltons.

When aliquots from the ammonium sulfate 10-55% cut eluted from the Orange A dye matrix were passed through Concanvalin-linked Sepharose 4B (eluted 3×Vo with PBS followed by 0.2M alpha-methyl mannoside), no inhibitory activity in the rat bioassay was noted in the Con A bound fraction (i.e. eluted with mannoside) with only marginal recovery of activity (20-30% inhibition of ovarian weight response) in the material eluted in the unbound PBS fraction (data not shown).

Figure 16:
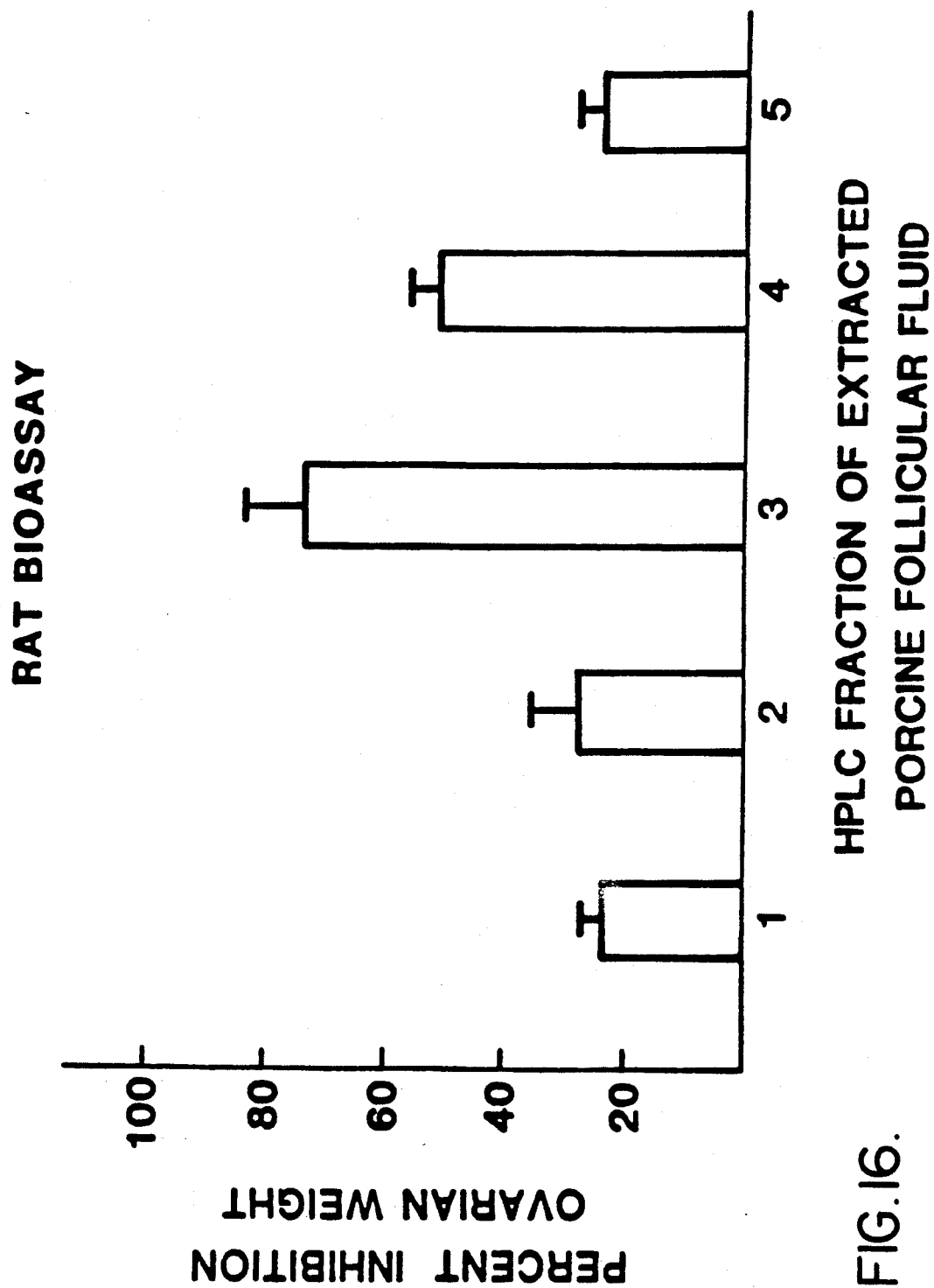
FIG. 16: Bioassay results of high performance liquid chromatography fraction of Orange A-bound porcine follicular fluid after separation by Sephadex G-100 chromatography (Ve/Vo 1.3-1.7). Inhibition of LH/FSH induced ovarian weight augmentation (X±SEM) in immature, hypophysectomized, DES-treated rats (n=6/fraction tested) was measured after treatment with 2 ml of HPLC eluents which corresponded to the following approximate molecular weights: 1: 100,000-74,000; 2: 74,000-36,000; 3: 36,000-18,000; 4: 18,000-12,000; 5: 12,000-5,800.

FIG. 16 depicts the HPLC elution profile of the Orange A-bound extracted PFF material after separation through the Sephadex G-100 column ($V_e/V_o$ 1.3-1.7). The HPLC eluent was divided into five fractions based on peak absorbances (1: retention time—25-.0-27.8 minutes; 2: 27.8-31.0 minutes; 3: 31.0-36.0 minutes; 4: 36.0-39.0 minutes; 5: 39.0-43.0 minutes). These fractions corresponded to the following molecular weight ranges: 1: 100,000-74,000; 2: 74,000-36,000; 3: 36,000-18,000; 4: 18,000-12,000; 5: 12,000-5,800. The retention times of peak absorbances after HPLC elution, when correlated to molecular weight standards, were highly reproducible (five runs).

Figure 17:
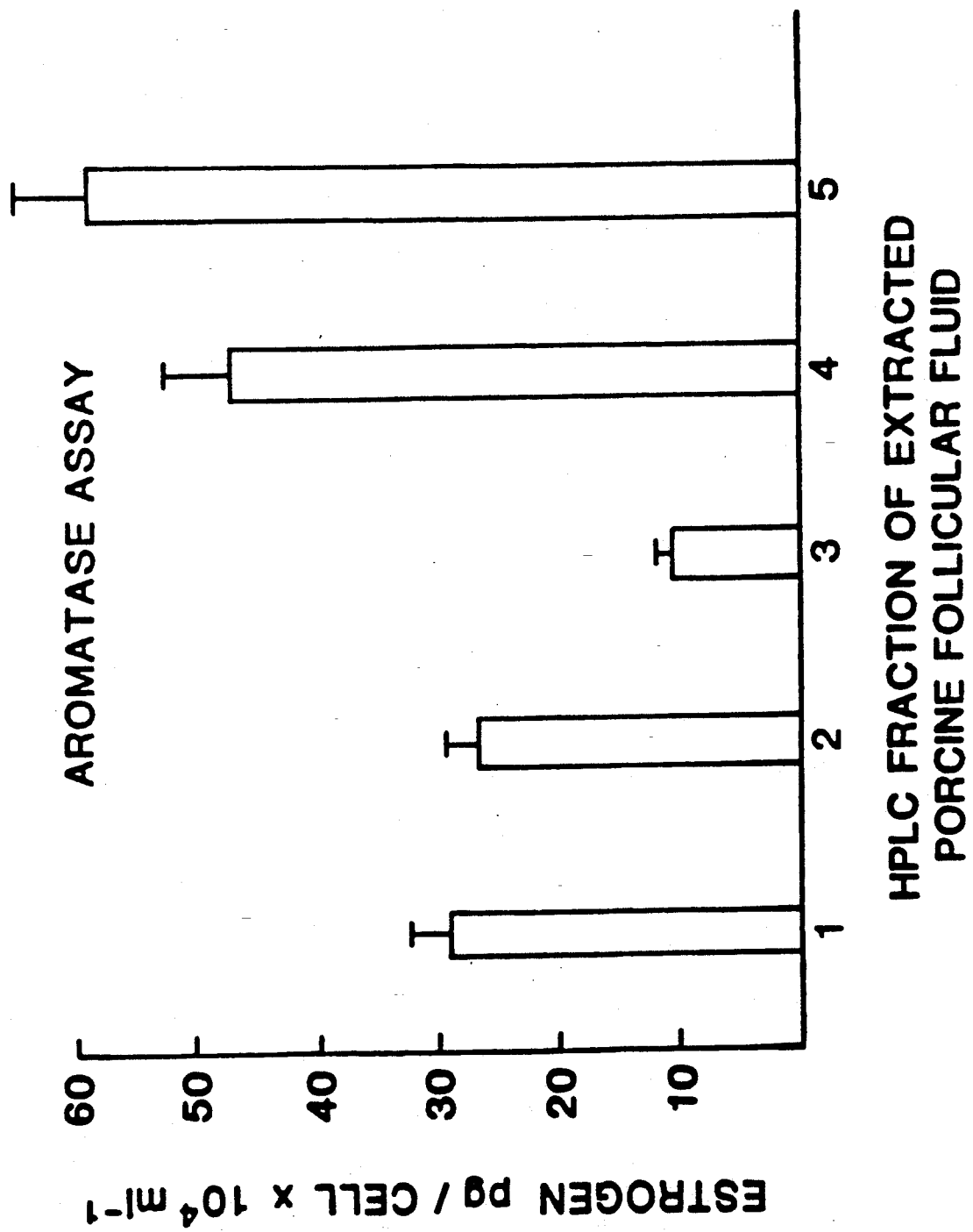
FIG. 17: Aromatase activity of rat granulosa cells derived from immature, hypophysectomized, DES-treated rats (n=6/fraction tested) which received LH/FSH stimulation and injection of high performance liquid chromatography fractions (2 ml) of extracted porcine follicular fluid (X±SEM). HPLC fractions corresponded to the following approximate molecular weights: 1: 100,000-74,000; 2: 74,000-36,000; 3: 36,000-18,000; 4: 18,000-12,000; 5: 12,000-5,800.

When HPLC fractions were tested in the bioassay (see FIG. 17), inhibition of ovarian weight gain was evident in rats injected with fraction 3 (74±8%; p<0.01) and fraction 4 (51±9%, p<0.05) as compared to the other three fractions. Inhibition of androstenedione conversion to total immunoreactive estrogen by granulosa cells harvested from the HPLC-fraction treated rat's ovaries (n=6 ovaries/HPLC fraction) was evident in HPLC fraction 3 (11.1±3 pg/10,000 cells/ml). When no test fractions were injected into the HIFR-hMG bioassay rat prior to the aromatase assay, a range of 30-60 pg of total immunoreactive estrogen/10,000 cells/ml was present in the control incubates.

Figure 18:
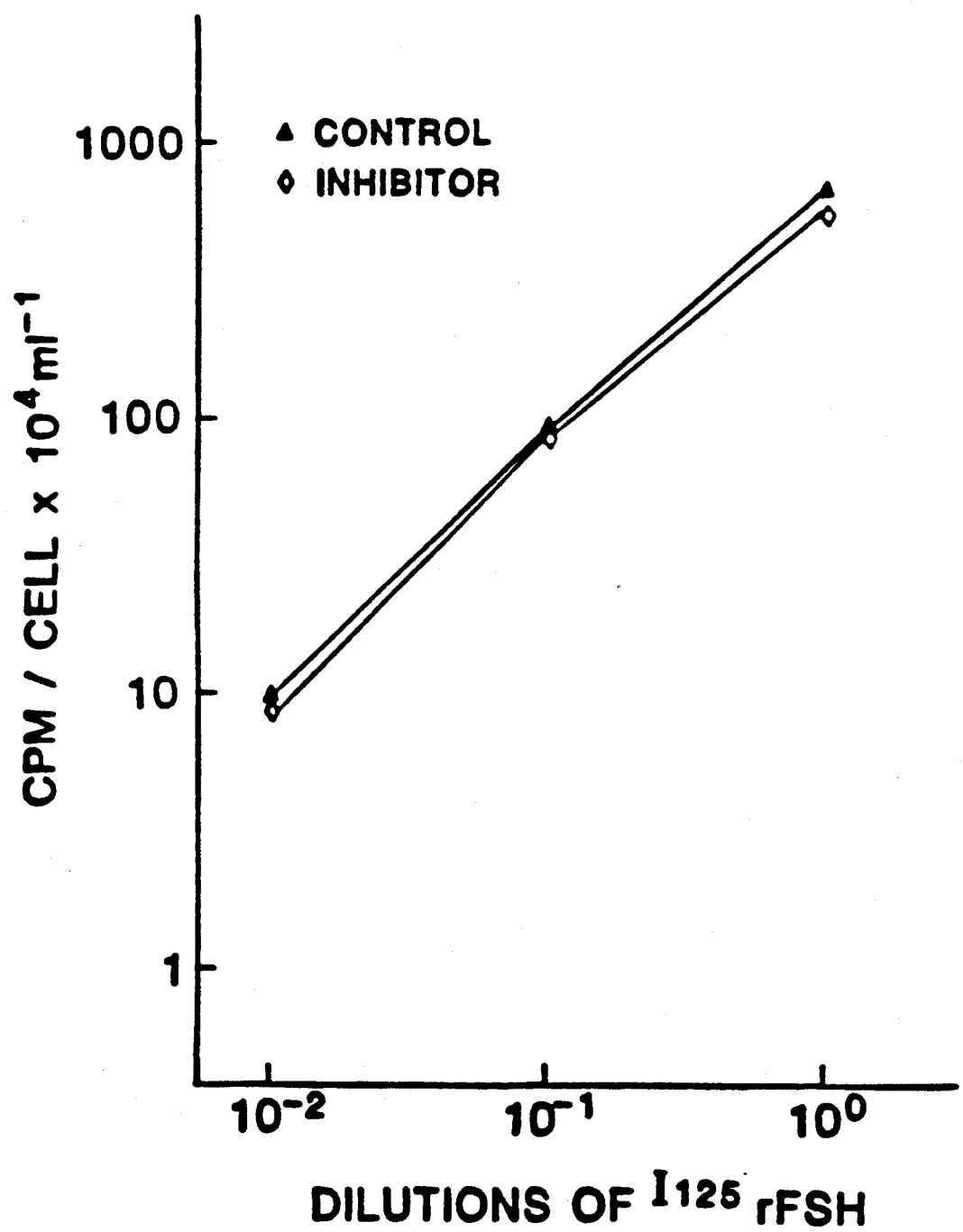
FIG. 18: Binding of FSH to granulosa cells collected from the immature, hypophysectomized, DES-treated rats (n=6) which received LH/FSH (2 Iu) and extracted porcine follicular fluid after Sephadex G-100 separation (Ve/Vo 1.3-1.7) (2 ml). Specific binding of rFSH to granulosa cells was determined by incubating three concentrations of labeled rFSH in the presence and absence of excess unlabeled rFSH.
Figure 19A:
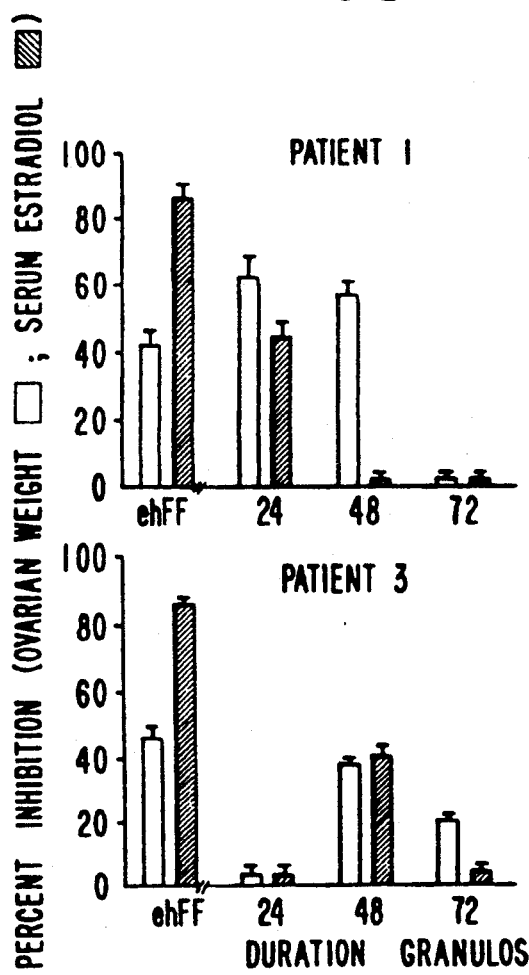
FIGS. 19a-d: Effect of extracted hFF and respective granulosa cell culture media (twenty-four, forty-eight and seventy-two hours) on the inhibition of LH/FSH (2 IU)-stimulated immature, hypophysectomized, DES-treated rat ovarian weight augmentation and serum estradiol secretion (2 ml/rat). Each value represents the mean±SE of three rats. These data indicate that GRP is secreted by the granulosa cells.
Figure 19B:
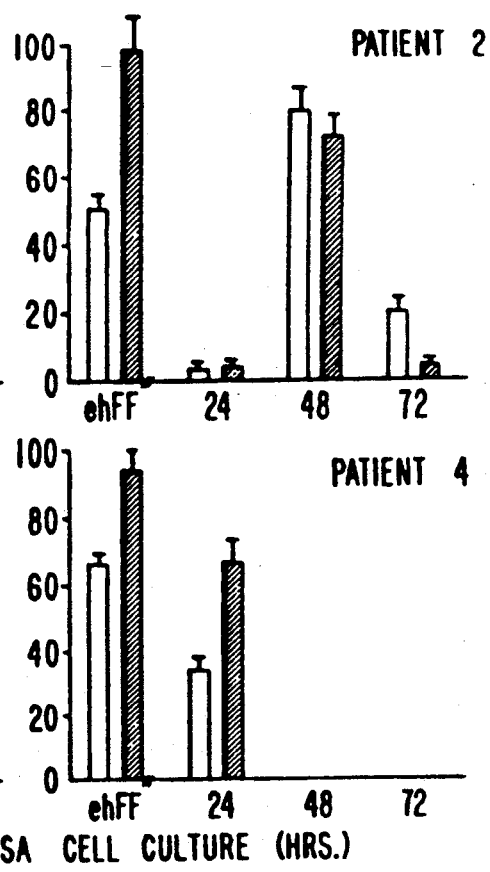
Figure 19C:
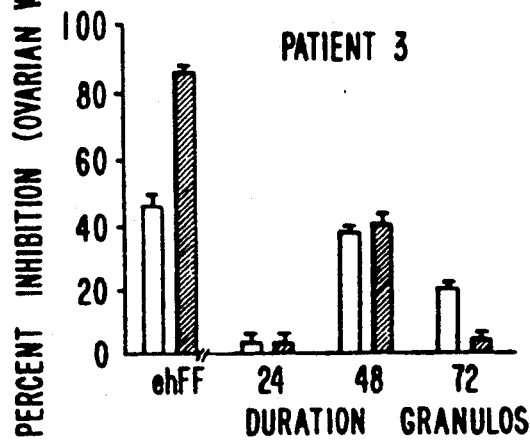
Figure 19D:
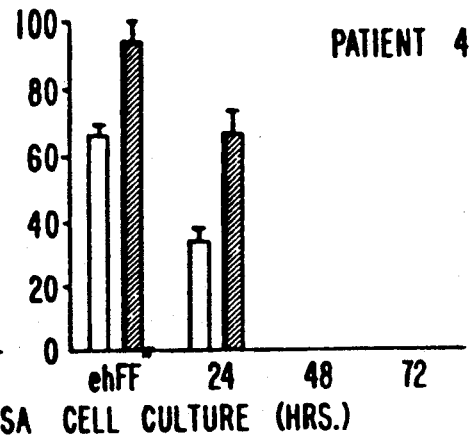

FIG. 18 shows the results of FSH binding studies performed on the granulosa cells removed from the HIFR-hMG rats used in the bioassay of the Sephadex-G100 fraction which contained inhibitory activity. No difference in FSH binding to the rat granulosa cells was evident between the control and inhibitor treated HIFR-hMG rats.

Subsequent procedures, identical to those described in this example regarding porcine follicular fluid, have isolated FRP having a molecular weight range of about 12,000 to 18,000 daltons and an isoelectric point of from pH 4.0 to 6.5, and inhibiting aromatase activity as described above, from bovine follicular fluid.

EXAMPLE FOUR

Identification of Regulatory Protein(s) in Human Granulosa Cell Secretions

Follicular fluid was aspirated from regularly menstruating women (twenty-five to thirty-five years old), undergoing clomiphene citrate (150 mg/day for five days, beginning three-eight days after the onset of spontaneously occurring menses) and hCG (4000 IU, 36 hours before aspiration) therapy during participation in an in vitro fertilization protocol. Serum was collected daily, and estrogen concentrations were determined. When serum estrogen concentrations exceeded 800–1000 pg/ml, patients underwent laparoscopy for aspiration of follicles in excess of 20 mm in diameter. Follicular aspirates were immediately centrifuged (800×g), granulosa cells were removed for culture, and the supernatant was frozen. Follicular aspirates from seven patients were evaluated.

Individual hFF samples were slowly thawed and fractionated by dropwise addition of an equal volume of saturated ammonium sulfate during persistent agitation at 4° C. After a twelve hour incubation at 4° C., the precipitate was recovered by centrifugation and resuspended (2:1, vol/vol) in 10% ammonium sulfate. An additional twelve hours of mixing was followed by centrifugation at 3,000×g for thirty minutes. The resulting supernatant was dialyzed (10,000 molecular weight exclusion membranes) against phosphate-buffered saline (PBS) (0,025M; H 6.8) for sixteen hours at 4° C. and then lyophilized. The retentate (500 mg in 0.5 ml aliquots) was passed through a column (9×32 mm; bed volume, 2 ml) containing agarose-immobilized Orange A (Dye matrix, Amicon), which had been equilibrated with 20 mM Tris-HCl, pH 7.5. Unbound material was eluted with 10 ml 20 mM Tris-HCl, pH 7.5 and bound material was eluted with 10 ml 1.5M KCl in 20 mM Tris-HCl pH 7.5. Bound eluent fractions were dialyzed overnight against PBS or distilled water. Protein concentrations were determined by the method of Lowry et al., *J. Biol. Chem.* 143:265.

Rats were prepared for bioassay as described in the previous examples.

Results of control determinations (no injected test fractions) were 34.8±3.2 mg/rat for unstimulated ovarian weight and 122.0±13.5 mg/rat for FSH-stimulated ovarian weight. Control levels of trunk serum estradiol were 12.5±0.7 pg/ml for unstimulated and 118.5±21 pg/ml for LH/FSH stimulated. Where indicated, 100% inhibition equals the ovarian weight and/or serum estradiol concentration of mean unstimulated control values. Zero percent inhibition equals the ovarian weight or serum estradiol concentration of LH/FSH-stimulated control rats. These results are similar to those obtained during the previous examples. Tests of statistical significance were performed by Student's t test and Duncan's multiple range analysis.

FIG. 19 depicts the effect of extracted human follicular fluid (ehFF) and respective granulosa cell culture media (24, 48, and 72 hours) on the inhibition of LH/FSH (2 IU)-stimulated rat ovarian weight augmentation and serum estradiol secretion (2 ml/rat). Each value represents the mean±SEM of three rats.

All four follicular fluid extracts (ehFF) contained inhibitory activity, as evidenced by inhibition of both rat ovarian weight (40–65%) and trunk serum estradiol concentrations (85–100%). Bioassay of culture media from the respective granulosa cell cultures collected twenty-four, forty-eight and seventy-two hours after plating indicated that inhibitory activity was present during the first forty-eight hours of incubation. Variability in the initial twenty-four hour determination of patients 2 and 3 may relate to initial plating efficiency. Importantly, all-bioassay determinations were made after complete medium changes each twenty-four hours. No inhibitory activity was noted after seventy-two hours of culture.

FIG. 20 depicts the compiled (mean±SE) bioassay results of culture media (containing FRP) derived from granulosa cell cultures of patients 5, 6 and 7. All media tested without gonadotropins added to the culture contained inhibitory activity of both ovarian weight and trunk serum estradiol concentrations exceeding 75% throughout the first two days of culture. Thereafter (days 3 and 4), the inhibitory activity of media from unstimulated cultures declined (43% and 37%, and 18% and 12% for ovarian weight and serum estradiol levels, respectively). After coincubation of the granulosa cells with varying doses of LH/FSH (0.3, 1.0 and 3.0 U), inhibitory activity, as determined in the HIFR-hMG bioassay, was markedly suppressed in all cultures after the first twenty-four hours (>20%).

When progesterone concentrations were determined for these culture media, an inverse correlation between inhibitory activity in the bioassay and culture medium progesterone concentrations was apparent. The unstimulated cultures (no added LH/FSH) had the least progesterone throughout the four days of culture (<10 ng/ml), but contained inhibitory activity (FIG. 20), albeit in decreasing amounts as culture duration continued. However, after LH/FSH was added to the granulosa cell cultures in increasing amounts, the progesterone concentrations rose in a dose-and time-dependent pattern, while bioassay inhibitory activity declined to essentially the limits of bioassay detectability (FIG. 20).

High performance liquid chromatography

The high performance liquid chromatographic (HPLC) separation of follicular fluid steroids was performed.

Protein separation was performed using the same Waters HPLC/GPC Model 244 liquid chromatograph equipped with two Waters I-125 gel exclusion columns connected in series. A 10-μl aliquot of the dialyzed, Orange A dye matrix-bound eluent was separated on each HPLC run. The proteins were eluted from the I-125 columns using an isocratic gradient of 0.02M PBS, pH 7.0, at a flow of 0.5 ml/minute (800 psi). The protein peaks were detected at 280 nm, and molecular weight estimates of the specific follicular fluid proteins were performed using highly purified molecular weight chromatography standards of ribonuclease-A, chymotrypsin, ovalbumin, and BSA.

Granulosa cells were cultured for up to four days in twenty-four hour intervals using 35×10-mm tissue culture dishes and 2 ml medium 199 containing 25 mM Hepes supplemented with 100 U/ml penicillin, 100 μg streptomycin sulfate, and 15% fetal calf serum (medium A). Cultures were maintained in a humidified, 95% air-5% $CO_2$ incubator at 37° C. After each twenty-four hour incubation period, spent medium was collected and stored frozen at −20° C. until bioassay was performed. Where indicated, human menopausal gonadotropin (FSH-LH, 1:1) was added to specific cultures at the time of complete medium change. At the end of each twenty-four hour incubation period, spent medium was collected for bioassay, and 2 ml fresh medium were added. The final cell pellets were dispersed in medium A, and aliquots (0.5 ml) of the cell suspension were diluted with 0.05 ml trypan blue for quantitation of viable cells in a hemocytometer. Initial plating density was $0.5 \times 10^5$ granulosa cells/plate.

Granulosa cells were isolated from rat ovaries and were collected by centrifugation at 800×g at 4° C. for ten minutes. FSH binding was determined using a modification of known techniques. Rat FSH, provided by the National Pituitary Agency, was labeled by the chloramine-T procedure. Cells were resuspended in appropriate volumes of PBS-01% gelatin (PBS-gel), pH 7.0. All assays were run with three concentration of labeled hormone (100 μl), buffer (PBS-0.1% gel; 100 μl) and 100 μl cells. Reactions were initiated by the addition of granulosa cells and were carried out for four hours at 25° C. Reactions were terminated by adding 1 ml cold PBS, followed by centrifugation at 30,000×g for ten minutes. The supernatant was carefully aspirated, and the pellet was rewashed with 1 ml PBS. The final pellet was counted in a γ-counter. Specific binding was calculated as the difference between binding in the presence (nonspecific) and absence (total) of an excess of unlabeled hormone.

FIG. 21 depicts the FSH binding studies performed on the granulosa cells removed from the HIFR-hMG-treated rat ovaries used in the bioassay experiments shown in FIG. 19. Specific binding of rat FSH (rFSH) to granulosa cells was determined by incubating three concentrations of labeled rFSH in the presence and absence of excess unlabeled rFSH. Rat granulosa cell specific FSH binding was similar whether the rat received injections of spent medium from human granulosa cell cultures or saline. However, a marked difference in the ovarian weight and trunk serum estradiol concentrations of these rats was present.

Replicate 0.1-ml portions of each rat granulosa cell suspension were pipetted into 12×75-mm polystyrene tubes. Androstenedione, the referent aromatase substrate, was added in 0.1 ml medium A (final concentration, $1.0 \times 10^{-7}$M). All incubations were performed in triplicate for three hours at 37° C. in a shaking water bath (120 cycles/minute). The reaction was stopped by transferring the tubes to an iced water bath before centrifugation for five minutes at 1000×g. The supernatants were decanted and stored at −20° C. until measurements of estradiol and estrone were performed. Control incubations (no androstenedione added) were processed in the same way. Blank estrogen values obtained for the controls were subtracted from the corresponding values for incubations in the presence of androstenedione. Aromatase activity was expressed as estrogen production (nanograms per viable granulosa cell).

Rat granulosa cell aromatase activity is 30 shown in FIG. 22 and was markedly inhibited ($P<0.01$) by treatment with spent media from all four days of culture ($2.4\pm0.4$, $2.9\pm0.7$, $2.4\pm0.4$, and $2.1\pm0.2$ pg estrogen/10,000 viable cells/ml, respectively, compared to saline control $4.6\pm0.2$ pg estrogen/10,000 viable cells/ml. Control determinations were performed on rat granulosa cells collected from HIFR-hMG-treated rats which did not receive culture medium injections. Inhibition of relative estrogen production by rat granulosa cells in the presence of $10^{-7}$M androstenedione was seen throughout all four days of human granulosa cell culture medium treatment. Taken together, these data indicate that although no marked inhibition of rat granulosa cell FSH binding was induced by the human granulosa cell culture medium, a clear disruption of aromatase activity occurred, which may account for the decreased rat ovarian weight and serum estradiol concentrations.

Using the same purification techniques and bioassays described above, a similar protein or proteins have been identified in the culture media derived from the granulosa cells of human follicles. This data indicates that human granulosa cells secrete a protein that inhibits follicular response to gonadotropins.

All of the antral fluid's steroid concentrations suggested premature luteinization. After extraction, all seven follicular fluids contained inhibitory activity, as evidenced by reduction of both rat ovarian weight (45-85%) and trunk serum estradiol concentrations (85-100%) in the HIFR-hMG bioassay. Bioassay of these follicles' granulosa cell culture media indicated inhibitory activity present during the first forty-eight hours, while no inhibitory activity was noted after seventy-two hours of culture. Spent culture media derived from granulosa cells cultured without additional gonadotropins contained inhibitory activity in the HIFR-hMG bioassay throughout the first two days in vitro. Thereafter (days 3 and 4), inhibitory activity of media from unstimulated cultures declined. After coincubation of the granulosa cells with varying doses of LH/FSH, inhibitory activity was markedly suppressed even after the first twenty-four hours. An inverse correlation was apparent between inhibitory activity in the bioassay and the culture medium progesterone level. Although FSH binding of granulosa cells derived from rats used in the HIFR-hMG bioassay was similar with or without injection of test fractions, their aromatase activity was markedly inhibited by treatment with human granulosa cell culture medium. These data indicate that although no marked inhibition in rat granulosa cell FSH binding was induced by the human granulosa cell culture medium, a clear disruption of aromatase activity occurred, which accounts for the decreased rat ovarian weight and serum estradiol concentrations found in the bioassay. Disruption of gonadotropin-mediated aromatase induction by an intrafollicular protein may, in part, modulate the local balance between C-19 steroid aromatase and 5-α-reductase enzymic activities in individual follicles.

A variety of nonsteroidal regulators of ovarian function have been identified in a variety of species, including oocyte maturation inhibitor, luteinizing inhibitor, folliculostatin or inhibin, and FSH binding inhibitor. The biophysical characteristics of the intragonadal protein of this invention are different from such substances.

This material elutes through gel exclusion chromatography with a molecular weight of 12,000–18,000, binds to Orange A dye matrix, and has an apparent isoelectric point of from pH 4.0–4.5 to 6.0–6.5. These observations indicate that in addition to the intrafollicular steroidal mileau a variety of nonsteroidal compounds, secretory products of the granulose cells or other ovarian compartments, contribute to the regulation of folliculogenesis.

EXAMPLE FIVE

The presence of the gonadal regulating protein in Testis

Figure 24:
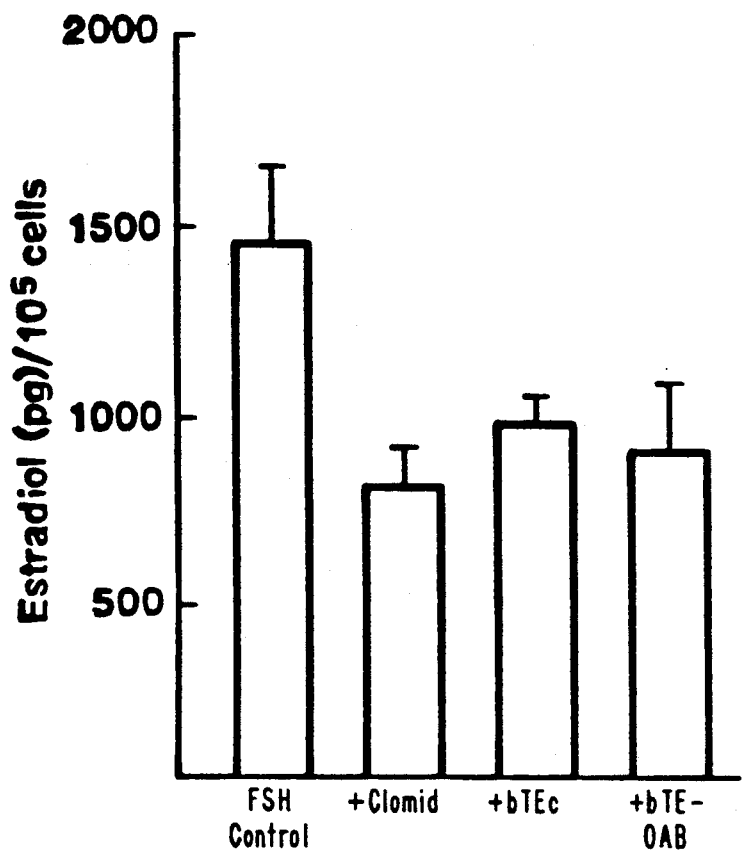
FIG. 24: Inhibition of FSH stimulated (FSH control) porcine granulosa cell aromatase activity measured by determination of estradiol concentrations in spent culture media after incubating the cells with the following reagents for 24 hours followed by androstenedione ($10^{-6}$M) for three hours: ovarian vein serum from clomiphene citrate treated baboons (+clomid); bovine testis extract (+bTEC); bovine testis extract which binds to dyematrix Orange A and elutes with 0.5M KCl+TRIS (+bTE-OAB).
Figure 25:
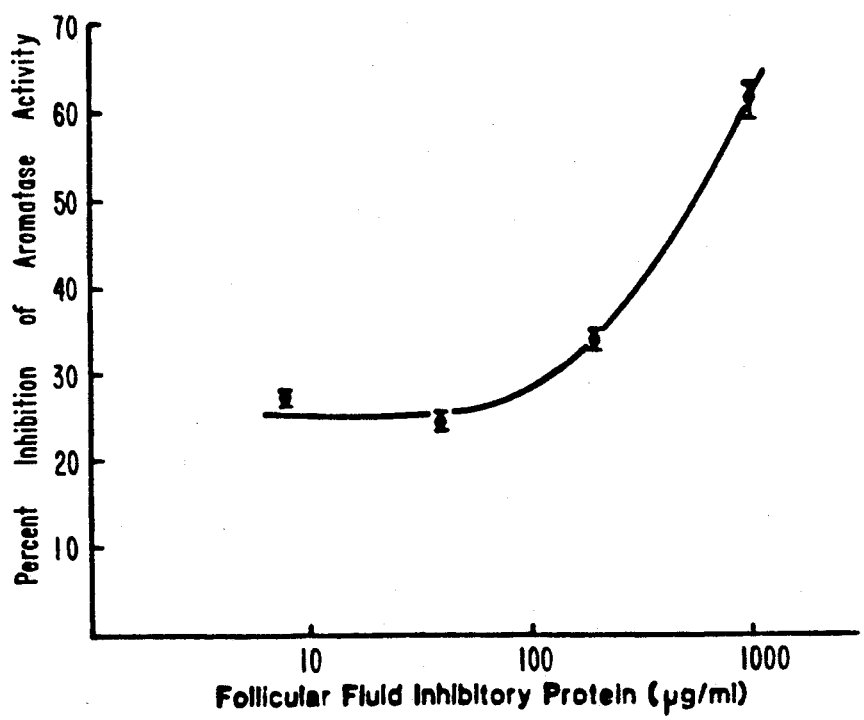
FIG. 25: Dose-response inhibition of porcine granulosa cell aromatase activity by FRP isolated from human follicular fluid. Aromatase activity was determined in triplicate determinations with granulosa cells ($10^6$/culture), androstenedione ($10^{-6}$M) and pFSH (2ng) co-cultured for three hours.

Bovine testis were homogenized and the homogenate precipitated with 55% saturated ammonium sulfate. The precipitate was resuspended and dialyzed against distilled water. The retentate was eluted though Sephadex G-100 with TRIS buffer (20 mM, pH 7.5). The eluant corresponding to a molecular weight range of 12,000–18,000 was collected and charged into an Orange A dye matrix column. The column was eluted with TRIS buffer containing 0.5M KCl (20 mM, pH 7.5). This eluant contained FRP as evidenced by the inhibition of porcine granulosa cell aromatase activity (FIG. 23; bTEc and bTE-OAB columns) and rat serum estradiol levels (FIG. 24; BTE+FSH and BTE-OAB+FSH columns). Further, this activity was contained in testicular extract fractions with isoelectric points of from pH 4.1–4.5 and 6.0–6.5. This demonstrates that the testis and its secretory product, rete testis fluid, also contains FRP.

EXAMPLE SIX

Extraction of FRP from Sertoli Cell Cultures

Granulosa cells secrete FRP, and Sertoli cells are the embryonic homologue in testis of the granulosa cells in the ovary. Further, the biological activities of granulosa cells are present in the Sertoli cells insofar as they have been identified and are relevant to gonadal function. Thus, the Sertoli cell provides an additional, readily available source of FRP. Accordingly, Sertoli cells may be grown in cell culture and the recovered culture media is extracted by the procedures described in the foregoing examples, principally salt participation, chromatographic procedures and electrophoresis.

II. BIOLOGICAL ACTIVITY

EXAMPLE SEVEN

The Effect of the Gonadal Regulatory Protein as an Aromatase Inhibitor

In Examples One through Six, protein(s) in human ovarian venous effluent, human and porcine follicular fluid, bovine testis fluid and spent media from human granulosa and rat Sertoli cell cultures inhibited rat ovarian weight gain in response to gonadotropin stimulation. Gonadal fluid extracts containing this protein were found to have a molecular weight of 12,000–18,000 and an isoelectric point of from about pH 4.0–4.5 to pH 6.0–6.5. As inhibin, another protein secreted by human granulosa cells, increases with follicular maturation and decreases with luteinization, individual human follicles from untreated as well as hMG and clomiphene treated women were assessed for FRP activity, and that activity was correlated with the follicles' follicular fluid steroid and inhibin concentrations.

Follicular aspirates were obtained from women (aged twenty-four-thirty-two years) who were participating in an in vitro fertilization protocol. All patients had regular ovulatory menstrual cycles based on monthly vaginal bleeding and at least a single luteal phase serum progesterone in excess of 3 ng/ml. When serial ultrasonographic examinations (ADR Model 2140 real-time sector scanner with a 3.5 mHz rotating head transducer) demonstrated a follicular diameter in excess of 18 mm laparoscopy was performed for aspiration of all follicles greater than 16 mm in diameter. Follicular aspirates were immediately transferred to an adjacent laboratory for removal of granulosa cells by centrifugation (600×G, 15 minutes) and storage of follicular fluid ($-37°$ C.) until assay. Follicular fluid concentrations of estradiol, progesterone, 17-hydroxy progesterone, androstenedione and testosterone were determined by established radioimmunoassay techniques.

FRP was isolated from individual follicular fluid samples substantially as described in Example Two.

Aromatase Activity

Porcine granulosa cells were collected from fresh ovaries obtained at the local slaughterhouse. After washing in serum free HAMS-HEPES tissue culture media, $5 \times 10^5$ cells in 0.2 ml of medium were pipetted into $12 \times 75$ mm polystyrene tubes. Triplicate 200 $\mu$l portions of each follicular fluid preparation at three different protein concentrations (700–10 ug/ml) were tested. Each tube then received 100 $\mu$l of FSH(10 ng) in culture medium and was incubated at 37° C. in a shaking water bath for three hours. An atmosphere of 90% $N_2$, 5% $O_2$ and 5% $CO_2$ was maintained throughout the incubation. The incubation was stopped by the addition of 0.5 ml Hams-Hepes media and centrifugation at $1000 \times g$ for five minutes. The granulosa cells were then resuspended in 0.5 ml Hams-Hepes media, whereupon 100 $\mu$l of cells were assayed for armoatase activity. Androstenedione, the referent aromatase substrate, was added in 0.1 ml medium (final concentration, $1.0 \times 10^{-7}$M). All incubations were performed in duplicate for three hours at 37° C. in a shaking water bath (120 cycles/minute). The reaction was stopped by transferring the tubes to an iced water bath before centrifugation (five minutes at $1000 \times g$). The supernatants were decanted and stored at $-20°$ C. until measurements of estrogen were performed. Control incubations (no androstenedione added) were processed in the same way. Blank estrogen values obtained for the controls were subtracted from the corresponding values for incubations in the presence of androstenedione. Aromatase activity was expressed as estrogen production (nanograms per viable granulosa cell).

Inhibin Activity

Ten percent (weight/volume) activated charcoal (Norite A) was added to the individual follicular fluids, and stirred continuously overnight at 4° C., followed by centrifugation (1000×G, twenty minutes) and sterile filtered to remove the charcoal. The charcoal-stripped follicular fluid contained 10 pg/ml of androstenedione, progesterone, and estradiol as determined by radioimmunoassay. Inhibin activity was determined using the degree of inhibition of basal (i.e. non-LHRH stimulated) twenty-four hour FSH secretion by dispersed rat anterior pituitary cells in primary monolayer. For each cell culture, anterior pituitary glands were obtained from 20 cycling female Sprague-Dawly rats (250–300 gm body weight). During the thirty minute interval required for removal of all the pituitary glands, each gland was placed in medium (pH 7.4, 20° C.). Pituitary glands were finely minced with scissors and incubated in a mixture containing 1% viokase, 3.5% collagenase, and 3% bovine serum albumin in medium buffer at 37° C. for thirty to forty-five minutes. The dispersed cells were counted using a hemocytometer and pituicyte viability was determined by 1% trypan blue exclusion. Typically, more than 90% of the dispersed cells were viable. The cells were diluted to a concentration of $2.5 \times 10^5$ viable cells per ml growth medium. Growth medium consisted of HAMS F10 containing 10% fetal calf serum with penicillin, fungiezone and streptomycin (50 u/ml and 50 mg/ml and 50 mg/ml respectively). Cells were added to tissue culture dishes in a volume of 2.0 ml growth media, and attachment of the cells to the well surface was completed by two days. After cell attachment, the original growth media was discarded and the cells were washed twice with additional HAMS balanced salt solution. Thereafter, three concentrations of charcoal-treated follicular fluid (0.02%, 0.2%, 2%) were added to the plate. A lyophilized porcine follicular fluid standard (PFF1 KT-1, provided by CP Channing) was resuspended in water and tested in each assay at 0.003%, 0.016%, 0.08%, 0.04%, and 2% concentrations. Twenty-four hours later, the spent culture media was assayed in duplicate using the NIH-RIA kit for rFSH.

Data Analysis

The mean estrogen concentration in the serum control tube for each FRPassay was set at 100%, and the response in each test was expressed as a percentage of the control estrogen concentration. The coefficient of variation for each group of three replicate tubes was calculated. If the coefficient was 15%, the estrogen assay was repeated and/or one value of the three was discarded. A curve was constructed in which the percent inhibition of estrogen in each well was plotted vs the protein concentration of follicular fluid added. Unknown values were determined by plotting the experimentally determined values at three different protein concentrations (700–10 ug/ml) on a log-linear graph and extrapolating the value at 50 ug/ml. The percent inhibition of estradiol at 50 ug of unknown follicular fluid was read off the standard curve and expressed as percent aromatase inhibition for that follicle.

For the inhibin assay, the response in each test plate was expressed as a percentage of the control FSH concentration, which was set at 100%. The coefficient of variation of each group of three replicate plates was calculated. If the coefficient was 15% the assay was repeated. A standard curve was constructed in which the percent inhibition of FSH in standard wells was plotted vs the log of the standard added. Least squares linear regression was used to construct a standard curve in the linear portion of the dose response curve. Unknown follicular fluid inhibin values were determined by plotting the experimentally determined values (0.02%, 0.2%, 2%) on a log-linear graph and extrapolating the value at 1%. The percent inhibition of rFSH at 1% of unknown follicular fluid was read off the standard curve and expressed as Channing units (1 CU=1 unit of inhibin standard=the inhibition of rFSH in rat pituicyte culture by 1 nl of charcoal treated, ethanol extracted porcine follicular fluid).

Tests for statistical significance were performed by one-way analysis of variance and Duncan's new multiple range test. Correlation between follicular fluid steroid concentration and FRP activity was performed using regression analysis with tests of statistical significance performed by t test corrected for N.

Patient Outcome

Seven patients underwent follicular aspiration during an untreated spontaneously occurring ovarian cycle. At the time of laparoscopy, only one antral follicle was seen in each patient which was aspirated. Nine patients received clomiphene citrate therapy (150 mg/day, cycle days 5–9), providing a total of twenty-four follicles with diameters >16 mm. All except one patient had multiple follicles aspirated. Six patients who underwent hMG therapy (150 IU LH/150 IU FSH administered daily beginning on cycle day 3 until follicle aspiration), provided twenty-three follicles. Care was taken to aspirate all follicles with diameters in excess of 16 mm. There was no difference between treatment groups in follicle size which averaged $18.7 \pm .9$ mm (x±SEM, range 16–24 mm). At the time of aspiration, serum estradiol levels averaged 1456 pg/ml±285 pg/ml for all patients studied (range of 310–3200 pg/ml) with no significant difference between treatment groups.

Validation

To establish the number of porcine granulosa cells for the FRP assay, the following porcine granulosa cell concentrations were used: $0.5 \times 10^6$, $1 \times 10^6$, $2 \times 10^6$ cells/ml. The total amount of estrogen produced following a three-hour incubation was $55 \pm 9$, $140 \pm 27$, $375 \pm 48$ pg/culture dish, respectively. Consequently, $2 \times 10^6$ porcine granulosa cells were used in each subsequent assay. To evaluate the effects of porcine FSH (NIH P-2 reagent) and follicular protein (100 ug), porcine granulosa cell cultures were prepared with or without porcine FSH added to the media (0.5 ml final volume), incubated at 37° C. for three hours in a shaker bath with 95% $O_2$ and 5% $CO_2$, after which androstenedione ($10^{-6}$M) was added in 0.5 ml of growth media. Cultures were incubated for three hours at 37° C. in a shaker bath then centrifuged ($1000 \times G$ for fifteen minutes) and media collected for estrogen determination. Without FSH, the estrogen production was $439 \pm 41$ pg/ml; with FRP added, the estrogen production was $22.4 \pm 41.7$ pg/ml. When 2 units/ml of porcine FSH were added without FRP 728 pg/ml estrogen were produced. Addition of FRP produced a dose-response relationship 1000 ug FRP: 200.26 pg/ml; 200 ug FRP: 306.37 pg/ml; 50 ng FRP: 345.41 pg/ml; 10 ug FRP: $334 \pm 18$ pg/ml of estrogen. Accordingly, individual patient values were extrapolated to 50 ng/ml of FRP for comparisons of activity.

The FRP in elution profiles from Orange A were analyzed using three different concentrations of KCl: 0.17M KCl yielded 3.1 mg protein/ml which had a 37% inhibition of aromatase, 0.5M KCl eluted 6 mg protein-ml which had an 84% inhibition of aromatase and 1.5M KCl eluted 0.05 mg protein/ml which had a 6.7% inhibition of aromatase. Accordingly, the 0.5M KCl fraction was used to elute the active material from the Orange A bound column. KCl (0.5M) was found to have no effect in the granulosa cell aromatase assay: control (without KCl, 3 determinations, $710 \pm 41$ ng/ml. with KCl, $712 \pm 38$ ng/ml). Duration of incubation time was assessed with and without FSH. Two hour assay incubations yielded 2 ng estrogen/ml; twenty-four hours: 5.3 ng estrogen/ml. With 2 ng FSH added, 39 ng estrogen/ml at two hours and 6 ng FSH/ml produced 8 ng estrogen/ml at twenty-four hours. With 1 ng FSH/ml, 35±1.8 ng estrogen/ml were produced at two hours and 4.7±0.9 ng estrogen/ml at twenty-four hours. Accordingly, a three-hour incubation was used to determine specific FRP activity.

When FRP preparation was heated to 56° C.×1 hours, the inhibition of granulosa cell aromatase was lost. The FRP activity levels (% inhibition of porcine granulosa cell aromatase by 50 ug of follicular fluid) for untreated patients was 14.16±5.32% (X±SEM). For patients receiving hMG, FRP levels were 18.09±3.46%, and for patients receiving clomiphene, 13.7±5.36%. There was no statistically significant difference in the values between the three treatment groups. The amount of estradiol in the follicular fluid of untreated patients was 2.59±1.2 ug/ml, for patients receiving hMG therapy, 0.34±0.5 ug/ml, for patients receiving clomiphene, 1.31±0.34 ug/ml. These values were all significantly different ($p<0.05$, untreated vs clomiphene, clomiphene vs hMG; $p<0.01$ untreated vs hMG). Progesterone values for untreated patients were 9.84±3.35 ug/ml, for hMG-treated patients, 5.18±1.1 ug/ml, and for clomiphene-treated patients, 11.3±2.3 ug/ml These differences were significant for the unstimulated and hMG-treated patients ($p<0.05$) and hMG vs clomiphene treated patients ($p<0.01$). The 17-hydroxyprogesterone concentrations for patients receiving no additional therapy were 1.66±0.25 ug/ml, for those receiving clomiphene therapy 2.6±0.3 ug/ml, and for those receiving hMG therapy: 0.76±0.11 ug/ml. All these values were significantly different (hMG vs clomiphene $p<0.01$; hMG vs unstimulated $p<0.01$; unstimulated vs clomiphene $p<0.025$). Follicular fluid androstenedione concentrations in untreated patients were 61.9±43 ng/ml. For hMG and clomiphene treated patients they were 85.5±37, and 84.8±43 ng/ml, respectively. Follicular fluid testosterone levels from untreated patients were 7.34 ng/ml±3.7. For the treated patients, there was no difference in the follicular fluid testosterone concentrations in patients receiving either hMG (7.09±2.14 ng/ml) or clomiphene (6.14±1.8 ng/ml).

Correlation of FRP vs Follicular Fluid Steroids

Figures 26A, 26B, 26C:
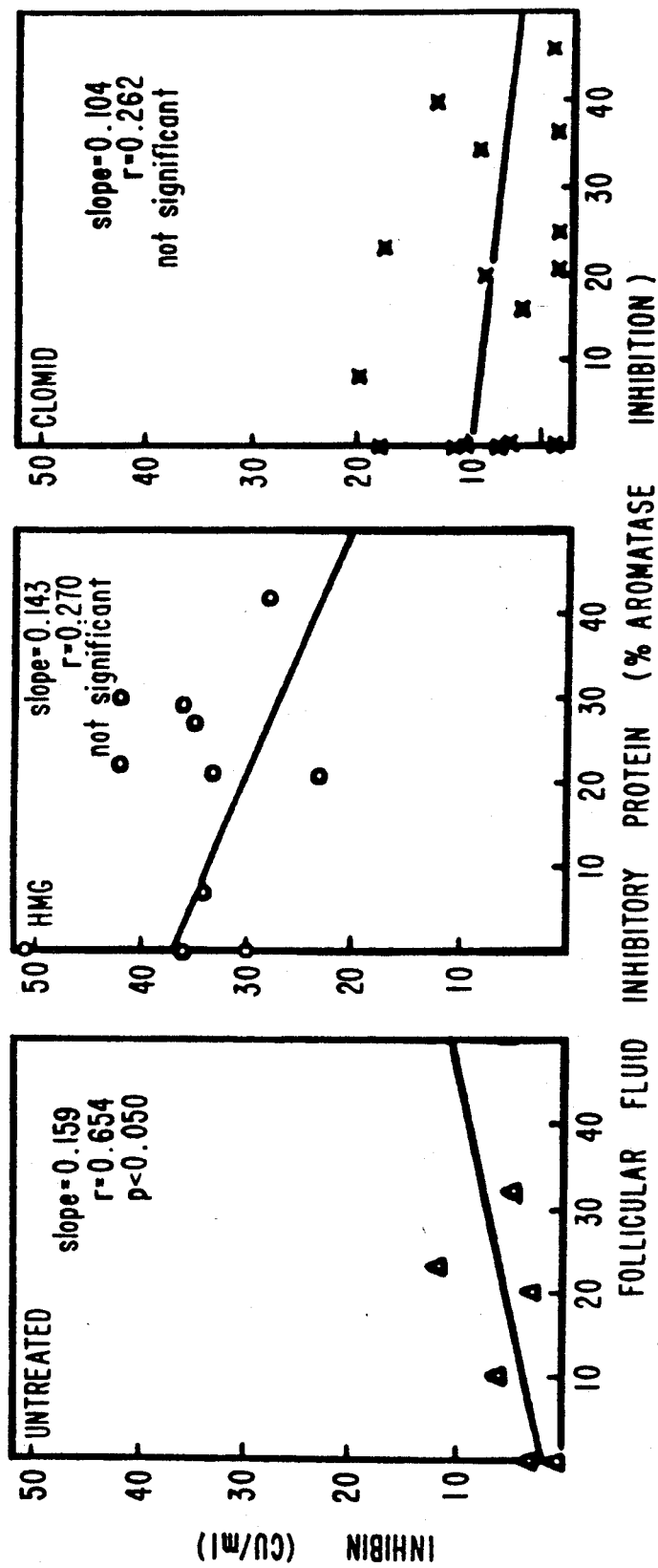
FIGS. 26a-c: Correlation of follicular fluid inhibin activity (inhibition of spontaneous rFSH release by pituicytes) and gonadal regulatory protein activity (% aromatase inhibition) in regularly menstruating women either untreated or after receiving HMG or clomiphene therapy. A statistically significant correlation (r=0.650, p<0.05) was apparent between inhibin and follicular protein activities in follicular fluid from untreated patients only, indicating that inhibin and FRP are not the same protein.

There was a positive correlation between follicular fluid estradiol concentrations and FRP protein activity in untreated patients ($r=0.689$, $p.<0.01$). For patients receiving hMG therapy, there was no significant correlation between FRP activity and follicular level estradiol concentrations ($r=0.490$, $p<0.1$). For patients receiving clomiphene therapy, the correlation between FRP activity and follicular fluid estradiol was described by two populations using a second degree regression analysis ($r_2=0.853$, $p.<0.01$). Correlation between follicular fluid progesterone concentrations and FRP activity for untreated patients ($r=0.622$, $p<0.05$) and hMG treated patients ($r=0.756$, $p<0.005$) was significant. For clomiphene treated patients, correlation between follicular fluid progesterone and FRP activity were not significant. The correlation between follicular fluid 17-hydroxyprogesterone values and FRP activity for the untreated ($r=0.833$, $P<0.001$), as well as hMG ($r_2=0.853$, $p<0.0025$) and clomiphene ($r_2=0.637$, $p<0.025$) treated patients was significant by second order regression analysis. The correlation between FRP and androstenedione concentration from untreated ($r=0.241$), hMG ($r=0.357$), and clomiphene ($r=0.219$) treated patients was not significant, nor was the correlation between testosterone and FRP activity significant ($r=0.477$, 0.409, 0.480, respectively). The average inhibin activity for untreated patients was 50±1.9 CU. In patients receiving treatment, inhibin activity was 8.2±2.3 and 35.4±3.7 CU for clomiphene and hMG treatment, respectively. Differences between hMG and either clomiphene or untreated patients were highly significant ($p<0.001$). Correlation between inhibin and FRP activities for untreated patients was significant ($r=0.654$; $p<0.05$; FIG. 26). However, there was no statistically significant correlation between inhibin and FRP activities in patients receiving either hMG ($r=0.270$) or clomiphene ($r=0.262$).

These observations report the presence of an aromatase inhibitor (FRP) in a purified fraction of human follicular fluid. This follicular fluid protein fraction (FRP) has previously been shown to inhibit hMG-mediated increases in rat ovarian weight and serum estradiol concentrations. As is shown hereinafter in Example Thirteen, when this protein fraction is injected into regularly menstruating monkeys, it disrupts folliculogenesis resulting in either anovulatory cycles or luteal phase insufficiencies accompanied by low serum estradiol and progesterone concentrations without markedly altered peripheral serum gonadotropin levels. This data, taken together with those presented previously, suggest that the developing granulosa cell, through production of an aromatase inhibitor, is capable of autoregulating the estrogen production of its own and other follicles.

Example Eight

Gonadal Regulatory Protein Inhibition of Microsomal Aromatase Activity

In this example, the effect of the gonadal-regulating protein on aromatase activity was studied in cell-free placental microsome preparations which were prepared in accordance with the techniques described in *Mol. Cell. Endocrinol.*, 6 (1976) pp. 10 5-115 and *J. Clin. Endocrinol. Metab.*, 39 (1974) 754-760.

Aromatase incubations were carried out in a total volume of 0.6 ml in 12×75 ml glass tubes as described in the above-identified references. Incubations contained 0.3 ml of placental cell-free preparation in buffer A, 0.10 ml of $^{14}$C-androstenedione (A,$10^{-6}$ molar), NADPH ($10^{-6}$ molar) and nicotinamide (0.4 molar) in buffer A. Gonadal regulatory protein test fractions (0.2 ml, 12 to 18 kd, pI 4.0–6.5), were preincubated with placental extracts (20 minutes) and then the $^{14}$C-androstenedione-NADPH mixture was added. Reaction at termination/quenching was performed by addition of 100-fold excess unlabeled A. Estrogen concentrations were determined by radioimmunoassay as described in *J. Clin. Endocrinol. Metab.*, 39, 754–760.

Figure 27:
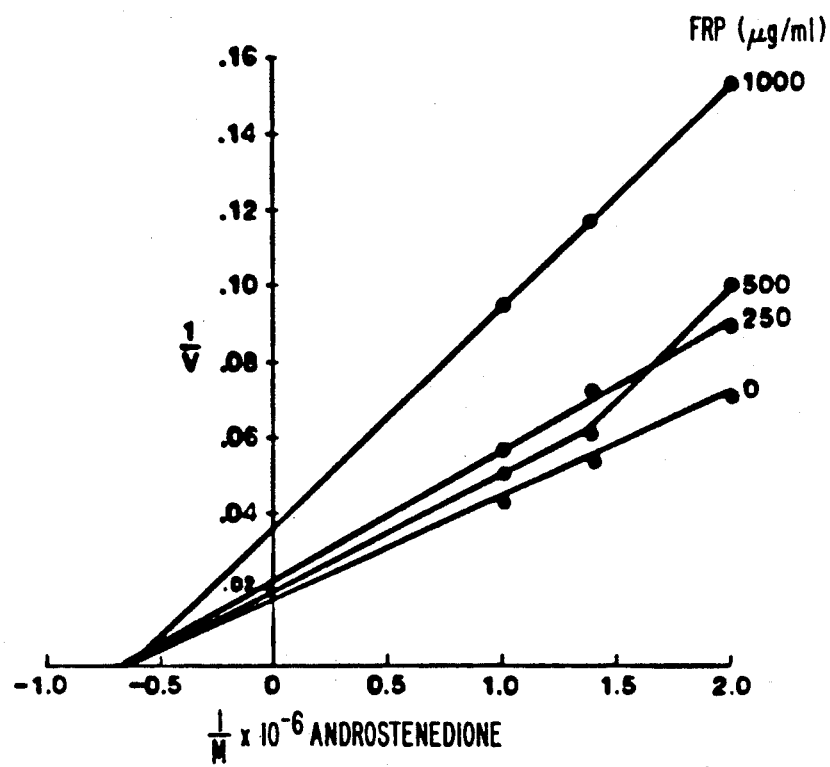
FIG. 27: Lineweaver-Burke plot of FRP (250,500,1000 ug/ml) inhibition of human placental microsomal aromatase activity in vitro.
Figure 28:
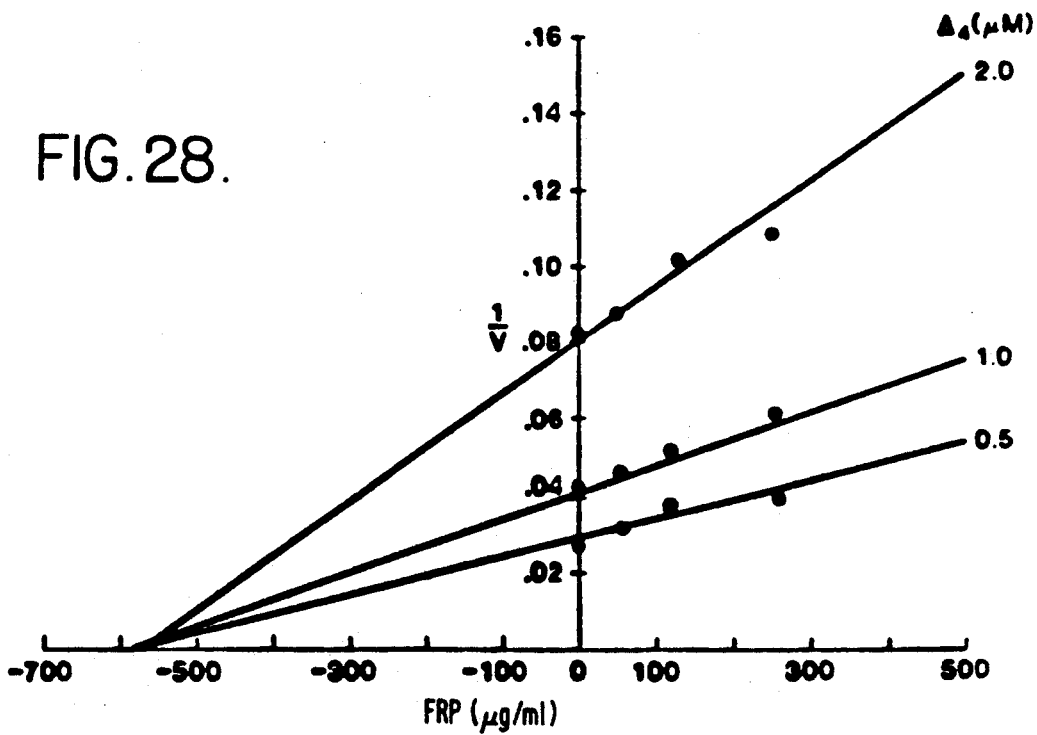
FIG. 28: Dixon plot of FRP inhibition of placental microsomal aromatase activity in vitro.

FRP-dose response determinations were performed using a three-minute reaction time. The velocities determined over a range of substrate concentrations (0.5–2 mM) demonstrated Michaelis-Menton type kinetics with a Km of 0.8 mM as shown in FIG. 27. The aromatase velocities were determined over a range of FRP concentrations (0, 62.5, 125, 250, 500 and 1,000 µg/ml). The use of Dixon kinetic plotting techniques demonstrated that FRP inhibited microsomal aromatase with an App $Ki=3\times 10^{-5}M$ (FIG. 28).

These data demonstrate the non-competitive inhibition of FRP on aromatase activity. Enzyme inhibition may be of three types. First, competitive inhibition describes the competition of the inhibitor for the substrate-specific site on the enzyme. Second, non-competitive inhibition describes a direct inhibition of the enzyme without competition for the substratespecific sites. Third, uncompetitive inhibition describes an indirect inhibition of the enzyme by additional mechanisms. In FIG. 28, the intersection of the lines at the abscissa, as opposed to ordinal intersection (competitive) or non-intersection (uncompetitive) show that FRP is a non-competitive inhibitor of aromatase activity. FRP directly interacts with the aromatase molecule to inhibit its activity.

Example Nine

Figure 29:
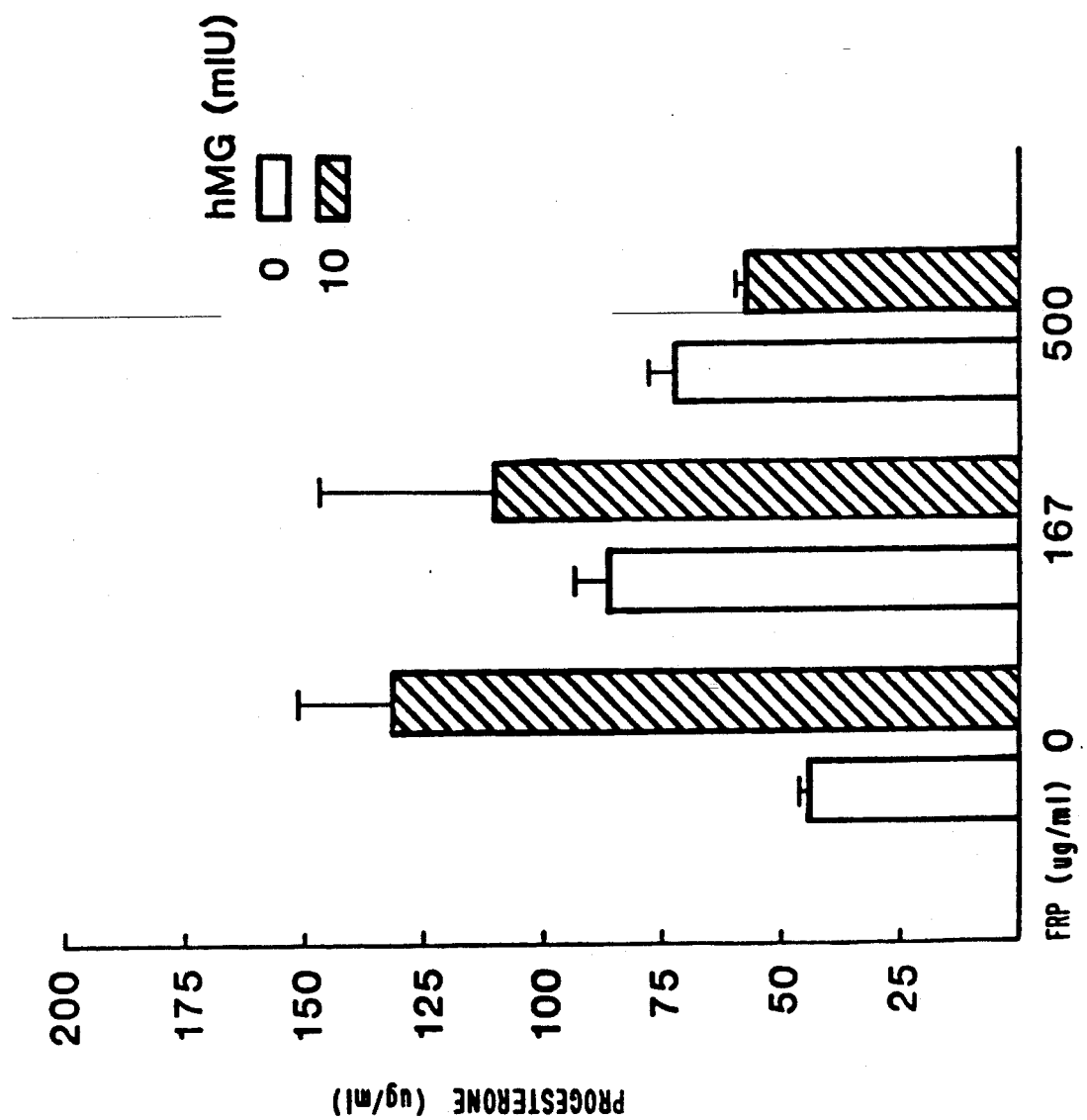
FIG. 29: Levels of progesterone (X⁻±SEM) produced by cell-free microsome enriched preparations from human granulosa cells obtained during in vivo hyperstimulation (clomiphene citrate+hMG+hCG) from women participating in an in vitro fertilization protocol. Cells were treated in vitro with or without hMG and a preparation of FRP termed follicle regulatory protein (N=5 cycles, 3-7 follicles per cycle).
Figure 30:
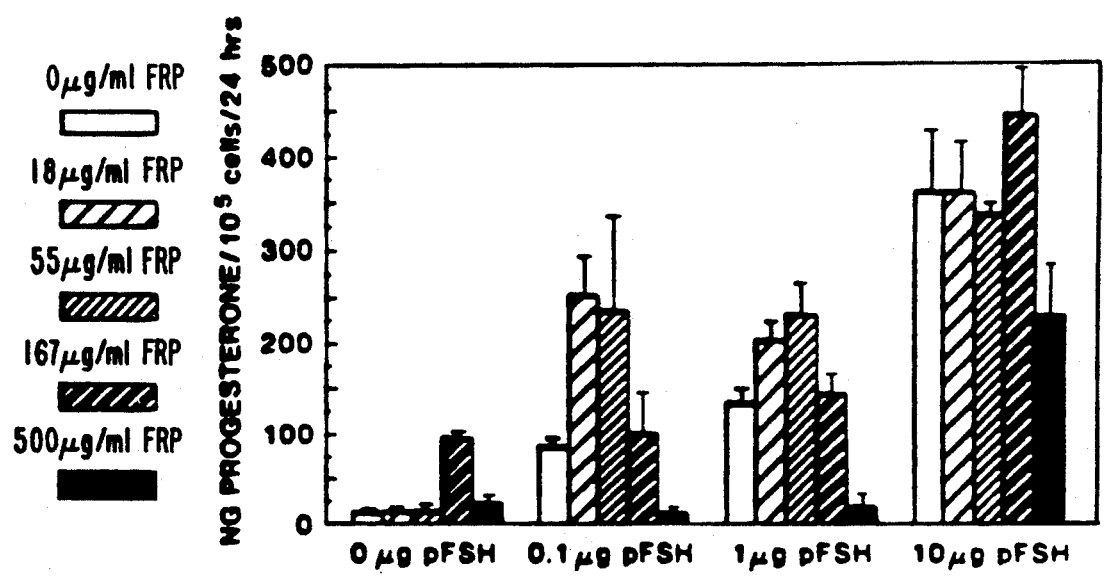
FIG. 30: The effects of FRP and pFSH on 3-beta-ol dehydrogenase activity, after 48 hours of pre-incubation, expressed as ng of progesterone (±SEM) produced per 100,000 cells per 24 hours. Total cell culture time equals 72 hours.

Modulation of Beta-ol-Dehydrogenase (3$\beta$-ol) Activity By Follicular Protein Porcine and human granulosa cells from medium sized follicles (2-5 mm in diameter) were cultured (100,000 cells per culture) with various concentrations of FRP (12-18 kd. pI 4.0-6.5) isolated from follicular fluid. To these cultures pregnenolone ($10^{-5}$M) and either hCG or pFSH were added. The conversion of pregnenolone to progesterone was used to determine 3-beta-ol-dehydrogenase activity in the granulosa cells. FRP caused a biphasic response in progesterone production. Gonadal regulatory protein in the concentration of 167 ug/ml caused a 10 fold increase in progesterone production, while the 500 ug/ml concentration caused a return to baseline levels. These results are shown in FIGS. 29 and 30. Although pFSH induced a dose response increase in progesterone production, hCG produced no change in progesterone levels. Low doses of the gonadal regulatory protein acted synergistically with low doses of pFSH to increase 3-beta-ol-dehydrogenase activity. However, high doses of FRP inhibited the low dose pFSH stimulation of 3-beta-ol-dehydrogenase activity. High doses of pFSH (10 ug/-culture) overcame both the low dose enhancement and the high dose inhibition of FRP on 3-beta-ol-dehydrogenase activity. Kinetic analysis of FRP modulation of 3-beta-ol-dehydrogenase activity was performed substantially as described in Example Eight. The effects of FRP on 3-beta-ol-dehydrogenase activity in human placental microsomes are of a non-competitive nature.

Example Ten

Inhibition of LH/hCG Receptors In Granulosa Cells by FRP

FRP (12-18 kd., pI about 4.0-6.5) was isolated from porcine follicular fluid substantially as described in Example Three.

Granulosa Cell Cultures

The granulosa cells were counted using a hemocytometer and viability was determined by 1% trypan blue exclusion. Cells were cultured ($2 \times 10^5$) in 2 ml of Medium 100 containing 10% fetal calf serum with penicillin and streptomycin (100 g/ml and 100 U/ml respectively) in 12$\times$75 mm Falcon plastic test tubes. FSH (10 ng), and/or FRP (1 mg) were added at the initiation of culture. Media was changed after seventy-two hours.

Binding Analyses

Porcine granulosa cells were suspended in appropriate volumes of PBS-0.1% gelatin (PBS-gel). All assays were run with five concentrations of labeled hCG (10 ul), buffer (PBS-0.1% gel, 100 ul), and cells. Reactions were initiated by the addition of granulosa cells and were carried out for four hours at 25° C. All reaction tubes were precoated with 5% BSA to reduce non-specific absorption. Reactions were terminated by adding one ml of cold PBS followed by centrifugation at 30,000$\times$g for ten minutes. The supernatant was carefully aspirated and the pellet rewashed with one ml of PBS. The final pellet was counted in a gamma counter. Specific binding was calculated as the difference between binding in the presence (non-specific) and absence (total) of an excess of unlabeled hormone. Data were analyzed by Scatchard plots. Duplicate determinations were performed in three separate assays at each time interval.

Follicular protein significantly reduced porcine granulosa cell hCG binding by seventy-four hours of culture. This effect was prevented with the co-administration of FSH.

By ninety-six hours of culture, no change in porcine granulosa cell hCG binding was apparent with FSH, follicular protein, or both compared to control cultures demonstrating cellular recovery after removal of follicular protein at seventy-two hours of culture.

Thus, in addition to regulating key enzymatic steps in the steroidogenic pathway (aromatase, 3$\beta$-ol dehydrogenase), general granulosa cell response to trophic LH stimulation is also mediated by follicular protein through inhibition of LH receptor function.

Example Eleven

Adenylate Cyclase Activity

Figure 31:
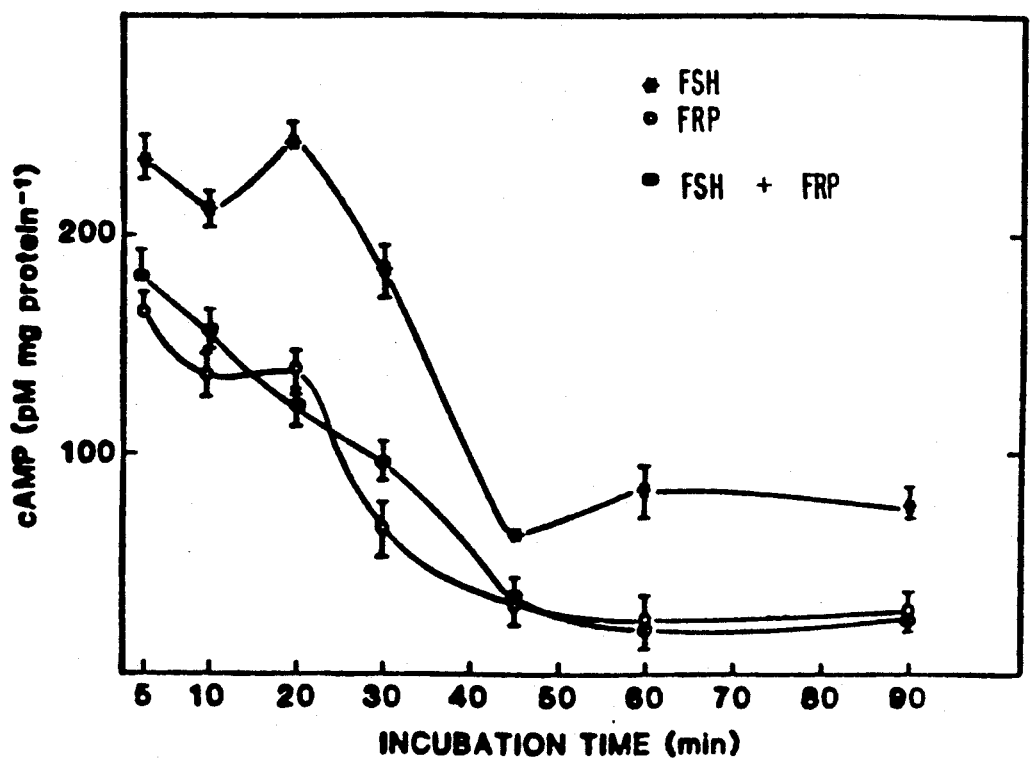
FIG. 31: Time course of FRP inhibition of Gpp (NH)p (10 uM) activated-adenylate cyclase. Adenylate cyclase activity was determined in porcine granulosa cell membranes after incubation of the cells with FSH (3.3 uM), FRP designated follicle regulatory protein (500 µg, o) or FSH (3.3 uM) and FRP (500 µg, 00) for the indicated time. Points indicate the mean of three values and the bars indicate the standard error.
Figure 32:
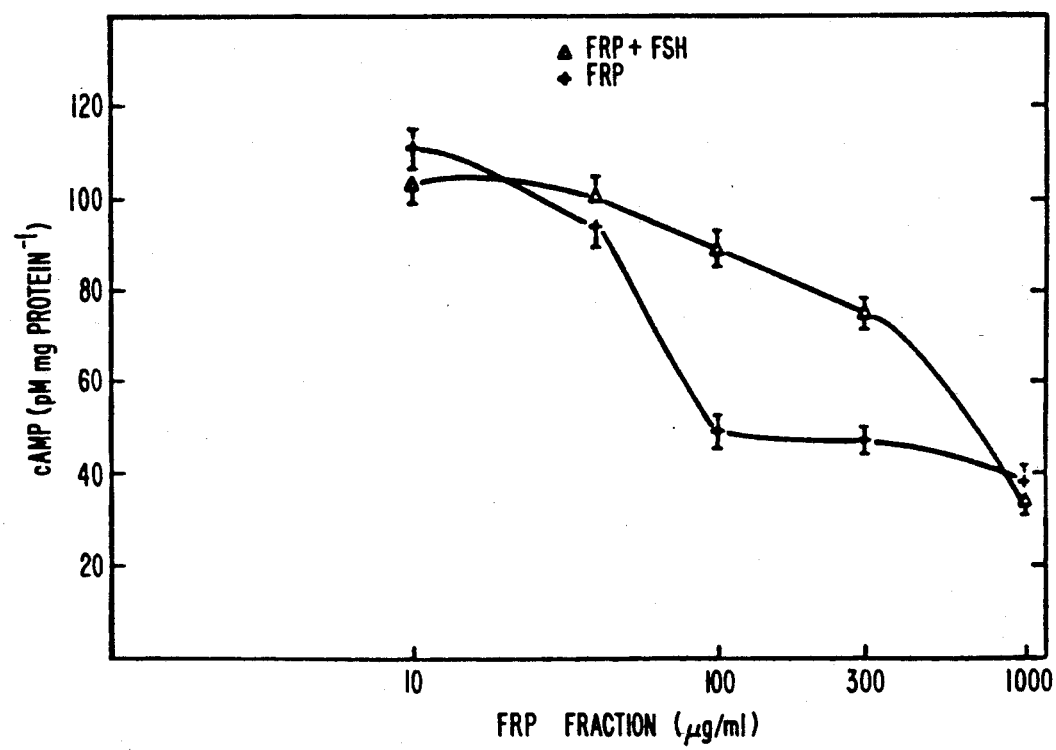
FIG. 32: Effects of FRP on Gpp(NH)p activated adenylate cyclase. Cyclic AMP formation by porcine granulosa cell membranes was measured after a thirty minute incubation with (Δ, 3.3 um) or without (+) FSH in the presence of varying concentrations of FRP. Each point represents the mean of three determinations and the bars indicate the standard deviation.
Figure 33A:
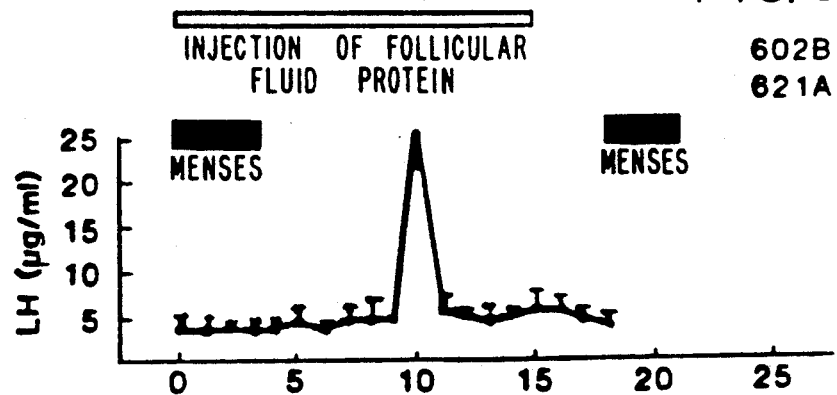
FIGS. 33a-d: Composite (X±SEM) of serum LH, FSH, estradiol, and progesterone levels from 2 rhesus monkeys which received twice daily injections (3 mg, intramuscularly) (cycle days 1-4) of FRP purified from porcine follicular fluid which does not contain inhibin F activity. Bar indicates menses. Shaded area in each panel is the 95% confidence intervals for the respective hormone levels determined for untreated, normally cycling monkey. Data have been synchronized to the LH surge (day 0).
Figure 33B:
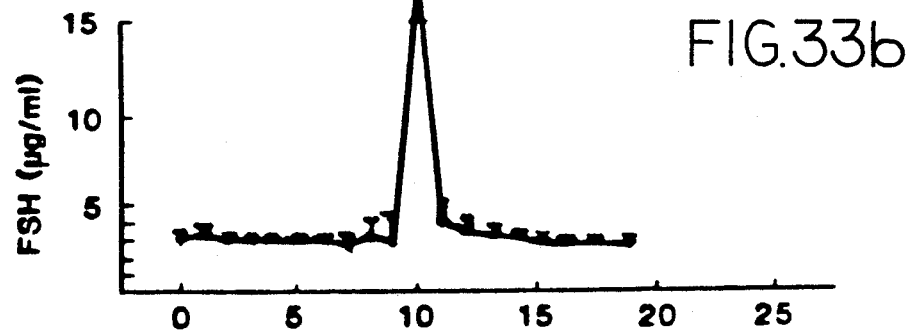
Figure 33C:
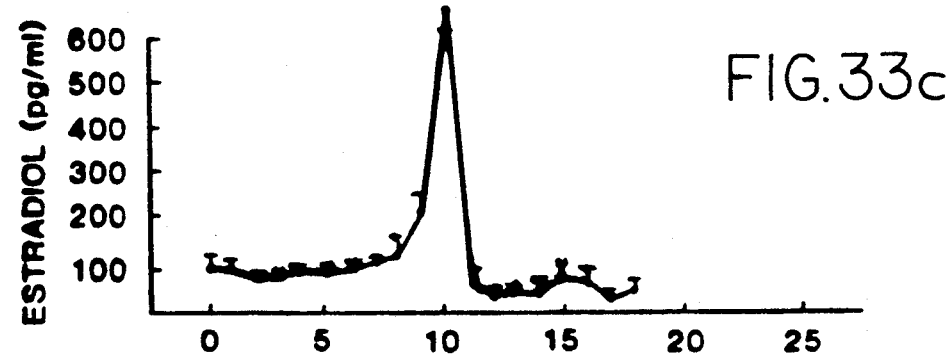
Figure 33D:
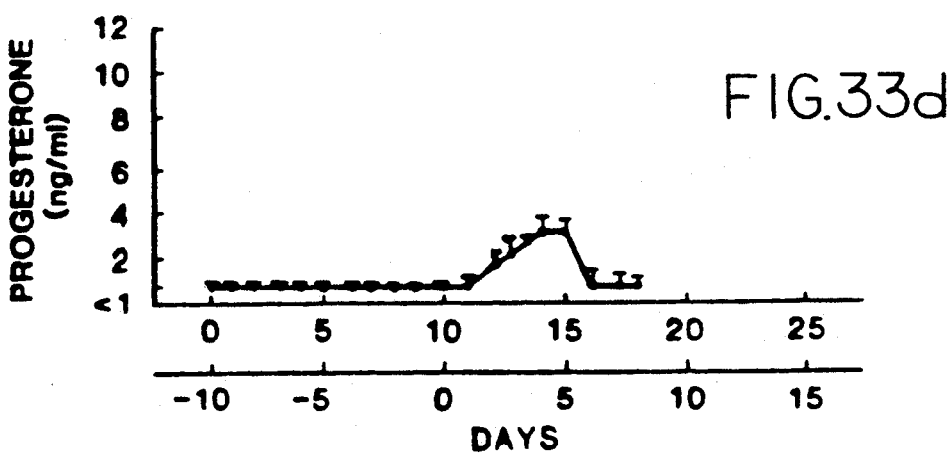
Figure 34A:
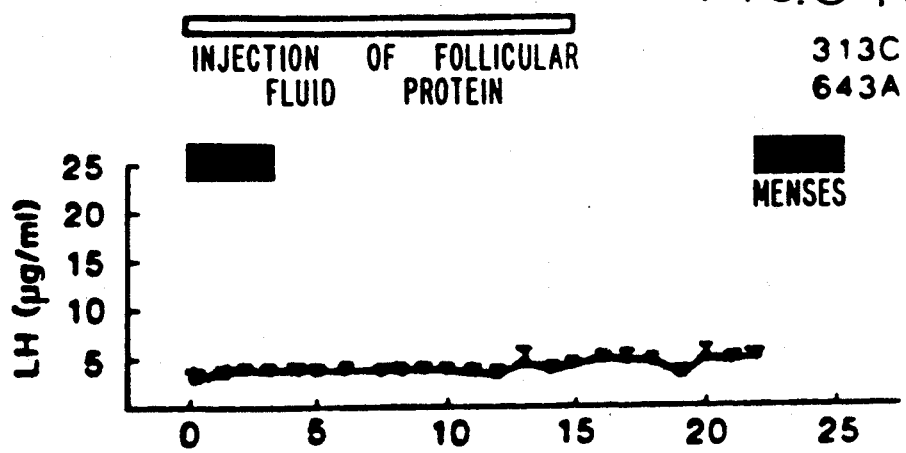
FIG. 34a-d: Composite (X±SEM) of serum LH, FSH, estradiol, and progesterone levels from 2 rhesus monkeys which received twice daily injections (3 mg, intramuscularly) of FRP partially purified from porcine follicular fluid which does not contain inhibin F activity. Bars indicate menses. Shaded area in each panel represents the 95% confidence intervals for the respective hormone levels determined for untreated normally cycling monkeys.
Figure 34B:
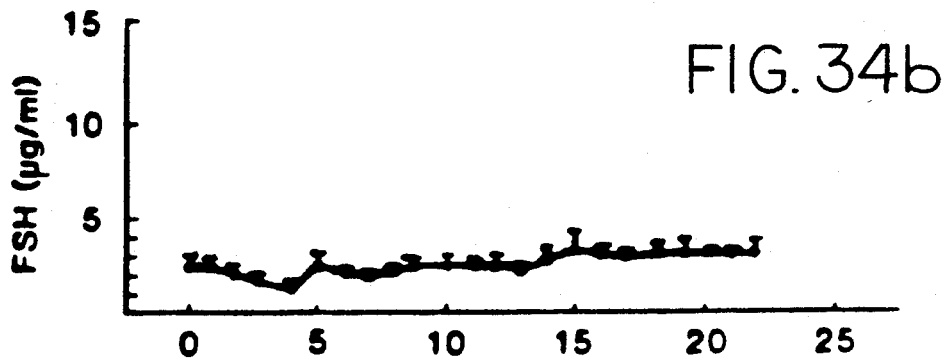
Figure 34C:
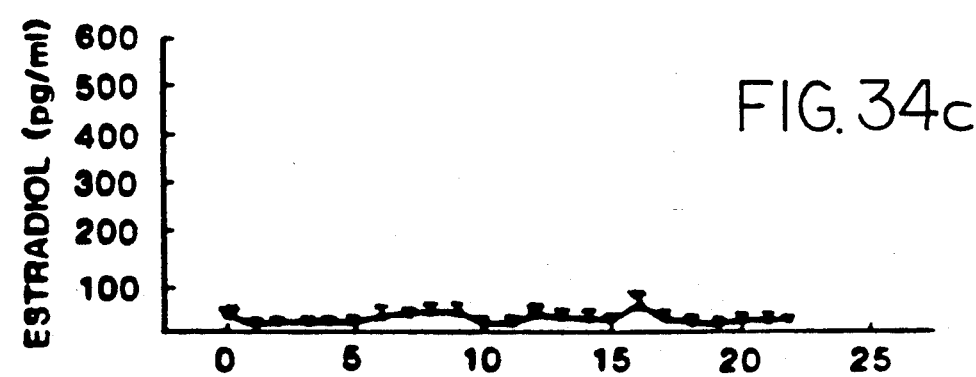
Figure 34D:
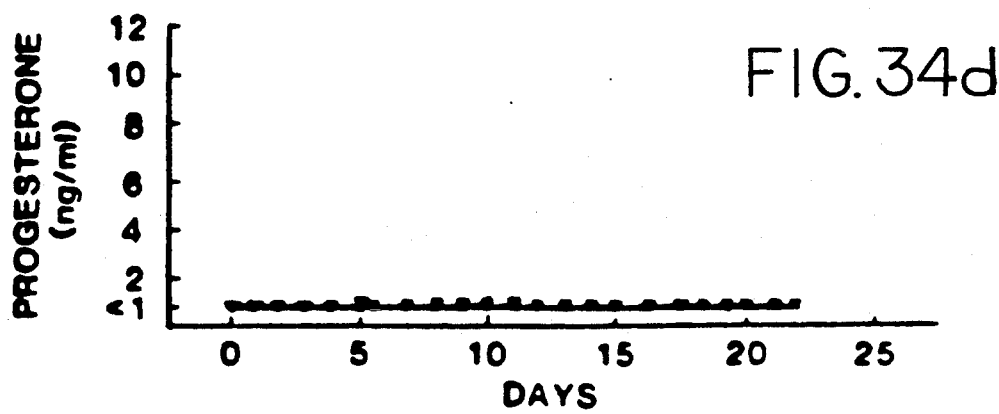

The effects of FRP on FSH-induced adenylate cyclase activity in porcine granulosa cells was evaluated using Gpp (NH)p and forskolin as pharmacological probes of adenylate cyclase activity. With the addition of 100 ug/ml of FRP (12-18,000 pI 4.0-6.5), a significant decrease in this activity was found. Maximal inhibition of cAMP formation was achieved with 1 mg/ml of FRP. Adenylate cyclase activity reached a maximum 20 min after incubation with FSH and returned to baseline by 45 minutes. FRP induced a parallel reduction in adenylate cyclase activity during this same interval of time (FIG. 31). Adenylate cyclase activity in the membranes of FRP+FSH and FRP alone treated cells was significantly less than in cells incubated with FSH ($p<0.05$). Adenylate cyclase activity of FRP treated cells was unchanged in the presence of methyl-isobutyl-xanthine. Further, when FRP was heated (56° C., 45 min.) or precipitated with 10% TCA, it lost the capability to inhibit adenylate cyclase. The 50% inhibitory dose (ID50) for FRP inhibition of Gpp(NH)p stimulated adenylate cyclase activity with preincubation of granulosa cells with FSH was 350 ug/ml and 80 ug/ml without FSH. The ID50 for the FRP inhibition of forskolin stimulated adenylate cyclase activity was 350 ug/ml (FIG. 32). Adenylate cyclase activity was determined after a 10 min. incubation with forskolin or Gpp(NH)p. When these responses were compared during a 5-20 min. interval, the Gpp(NH)p stimulated adenylate cyclase activity was more sensitive to inhibition by FRP than forskolin stimulated adenylate cyclase activity ($p<0.05$). Adenylate cyclase activity stimulated by Gpp(NH)p was also, on a molar basis, more sensitive to FRP inhibition than forskolin stimulated activity. FRP had no apparent effect on LH or hCG responsive adenylate cyclase activity in these granulosa cell preparations. No other naturally occurring substance has previously been shown to selectively inhibit FSH responsive adenylate cyclase activity in granulosa cells without also inhibiting LH responsive adenylate cyclase activity. In conclusion, these data demonstrate that FRP inhibited FSH responsive adenylate cyclase activity in porcine granulosa cells.

Example Twelve

Reduction of Follicular Atresia

Sheep have been injected intramuscularly with FRP (2 mg at 08:00 and 16:00 hours) for fourteen days. During this interval, there was a destruction of the estrous cycle such that they did not ovulate. On Day 14 of treatment the ovaries were removed, fixed in formalin, serially sectioned (4 microns) and the sections were mounted on glass slides for microscopic evaluation after staining with hematoxylin and eosin. It was evident that FRP had inhibited ovulation by blocking the normal development process whereby a developing follicle either ovulates or degenerates by becoming atretic. This was evident in development of the follicles. These findings demonstrate that the normal life span of the total follicular pool could be significantly prolonged by the therapeutic administration of FRP. With prolongation of the life span of the follicular pool, a prolongation of the reproductive capacity of an individual would naturally follow. Since the alteration in function and composition of sex steroid-dependent structures, which is commonly referred to as menopause in females, would be prevented or forestalled totally, or in part, if the sex steroid secretion was maintained, and since the ovarian follicles are the source of such sex steroids, it follows that prolongation of the life span of ovarian follicles by FRP therapy will lead to prevention or reduction of the clinical manifestations of the menopause.

III. WHOLE ANIMAL STUDIES

Example Thirteen

Inhibition of the Primate Ovarian Cycle by FRP

The Examples heretofore presented report the identification of a heat and trypsin labile protein extracted from porcine, bovine and human gonadal fluid which inhibited ovarian response to gonadotropins. The activity of this protein, secreted by human granulosa cells, increased with increasing follicular fluid estradiol levels and decreased with increasing follicular fluid progesterone levels (as shown in Example Four) both in vivo and during granulosa cells' luteinization in vitro (Example Four). This material has also been found to inhibit granulosa cell aromatase activity in both porcine (Example Three) and human (Example Four) granulosa cells in vitro. Follicular fluid extracts containing this activity are shown in said Examples to have a molecular weight of 12,000–18,000 and an isoelectric point of about pH 4.0–4.5 to 6.0–6.5, showing that the biophysical nature of this protein is not inhibin. In the present Example, the effects of this follicular protein fraction on the integrated hypothalamic-pituitary-ovarian axis of the normally cycling monkey are assessed.

Adult female rhesus monkeys (Macaca mulatta; n=8) were selected because of reproductive characteristics indicating normal ovarian function and menstrual regularity. The FRP employed in this Example was the inhibitory follicular fluid protein fraction which was obtained as described in Example Three.

Five monkeys were treated with FRP extracted from porcine follicular fluid and three monkeys served as vehicle controls. The FRP (3 mg in 1 ml of 0.01M PBS, pH 7) was administered (IM) at 07:00 hours and 19:00 hours beginning on day 1 of the menstrual cycle for a total of twenty-nine injections. Total dose for each monkey was 87 mg. Control monkeys received only PBS over the same interval. Iron supplement was administered once each week. Daily (09:00–11:00 hours), femoral blood samples (3.5 ml) were collected beginning with the onset of menses (day 1) and were continued until the onset of next menses. Radioimmunoassays for LH, FSH, $17\beta$-estradiol, and progesterone in serum were performed.

Monkeys which received FRP injections had either no serum LH peak nor elevation of serum progesterone (n=2, FIG. 33), or a midcycle LH surge followed by an inadequate luteal phase as demonstrated by low serum progesterone levels and/or early onset (twenty-four days intermenstrual interval) of vaginal bleeding (n=2, FIG. 34). One FRP treated monkey had a midcycle LH surge followed by depressed follicular phase estradiol and luteal phase serum progesterone levels (not shown). The 95% confidence limits for the vehicle control and other values obtained for this population are depicted by the shaded area in FIGS. 33 and 34. Serum estradiol levels were reduced throughout the interval of FRP treatment in the monkeys without LH surges in the late follicular phase (FIG. 34) and in those with luteal phase defects (FIG. 33). Serum FSH and LH levels were within the 95% confidence intervals for FRP treated monkeys (FIG. 33). However, in all five FRP treated monkeys, serum FSH levels rose during the course of therapy. In the monkeys with inadequate luteal phases (FIG. 33), serum estradiol levels were below the 95% confidence intervals in the late follicular and mid luteal phases. While the serum levels of both estradiol and progesterone were markedly suppressed after the LH surge. In subsequent cycles (N=3/monkey) onset of vaginal bleeding occurred in the usual twenty-six-thirty day monthly interval and no toxic effect of GRP treatments was noted.

FRP administered to normally cycling monkeys throughout the follicular phase of the menstrual cycle reduced peripheral estradiol levels without markedly affecting FSH, resulting in either apparent anovulation or inadequate luteal phases. The mixed response in serum sex steroid levels in the FRP treated monkeys may reflect a variable ovarian sensitivity to FRP. That serum FSH levels were not significantly inhibited indicates that this material has a biological activity different from that of inhibin activity in charcoal-extracted whole porcine follicular fluid. Further, when FRP was tested in an inhibin assay, its activity was either at the limits of sensitivity or undetectable. In contrast to the inhibition of FSH, normal or rising serum FSH levels during FRP treatment were found. This indicates that the purification of follicular fluid described herein removed the major inhibin activity. The molecular weight of the described FRP is less than 20,000 while inhibin activity has been associated with molecular weights greater than 45,000.

The in vivo observations of reduced serum estradiol levels in GRP treated monkeys support the previously described Examples of granulosa cell aromatase inhibition by both human and porcine derived FRP. Further, these observations are in agreement with examples of reduced serum estradiol levels in FRP treated rats.

Luteal phase defects, as evidenced by suppressed serum estradiol and progesterone levels and early onset of vaginal bleeding, result from inadequate follicular maturation in the preceding follicular phase. Taken together with the observations reported in this Example of reduced serum estradiol and progesterone levels associated with FRP treatment, these data indicate that the FRP described in the present invention has a direct intraovarian action which disrupts the normal process of folliculogenesis by an action apart from gonadotropin stimulation.

EXAMPLE FOURTEEN

Inhibition of Spermatogenesis

Male mongrel dogs were injected with 2 mg of FRP derived from porcine follicular fluid (12–18 kd., pI 4.0–6.5), as described in Example Three, at 08:00 and 16:00 hours for 20 days. On Day 20 of therapy the testis were obtained, fixed in formalin, sectioned by microtome (four micron sections), mounted on slides and stained with hematoxylin and eosin. Upon evaluation of the slides, a marked reduction in mature spermatozoa was present in the seminiferous tubules in the FRP-treated dogs as compared to the controls. Moreover, there was an 87% reduction in pacytene spermatocytes and a 44% reduction in mature spermatogonia in the FRP-treated dogs.

IV. PREPARATION OF FRP ANTIBODIES

EXAMPLE FIFTEEN

Preparation of FRP Antibodies

Antibodies (monoclonal and polyclonal) to FRP and its congeners and analogs may be prepared for diagnostic and therapeutic uses including but not limited to fertility control. Antibody in this contex refers to a synthetic protein which binds FRP and alters FRP biological activity.

Antibodies to FRP are prepared by either polyclonal or monoclonal techniques:

Polyclonal: 5 adult rabbits are immunized with 0.1 mg of FRP suspended in complete Freund's adjuvant (5 ml). One ml of this preparation is injected subcutaneously at 20 different sites in the back and neck. This is followed by monthly injections thereafter. Ear vein phlebotomies are performed after each monthly booster injection and the sera obtained are checked for titer, affinity, and specificity.

In a specific example, 1 $\mu$g of FRP (from Example Three) was solubilized in 0.5 ml physiological saline and emulsified with an equal volume of Freund's adjuvant to prepare an inoculum.

New Zealand White, female rabbits weighing 2½–3 kg were bled via the median ear artery for pre-immune serum. A 10×20 cm area on the back was shaved, then each rabbit was intradermally injected at multiple points. Approximately 50–75 $\mu$l of inoculum was injected into 10–25 sites in the shaved area; rabbits 1 and 3 received 0.6 ml and 1.6 ml, respectively. The rabbits were boosted in similar fashion six weeks later receiving 0.5 ml and 1.5 ml, respectively. Six and ten day postboost, the rabbits were test bled, again through the median artery. Sera containing the polyclonal antibodies thus obtained were titred via RIA against $^{125}$I-labelled FRP as follows.

Rabbit sera were two-fold serially diluted in RIA buffer from 1:1000 to 1:64,000. 100 $\mu$l each of the RIA buffer, diluted serum, and $^{125}$I-GRP and 200 $\mu$l RIA buffer were also prepared. The tubes were incubated at room temperature overnight. One-half ml (0.5 ml) precipitating solution containing 2% goat-anti-rabbit gamma globulin and 4% polyethylene glycol in RIA buffer was then added to each tube except the total tubes. The tubes were vortexed, incubated at room temperature for ten minutes, then centrifuged at 3000 rpm for an additional ten minutes. The supernatant was aspirated and the precipitin-pellet counted for one minute on a gamma counter. The rabbit sera was found to contain antibody which bound $^{125}$I-FRP (12 to 18 kd., pI 4.0–6.5) in all dilutions tested, including 1:64,000.

Monoclonal: BALB/c mice are immunized with FRP by intraperitoneal injection (250 ug)×2. Thereafter, the spleens are collected and cell suspensions prepared by perfusion with DMEM. The BALB/c spleen cells are fused with SP 2/0-Ag 14 mouse myeloma cells by PEG and the resultant hybridomas grown in HAT selective tissue culture media+20% fetal calf serum. The surviving cells are allowed to grow to confluence. The spent culture media is checked for antibody titer, specificity, and affinity.

Specifically, the mice were immunized with FRP (from Example Three) adjuvant emulsion described above. Each mouse first received 0.2 ml of this emulsion intraperitoneally, then were reinjected in similar fashion with 0.1 ml six weeks later. Mouse serum was obtained ten days after the second injection and then tested for anti-FRP activity via ELISA. The mouse exhibiting the highest absolute anti-FRP activity was chosen for cell fusion.

Three to four days prior to fusion, the chosen mouse was intravenously injected with 0.1 ml FRP solubilized in physiological saline, and SP2/0-Ag14 BALB/c myeloma cells maintained in log phase culture. On the day of fusion, the mouse was sacrificed and its spleen aseptically removed. Spleen cell suspension containing B-lymphocytes and macrophages were prepared by prefusion of the spleen. The cell suspension was washed and collected by centrifugation. Myeloma cells were also washed in this manner. Live cells were counted and the cells were placed in a 37° C. water bath and 1 ml of 50% poly-ethylene glycol in DMEM slowly added. The cells were incubated in the PEG for one to one-and-a-half minutes at 37° C., after which the PEG was diluted by the slow addition of media. The cells were pelleted and 35 to 40 ml of DMEM containing 10% fetal bovine serum was added. The cells were then dispensed into tissue culture plates and incubated overnight in a 37° C., 5% $CO_2$, humidified incubator.

The next day, DMEM-FCS containing hypoxanthine, thymidine, and aminopterin (HAT medium) was added to each well. The concentration of HAT in the medium to be added was twice the final concentrations required; i.e. $H_{final}=1\times10^{-4}M$, $A_{final}=4.0\times10^{-7}M$, and $T_{final}=1.6\times10^{-5}M$.

Subsequently, the plates were incubated with 1×HAT medium every three-four days for two weeks. Fused cells were thereafter grown in DMEM-FCS containing hypoxanthine and thymidine. As cell growth became ¼ to ¾ confluent on the bottom of the wells, supernatant tissue culture fluid was taken and tested for FRP-specific antibody by ELISA. Positive wells were cloned by limiting dilution over macrophage or thymocyte feeder plates, and cultured in DMEM-FCS. Cloned wells were tested and recloned three times before a statistically significant monoclonal antibody was obtained. Spent culture media from the chosen clone contained antibody which bound $^{125}$I-FRP (12–18 kd., pI 4.0–6.5) in all dilutions tested, including 1:64,000.

Each of the above described antibody containing solutions was tested against GRP secreted by granulosa cells and found to bind to independently produced FRP. Antibodies from both polyclonal and monoclonal preparations are screened for affinity by evaluating the ability to inhibit the reduction of aromatase activity by FRP in human placental microsomes. Those antibodies which block this reaction were titered by incubating various dilutions of the antibody with a fixed mass of radioactively labelled FRP in 100 µl of assay buffer (TRIS 0.025M, pH 7.4) at 4° C. overnight with constant agitation. The dilution of antibody that bound 50% of the labelled FRP under these conditions was defined as the titer. Specificity was determined in the same manner as the above only column fractions not containing FRP activity were radiolabelled and screened for antibody binding.

It will be apparent from the above description of FRP antibodies that a wide variety of diagnostic tests is possible using the antibodies of the invention. Techniques for the preparation and use of antibodies and diagnostic test methods are known in the art. Since naturally-occurring FRP plays a central role in the ovulatory process, quantification of the level of FRP in body fluids provides diagnostic information of significance. The over-production of FRP by the gonads, an indication of the presence of a condition such as ovarian cancer, could easily be detected in body fluids such as serum through the use of an immunoassay which employs the novel antibodies according to methods known in the art. Similarly, in attempting to diagnose causes of infertility, an immunoassay to detect decreased levels of FRP in the body would be a useful adjunct to known hormone assays. Further uses for the antibodies include the induction of superovulation in livestock. The direct administration of FRP antibodies to sheep has been shown to induce multiple ovulations in ewes.

More specifically, the isolation of FRP from porcine follicular fluid (12–18 kd., pI 4.0–6.5) has allowed the production of antisera containing antibody to FRP which cross-reacts with human FRP. This antibody may be used in an enzyme-linked immunosorbent assay (ELISA) and other assays suitable for quantitation of FRP in body fluids. In a particular example, an ELISA assay was used to quantitate relative FRP immunoreactivity in human serum in postmenopausal, normally menstruating and anovulatory patients.

Polyclonal antibodies were prepared from porcine FRP (12–18 kd. fraction having isoelectric points in the range of pH 4.0–4.5 and 6.0–6.5) according to the method described above, and titered via RIA against labeled porcine FRP (having similar characteristics) in dilutions up to 1:64,000.

A parallel-line dilution assay comparing the binding of the antibody to FRP in human serum to different antigen-containing samples by ELISA was performed with the following samples: porcine granulosa cell culture media, human granulosa cell culture media, human urine, bovine serum albumin, ribonuclease A and chymotrypsinogen. Immunorecognition of samples in serially-diluted porcine and human granulosa cell culture media and urine showed parallelism, whereas those of bovine serum albumin, ribonuclease A and chymotrypsinogen showed no binding, thus indicating a lack of recognition of the antibody for proteins in those materials.

The levels of FRP in the following patients was determined by ELISA assay. Ten patients undergoing ovarian extirpative surgery were all of reproductive age, and had regular menses with no clinical or laboratory evidence of ovarian dysfunction, and all underwent a total abdominal hysterectomy and bilateral salpingo-ophorectomy. Peripheral venous blood was obtained before surgery and twenty-four hours post-operative. Ten post-menopausal patients were 53–63 years of age and required hospitalization for conditions unrelated to ovarian function. Thirteen ovulatory patients, all under age 40, had problems unrelated to ovarian function including infertility due to tubal, cervical or male factor or previous tubal sterilization. These patients had regular menstrual cycles which were documented as ovulatory based on serum progesterone levels greater than 2 mg/ml. The anovulatory patients each had a history of oligomenorrhea with chronic anovulation. The anovulatory patients received 50–250 mg of chlomiphene citrate on menstrual cycle days 5–9 for ovulation induction.

Using the ELISA-determined levels of FRP in the ovulatory women as a basis, post-menopausal women had significantly lower serum levels of FRP, and similar levels were found in the serum of reproductive-age women twenty-four to forty-eight hours after ophorectomy, versus significantly higher pre-operative FRP levels in this group.

Serum FRP levels at the 3rd to 5th menstrual cycle day differed significantly in two groups of anovulatory women. A first group had high levels of serum FRP, and a second group very low levels approximating the levels of post-menopausal women. Both groups of anovulatory patients had similar low peripheral estradiol levels. The first group having low serum FRP levels comprised those with whom chlomiphene citrate therapy was successful in inducing ovulation. In contrast, the anovulatory patients with significantly elevated serum FRP levels failed to ovulate after chlomiphene therapy. Significant differences between these two groups were also apparent twenty-two to twenty-three days after the beginning of the last menstrual period. Elevated FRP levels in serum have thus been shown to be useful in predicting which anovulatory patients will or will not respond to chlomiphene citrate therapy.

As detailed above, FRP antibodies provide a wide variety of useful diagnostic procedures. A determination of the levels of FRP in mammalian body fluids, or patterns of these levels over time, and the comparison of these levels or patterns with predetermined normal data yields significant diagnostic information. For example, in one aspect of the invention FRP has been found to be substantially elevated in instances of gonadal cancer, i.e., in the body fluids of patients having ovarian or testicular cancer. It should be noted that there presently exists no reliable diagnostic test for this condition. In addition, it has also been found that varying levels of immuno-reactive FRP are found in urine during active phases of follicle growth and during lutenization, allowing the determination of the activity and timing of ovarian functions with the FRP antibodies of the invention. Further, FRP levels remain elevated during the conception cycles of pregnancy, as opposed to a pattern of luteal phase decline of FRP in non-pregnant women. Thus, a comparison of these patterns or levels provides a significant early test for pregnancy.

As noted above, it has been demonstrated that FRP levels in human body fluids vary significantly during gonadal cycles and gamete development, and antibodies to FRP have been used to monitor and predict gonadal function. These data provide methods for the diagnosis of the cause of ovarian dysfunction and for the determination of the treatment for anovulatory patients.

In Example Sixteen, a specific monoclonal antibody was produced and used in an ELISA assay to quantify and monitor human FRP levels in urine, and to establish a pattern of normal FRP levels for comparison with patterns obtained from individuals with putative ovarian dysfunction. Significant diagnostic and therapeutic advantages are obtainable with this method, as will be apparent to one having skill in the art.

Example Sixteen

A second monoclonal FRP antibody was prepared from FRP which was purified essentially as described in Example Three above, and which is more specifically described in "Biochemical and Physiological Characterization of Follicular Regulatory Protein: A Paracrine Regulator of Folliculogenesis", Ono et al., *Am. J. Obstet Gynocol.* 1986, 154:709-716, incorporated by reference herein. This protein exhibited the definitive biological effects of the inhibition of aromatase activity, LH receptor function and ovarian response to gonadotropins and had a molecular weight of about 15,000 (14-16 kd) and an isoelectric point in the range of from pH 4.5 to 6.5. Female BALB/c mice were injected with this purified FRP in a 1:1 suspension with complete Freund's Adjuvant according to standard techniques. Approximately $10^8$ spleen cells and $2 \times 10^7$ log phase myeloma cells (SP 2/0-Ag14) were mixed and pelleted at $900 \times g$ for five minutes. The cells were washed with medium, re-pelleted and resuspended in 50% peg, recentrifuged and dispensed into microculture plates containing a macrophage feeder layer and fed every three days with HAT medium. The feeder cells were BALB/c macrophages obtained by peritoneal lavage. Peritoneal exudative cells were seeded and allowed to attach overnight before fusion.

After 10-14 days in culture, the supernatant fluids from each active hybridoma were screened by an ELISA. Of the 150 hybridomas originally positive, 125 were expanded into 10 ml cultures and frozen. Of these, twenty-six continued to produce desirable antibodies. Hybridomas producing antibody were subcloned by limiting dilution on feeder layers of spleen cells until all subclones were positive for production of antibody against FRP. The colonies grown in wells seeded at one cell per well were considered monoclonal and were tested for anti-FRP antibody by the ELISA. Isotype determinations were obtained with the ELISA using mouse isotype-specific rabbit antibodies and goat anti-rabbit antibodies coupled to peroxidase.

To assess the specificity of the antibody, aliquots of FRP were analyzed on polyacrylamide gels. Samples were then electrotransferred to nitrocellulose paper, fixed, blocked in buffered saline and BSA and then incubated overnight with a 1:1,000 dilution of anti-FRP antibodies. Combined immunogold-silver staining and Auro Dye total protein staining was performed to visualize the bands. FRP immunoreactivity was measured by a competitive ELISA. And the immunohistochemical localization of FRP was accomplished by employing avidin biotinylated-peroxidase complex.

Control procedures were carried out on adjacent polyacrylamide gel sections, and the selected FRP antibody (identified as 138G3) was replaced by an irrelevant monoclonal antibody (IgMTepC183, Sigma). This antibody was diluted to give the same total protein concentration as the 138G3 FRP antibody. The specificity of the antibodies for FRP was verified by Western blot against FRP, follicular fluid and serum-free spent culture media from granulosa cells previously shown to contain FRP by bioassay. When purified fractions of FRP were injected into female rats, the ELISA detected significant immunorecognition in serum samples obtained one hour later compared to the controls. The bound and flow-through fractions from the immunoaffinity column were assessed for immunoreactivity by the ELISA and for bioactivity by inhibition of granulosal conversion of androstenedione to estrogen. The immobilized antibody (138G3) recognized FRP since the bound fraction from the immunoaffinity column had a higher specific immunoreactivity ($37.6 \pm 8$ IRU/ml) as well as bioactivity ($27.5 \pm 4\%$ inhibition of aromatase/ml) compared to the unbound fractions (undetected).

Quantitation of FRP in a variety of heterogeneous proteins by the ELISA assay using the 138G3 antibody was demonstrated. Serum from female and male rats, human seminal plasma, bovine and human serum albumin, serum and urines from patients that were menopausal or underwent oophorectomy and spent media from porcine theca cell cultures were not recognized by the assay. However, serial dilutions of equine, porcine, and human follicular fluid; spent media from human and porcine granulosa cell cultures as well as from metastatic human granulosa cell tumor, produced parallel dilution profiles.

The biotin-avidin complexed 138G3 monoclonal antibody appeared brown on hematoxylin-stained sections of ovaries. No brown staining was apparent with the use of the conjugated reagents alone nor with the biotin-avidin coupled to the irrelevant IgM at a concentration of 50 $\mu$g/ml of protein. Specific staining with 138G3 was limited to the mural granulosa cell population in follicles without histological evidence of atresia (i.e., viable follicles). No thecal, stromal or cumulus cell staining was apparent in viable follicles nor were any follicle cells stained in preantral or primordial follicles. In contrast, follicles with evidence of granulosa cell pyknosis (atretic follicles) contained enhanced staining of all follicular epithelial cells.

The 138G3 antibody was employed in an ELISA assay to determine levels of FRP in the urine of twelve regularly menstruating women over time. These levels, and the simultaneously-obtained serum levels of LH, FSH, estradiol and progesterone as well as ultrasonographic determination of the largest follicle diameter are shown in FIG. 35. Urinary levels of FRP were detectable above baseline five days before the LH surge, continued to rise thereafter reaching maximum levels four to five days after the LH surge, and then declined through the late luteal phase. This pattern correlates with the decrease in the number of healthy follicles during the pariovulatory and mid-luteal phases of the menstrual cycle. The lowest FRP levels occurred during the early follicular phase, a time which is characterized by the largest number of viable follicles during the menstrual cycle. Viable follicles are not likely to be a predominant source of FRP in the luteal phase since their number decreases during this time. During the luteal phase the number of atretic follicles increases, especially those 4-6 mm in diameter. This temporal correlation between rising levels of FRP and an increase in the number of atretic follicles suggests that the corpus luteum may play a role in the induction of atresia.

Inappropriate exposure to elevated FRP levels could limit the ability of follicles to respond to FSH resulting in a suppressed follicular maturation and estradiol production. A group of anovulatory patients with serum gonadrotropin levels within the normal range was found to have elevated levels of immunoreactive FRP in their peripheral serum. A differential ovarian response to clomiphene citrate therapy by these anovulatory patients (as described above) was observed on days 11-12 of the menstrual cycle. There appeared to be follicular abnormalities during the intercycle interval as demonstrated by reduced serum estradiol levels and concomitant elevations in serum FRP levels 3-5 days after the onset of the last menstrual period.

Comparison of the above data with the control levels set forth in FIG. 35, provides a determination of gonadal function, specifically the determination and treatment of anovulatory patients. For example, anovulation may result from an overproduction of FRP and subsequent reduction in follicular responsivity to gonadotropin stimulation. That additional gonadotropin exposure was not successful in overcoming this putative FRP-induced block in follicular maturation is evidenced by the elevated levels of FRP in other anovulatory patients 11-12 and 22-23 days after the onset of the last menstrual period even after receiving clomiphene citrate therapy on days 3-7 of the cycle. Anovulatory patients who responded to clomiphene citrate therapy by increasing their peripheral estradiol levels on days 11-12 and presumably ovulated as evidenced by elevated serum progesterone levels on days 22-23 did not have elevated FRP levels during these intervals. Thus, follicular dysfunction expressed clinically as anovulatory cycles can be properly identified as resulting from abnormalities in ovarian protein, or in steroid hormone secretion.

The invention in general in certain aspects in particular are broad in scope, for example, the proteinaceous substance of the invention may be produced by other methods.

In particular, a c-DNA probe can be prepared against the biologically active portion of FRP and used to identify the FRP genome in granulosa cells or Sertoli cells from any mammalian species. The identified genome can then be synthesized into a plasmid which can then be employed to produce recombinant DNA in proliferating bacteria according to methods known in the art.

In addition, granulosa or Sertoli cells may be transformed, e.g. by SV40 virus, to produce FRP quantity.

In summary, the intergonadal protein, its identifying characteristics, methods of production and uses set forth herein identify a novel and unique proteinaceous substance. FRP is described herein to be the only proteinaceous substance known which inhibits aromatase activity by determination of the extent of the conversion of androgens to estrogens. Moreover, such inhibition is unique in that it is non-competitive in placental microsomes. Further, FRP produces a biphasic effect on 3β-ol dehydrogenase activity in cultured granulosa cells as shown in FIGS. 29 and 30.

In addition, FRP inhibits FSH induction of LH receptor formation as determined by addition to an in vitro culture of granulosa cells, and inhibits FSH responsive adenylate cyclase activity as similarly determined.

In addition to this biological activity, FRP is identified by the elution profile through a molecular weight exclusion column under the conditions set forth in Example Two, as indicated by the designation "FRP" of the elution curve in FIG. 9. The elution profile through a hydrogen ion exclusion column, particularly the area designated by the indicated peaks numbers 4 and 7 in FIG. 15, further identifies identifying characteristics of FRP when conducted under the conditions set forth in the Example Three. Moreover, a polyacrylamide gel electrophoretic pattern from a high pressure liquid chromatographic column, as shown by the designation "FRP" in column 6 of FIG. 11, uniquely identifies FRP when the pattern is obtained as set forth in Example Two.

From the foregoing description, one skilled in the art can easily ascertain the essential characteristics of the invention and, without departing from the spirit and scope thereof, can adapt the invention to various usages and conditions. The regulatory protein described herein is defined primarily by its biological effect in a biological system. This phrase is meant to define a reversible effect, that is, one that does not involve the destruction of endocrine functions such as by the heating or other denaturation of proteins. For example, the administration of the protein to a mammal inhibits aromatase activity, and the cessation of this administration allows the reversal of the inhibitory effect.

While the biological activities set forth herein define the protein, the physical characteristics set forth also provide distinguishing features. The protein moeity which provides the described biological activity shows a wide range of molecular weights (from 5,500 to 18,000 daltons) and an electrophoretic range of from about pH 3.5 to about 7.0. More preferably, the physical characteristics of the protein are identified as ranging from a molecular weight of about 10,000 up to 18,000 daltons, and having an isoelectric point of from about pH 4.0 to about 6.5. Based on the data set forth herein, the physical characteristics of the protein moeity which produces the above-described antibody has a molecular weight of about 15,000 daltons and an isoelectric point of about pH 4.5 to 4.75. However, changes in form and the substitution of equivalents are contemplated as circumstances may suggest or render expedient; and although specific terms have been employed herein, they are intended in a descriptive sense and not for purposes of limitation, the scope of the invention being delineated in the following claims.

What is claimed is:

1. A method for quantifying follicular regulatory protein (FRP) in a body fluid of a mammal, comprising:
    a) contacting said fluid with an antibody which specifically binds FRP, said FRP being characterized in that it:
        i) inhibits intragonadal activity of aromatase, as measured by the conversion of androgens to estrogens;
        ii) does not affect normal intragonadal FSH level while inhibiting said aromatase activity; and
        iii) has a molecular weight of from about 10,000 daltons to about 18,000 daltons and an isoelectric point of about pH 4.0 to 6.5 as determined by electrophoretic mobility or hydrogen ion chromatography; and b) determining said specific binding of said antibody to said FRP to quantitate said FRP in said body fluid.

2. The method of claim 1 wherein said FRP has a molecular weight of about 15,000 daltons and an isoelectric point of about pH 4.5 to 4.75.

3. The method of claim 1 wherein said FRP has the further biological activity of:
   a) producing an increase in 3-$\beta$-ol dehydrogenase activity above baseline level with a dose of about 167 $\mu$g/ml of FRP, and a return to said baseline level with a dose of about 500 $\mu$g/ml of FRP;
   b) inhibiting FSH induction of LH receptor binding function; and
   c) inhibiting FSH responsive adenylate cyclase activity, as determined in cultured porcine granulose cells.

4. A method for monitoring gonadal function in a mammal by quantifying the level of follicular regulatory protein (FRP) in a body fluid of a mammal, which comprises:
   a) conducting an assay which comprises:
      i) contacting said fluid with an antibody which specifically binds to FRP, said FRP being characterized in that it:
         a) inhibits intragonadal activity of aromatase, as measured by the conversion of androgens to estrogens;
         b) does not affect normal intragonadal FSH level while inhibiting aromatase activity; and
         c) has a molecular weight of from about 10,000 daltons to about 18,000 daltons and an isoelectric point of about pH 4.0 to 6.5 as determined by electrophoretic mobility or hydrogen ion chromatography;
      ii) determining said specific binding of said antibody to said FRP to quantitate said FRP in said body fluid; and
   b) comparing said FRP level in said body fluid to a control FRP level obtained from a control body fluid to monitor the relative production of FRP by said gonadal function.

5. A method of claim 4 wherein the determination of FRP levels in the body fluid is repeated to produce a pattern of the variation of such levels over time, and this determined pattern is compared with a control pattern which indicates a normal FRP pattern over time.

6. The method of claim 4 wherein said FRP has a molecular weight of about 15,000 daltons and an isoelectric point of about pH 4.5 to 4.75.

7. The method of claim 4 wherein said FRP has the further biological activity of:
   a) producing an increase in 3-$\beta$-ol dehydrogenase activity above baseline level with a dose of about 167 $\mu$g/ml of FRP, and a return to said baseline level with a dose of about 500 $\mu$g/ml of FRP;
   b) inhibiting FSH induction of LH receptor binding function; and
   c) inhibiting FSH responsive adenylate cyclase activity, as determined in cultured porcine granulosa cells.

8. A method for predicting gonadal normal function or dysfunction which comprises:
   a) determining the levels of follicular regulatory protein (FRP) in a body fluid of a mammal over a predetermined time period which comprises:
      i) contacting said fluid with an antibody which specifically binds to FRP, said FRP being characterized in that it:
         a) inhibits intragonadal activity of aromatase, as measured by the conversion of androgens to estrogens;
         b) does not affect normal intragonadal FSH level while inhibiting said aromatase activity; and
         c) has a molecular weigh of from 10,000 daltons to about 18,000 daltons and an isoelectric point of about pH 4.0 to 6.5 as determined by electrophoretic mobility or hydrogen ion chromatography;
      ii) determining said specific binding of said antibody to said FRP to quantitate said FRP in said body fluid; and
   b) comparing said FRP levels in said body fluid over said predetermined time period to control FRP levels obtained from a normal control body fluid over the same predetermined time period to predict gonadal normal function or dysfunction.

9. The method of claim 8 wherein said FRP has amolecular weight of about 15,000 daltons and an isoelectric point of about pH 4.5 to 4.75.

10. The method of claim 8 wherein said FRP has the further biological activity of:
    a) producing an increase in 3-$\beta$-ol dehydrogenase activity above baseline level with a dose of about 167 $\mu$g/ml of FRP, and a return to said baseline level with a dose of about 500 $\mu$g/ml of FRP;
    b) inhibiting FSH induction of LH receptor binding function; and
    c) inhibiting FSH responsive adenylate cyclase activity, as determined in cultured porcine granulosa cells.

* * * * *

UNITED STATES PATENT AND TRADEMARK OFFICE
CERTIFICATE OF CORRECTION

PATENT NO. : 5,173,404
DATED : December 22, 1992
INVENTOR(S) : diZerega

It is certified that error appears in the above-indentified patent and that said Letters Patent is hereby corrected as shown below:

Col. 5, line 47, delete "5.500" and insert --5,500--.

Col. 5, line 68, delete "+" and insert --±--.

Col. 22, line 3, delete "30".

Col. 25, line 31, insert a space between "P" and "assay".

Col. 26, line 56, delete "protein-" and insert --protein/--.

Col. 29, line 4, insert a hyphen between "substrate" and "specific".

Col. 40, lines 34 and 43, change "moeity" to --moiety--.

Col. 42, line 39, insert a space between "a" and "molecular".

Signed and Sealed this

Twenty-fifth Day of January, 1994

Attest:

BRUCE LEHMAN

*Attesting Officer*     *Commissioner of Patents and Trademarks*